US009096515B2

(12) United States Patent
Bhat et al.

(10) Patent No.: US 9,096,515 B2
(45) Date of Patent: Aug. 4, 2015

(54) METHODS OF USING CYCLOALKYLMETHYLAMINE DERIVATIVES

(71) Applicant: Reviva Pharmaceuticals, Inc., San Jose, CA (US)

(72) Inventors: Laxminarayan Bhat, Cupertino, CA (US); Kouacou Adiey, San Jose, CA (US)

(73) Assignee: REVIVA PHARMACEUTICALS, INC., Santa Clara, CA (US)

( * ) Notice: Subject to any disclaimer, the term of this patent is extended or adjusted under 35 U.S.C. 154(b) by 0 days.

(21) Appl. No.: 14/038,543

(22) Filed: Sep. 26, 2013

(65) Prior Publication Data
US 2014/0024709 A1 Jan. 23, 2014

Related U.S. Application Data

(62) Division of application No. 13/175,824, filed on Jul. 1, 2011, now Pat. No. 8,604,244.

(60) Provisional application No. 61/361,108, filed on Jul. 2, 2010.

(51) Int. Cl.
| | |
|---|---|
| C07C 211/00 | (2006.01) |
| A01N 33/02 | (2006.01) |
| A61K 31/135 | (2006.01) |
| C07C 69/34 | (2006.01) |
| C07C 209/48 | (2006.01) |
| C07C 209/88 | (2006.01) |
| C07C 211/26 | (2006.01) |
| C07C 213/06 | (2006.01) |
| C07C 213/10 | (2006.01) |
| C07C 217/74 | (2006.01) |
| C07C 219/06 | (2006.01) |
| C07C 231/02 | (2006.01) |
| C07C 237/06 | (2006.01) |
| C07C 271/20 | (2006.01) |
| C07C 229/34 | (2006.01) |
| C07C 69/96 | (2006.01) |
| C07C 237/22 | (2006.01) |

(52) U.S. Cl.
CPC ............... *C07C 69/34* (2013.01); *C07C 69/96* (2013.01); *C07C 209/48* (2013.01); *C07C 209/88* (2013.01); *C07C 211/26* (2013.01); *C07C 213/06* (2013.01); *C07C 213/10* (2013.01); *C07C 217/74* (2013.01); *C07C 219/06* (2013.01); *C07C 229/34* (2013.01); *C07C 231/02* (2013.01); *C07C 237/06* (2013.01); *C07C 237/22* (2013.01); *C07C 271/20* (2013.01); *C07C 2101/04* (2013.01)

(58) Field of Classification Search
None
See application file for complete search history.

(56) References Cited

U.S. PATENT DOCUMENTS

| | | | |
|---|---|---|---|
| 3,845,770 | A | 11/1974 | Theeuwes et al. |
| 3,916,899 | A | 11/1975 | Theeuwes et al. |
| 4,522,828 | A | 6/1985 | Jeffery et al. |
| 4,629,727 | A | 12/1986 | Kozlik et al. |
| 4,667,054 | A | 5/1987 | Miyazawa et al. |
| 4,833,143 | A | 5/1989 | Armitage et al. |
| 4,925,879 | A | 5/1990 | Housley et al. |
| 4,929,629 | A | 5/1990 | Jeffery |
| 5,015,644 | A | 5/1991 | Roth et al. |
| 5,047,432 | A | 9/1991 | Housley et al. |
| 5,112,598 | A | 5/1992 | Biesalski |
| 5,436,272 | A | 7/1995 | Scheinbaum |
| 5,556,611 | A | 9/1996 | Biesalski |
| 5,596,019 | A | 1/1997 | Mattson |
| 5,698,155 | A | 12/1997 | Grosswald et al. |
| 6,610,887 | B2 | 8/2003 | Senanayake et al. |
| 7,989,500 | B2 | 8/2011 | Bhat et al. |
| 2004/0121965 | A1 | 6/2004 | Greenberger et al. |
| 2008/0139663 | A1 | 6/2008 | Bhat et al. |

FOREIGN PATENT DOCUMENTS

| | | |
|---|---|---|
| CA | 1248955 | 1/1989 |
| EP | 0293880 | 12/1988 |
| GB | 2098602 | 11/1982 |
| GB | 2127819 | 4/1984 |
| WO | WO 90/15048 | 12/1990 |

(Continued)

OTHER PUBLICATIONS

International Search Report and Written Opinion of PCT App. No. PCT/US2011/042887 with a mailing date of Feb. 3, 2012.

(Continued)

*Primary Examiner* — Clinton Brooks
(74) *Attorney, Agent, or Firm* — Perkins Coie LLP; Viola T. Kung

(57) ABSTRACT

The present invention provides novel cycloalkylmethylamine derivatives, and methods of preparing cycloalkylmethylamine derivatives. The present invention also provides methods of using cycloalkylmethylamine derivatives and compositions of cycloalkylmethylamine derivatives. The pharmaceutical compositions of the compounds of the present invention can be advantageously used for treating and/or preventing obesity and obesity related co-morbid indications and depression and depression related co-morbid indications.

20 Claims, No Drawings

(56) References Cited

FOREIGN PATENT DOCUMENTS

| WO | WO 98/11884 | 3/1998 |
|---|---|---|
| WO | WO 98/13034 | 4/1998 |
| WO | WO 00/32178 | 6/2000 |
| WO | WO 01/00187 | 1/2001 |
| WO | WO 01/00205 | 1/2001 |
| WO | WO 01/51453 | 7/2001 |
| WO | WO 02/36540 | 5/2002 |
| WO | WO 02/060424 | 8/2002 |
| WO | WO 02/083631 | 10/2002 |
| WO | WO 2004/058237 | 7/2004 |
| WO | WO 2004/096202 | 11/2004 |
| WO | WO 2007/081857 | 7/2007 |
| WO | WO 2008/034142 | 3/2008 |

OTHER PUBLICATIONS

Miyano, et al.; "Grignard Reaction and Products. I. 1,4-Addition of Arylmagnesium Bromide to 2-Alkylidenecyclohexanone and the Oxidative Cleavage therein"; Chemical and Pharmaceutical Bulletin; vol. 18, No. 9, pp. 1799-1805 (1970).

Patani, et al.; "Bioisoterism: A Rathional Approach in Drug Design"; Chem. Rev.; vol. 96, No. 8, pp. 3147-3176 (1996).

METHODS OF USING CYCLOALKYLMETHYLAMINE DERIVATIVES

This application is a divisional application of U.S. application Ser. No. 13/175,824, filed Jul. 1, 2011; which claims priority to Provisional Application No. 61/361,108, filed Jul. 2, 2010. The above-identified applications are incorporated herein by reference in their entireties.

TECHNICAL FIELD

The present invention relates to cycloalkylmethylamine derivatives, synthesis of cycloalkylmethylamine derivatives and methods of using cycloalkylmethylamine derivatives for the pharmacological treatment of obesity and obesity related co-morbid indications.

BACKGROUND

Obesity is a chronic disease that affects millions of people across the world especially in the developed countries. It is defined by excess body fat and is generally measured by calculating a person's BMI (body mass index). If a person's BMI is 30 or above, he or she considered to be obese. Obesity can cause a number of health problems either directly or indirectly, such as, for example, type 2 diabetes, coronary heart disease, high blood triglycerides, high blood pressure and stroke. Obesity also raises risk of certain types of cancer. Obese men are more likely than normal-weight peers to die from cancer of the colon, rectum, and prostate. Obese women are more likely than non-obese women to die from cancer of the gallbladder, breast, uterus, cervix and ovaries. Death from some cancers may be more likely because obesity makes the cancers harder to detect in the early stages (for example, the initial small lump of breast cancer may not be felt in an obese woman). Recent studies show obesity increases the risk of Alzheimer's-type dementia. Other disease and health problems linked to obesity include: gallbladder disease, gallstones, osteoarthritis, gout or joint pain, sleep apnea, psychological and social problems.

Obesity is caused by multiple factors, the primary factor being genetics which is the one factor relating to obesity over which individuals have no control. Other important factors involved in obesity are: the mechanisms of fat storage; the balance between energy intake and energy expenditure; an individual's life style: eating habits and exercise; and psychological, cultural and socioeconomic influences. Despite the seeming inexorable progression of this disease, there have been limited advances in the pharmacotherapy of this condition. Drugs to treat obesity can be divided into three groups: those that reduce food intake or appetite suppressants; those that alter metabolism or block the absorption of fat; and those that increase thermogenesis. Currently, there are only two drugs approved by the FDA for the long-term treatment of obesity and they are fat absorption blocker orlistat (XENICAL®) and the appetite suppressant sibutramine (MERIDIA®). The only thermogenic drug combination that has been tested is ephedrine and caffeine, but this treatment has not been approved by regulatory agencies.

The fat absorption blocker, orlistat works in the gastrointestinal tract by blocking an enzyme that is needed to digest fat. Instead of being absorbed from the intestine, up to one-third of the fat that a person consumes is excreted in the stool. In addition, orlistat blocks the absorption of needed fat-soluble vitamins A, D, E, and K, as well as beta-carotene. This is one of the major limitations of this drug for the long term use in the treatment of obesity. Most commonly reported other side effects of orlistat are bloating, diarrhea and oily stools.

In the appetite suppressant category, a few noradrenergic and serotonergic drugs belong to a family of 2-arylethylamines are currently available in the market for the treatment of obesity. The noradrenergic agents such as phenylpropanolamine, (ACUTRIM®, DEXATRIM®), diethylpropion (TENUATE®), and phentermine (FASTIN®, IONAMIN®) are approved for the short-term treatment of obesity. Whereas, noradrenergic and serotonergic agent sibutramine (MERIDIA®) is the only drug currently approved for the long-term treatment of obesity in the appetite suppressant category. Sibutramine has cyclobutanemethylamine backbone and it is this backbone mainly responsible for its unique pharmacological properties.

In the last 10 years, a number of reports have been published on the possible use of sibutramine, either alone or in combination with other therapeutic agents, for the treatment and/or prevention of a variety diseases and/or disorders in addition to obesity (see, Montana, J. G. International Application Publication No. WO 2004/058237; Lulla, A. et al., International Application Publication No. WO 2004/096202; Jerussi, T. P. et al., International Application Publication No. WO 02/060424; Senanayake, C. H. et al., International Application Publication No. WO 01/51453; Heal, D. J. International Application Publication No. WO 01/00205; Birch, A. M. et al., International Application Publication No. WO 01/00187; Mueller, P. International Application Publication No. WO 00/32178; Bailey, C. International Application Publication No. WO 98/11884; Kelly, P. International Application Publication No. WO 98/13034). For examples: treatment of nausea, emesis, and related conditions; cognitive dysfunctions; eating disorders; weight gain; irritable bowel syndrome; obsessive compulsive disorders; platelet adhesion; apnea, affective disorders such as attention deficit disorders, depression, and anxiety; male and female sexual function disorders; restless leg syndrome; osteoarthritis; substance abuse including nicotine and cocaine addiction; narcolepsy; pain such as neuropathic pain, diabetic neuropathy, and chronic pain; migraines; cerebral function disorders; chronic disorders such as premenstrual syndrome; and incontinence.

In general, sibutramine has a number of therapeutic benefits because of its unique pharmacological properties. However, sibutramine's therapeutic use for the treatment of obesity, and other diseases and disorders is currently not fully utilized because of certain limitations and adverse side effects associated with the drug. The major adverse events reported, in some cases life threatening, include increase in blood pressure and the side effects derived from the drug-drug interactions, for example, serotonin syndrome. The majority of these adverse events are, to some extent, metabolism-based. Sibutramine exerts its pharmacological actions predominantly via its secondary ($M_1$) and primary ($M_2$) amine metabolites. Sibutramine is metabolized in the liver principally by the cytochrome P450 (3A4) isozymes, to desmethyl metabolites, $M_1$ and $M_2$. These active metabolites are further metabolized by hydroxylation and conjugation to pharmacologically inactive metabolites, $M_5$ and $M_6$. The elimination half-lives of therapeutically active primary and secondary metabolites $M_1$ and $M_2$ are 14 and 16 hours, respectively. It is evident from a number literature reports that cytochrome P450 mediated metabolism and the long half lives of active metabolites ($M_1$ and $M_2$) are to a great extent responsible for adverse events such as increased blood pressure and other side effects derived from drug-drug interactions of sibutramine.

Therefore, there is a need and great demand for safer and effective next generation appetite suppressants for the treatment of obesity. An ideal drug in this class should have potent appetite suppressant activity, a proven effect on fat loss, be well tolerated during acute and chronic administration and have alleviated side effects when compared to sibutramine and phentermine.

SUMMARY

The present invention is directed towards compositions of novel cycloalkylmethylamine derivatives and the use of the compositions for the treatment of obesity and related co-morbid conditions and depression and related co-morbid conditions. The present invention provides methods for synthesizing such cycloalkylmethylamine derivatives. The present invention also provides methods for using cycloalkylmethylamine derivatives and pharmaceutical composition of cycloalkylmethylamine derivatives for treating or preventing obesity and co-morbid diseases and/or disorders and for treating or preventing depression and co-morbid diseases and/or disorders.

The compounds of the present disclosure are advantageous because of their favorable metabolic, pharmacokinetics and pharmacological profiles.

In various aspects, the present disclosure provides cycloalkylmethylamine derivatives of structural Formulae (I) or (II):

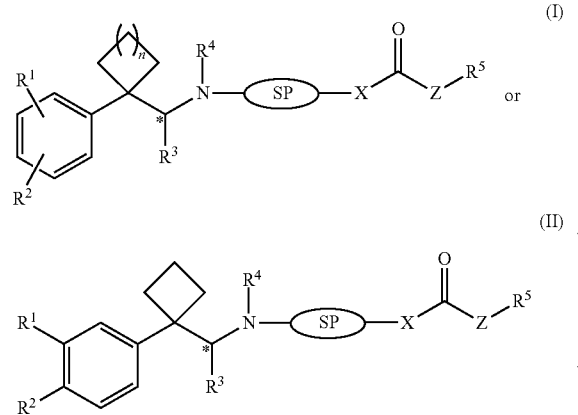

or isomer or pharmaceutically acceptable salt thereof, wherein:
n is 0, 1, 2, 3, 4, or 5;
SP is a spacer, wherein the spacer is $C_{1-6}$ alkylene, and wherein one or more of the carbons of the $C_{1-6}$ alkylene can optionally be replaced with O, S, or $NR^6$, wherein $R^6$ can be H or $C_{1-6}$ alkyl;
X is O, S, NH, $CH_2$, or alkylene;
Z is O, S, NH, $CH_2$, or a direct bond;
$R^1$, $R^2$, $R^3$, $R^4$, and $R^5$ are each independently hydrogen, $C_{1-6}$ alkyl, aryl, arylalkyl, cycloalkyl, cycloheteroalkyl, heteroaryl, heteroarylalkyl, acylalkyloxycarbonyl, acyloxyalkyloxycarbonyl, acylalkyloxycarbonylamino, acyloxyalkyloxycarbonylamino, $C_{1-6}$ alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonyalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^2$, $R^3$, $R^4$, and $R^5$ can be substituted with the isotopes $^2H$ (deuterium), 3H (tritium), 13C, 36Cl, 18F, 15N, 17O, 18O, 31P, 32P, and 35S; and "*" denotes a carbon capable of being optically active.

The compounds of the present disclosure include R isomers, S isomers, and mixtures of R and S isomers.

In certain aspects, the present disclosure provides cycloalkylmethylamine derivatives of structural Formulae (III), (IV), (V), (VI), (VII), (VIII), or (IX):

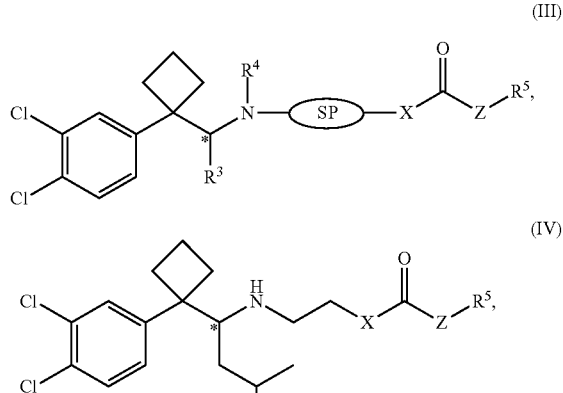

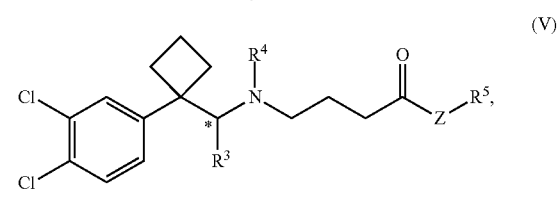

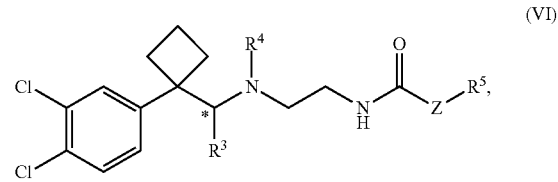

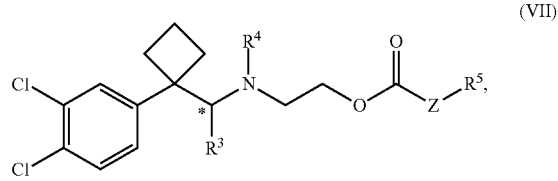

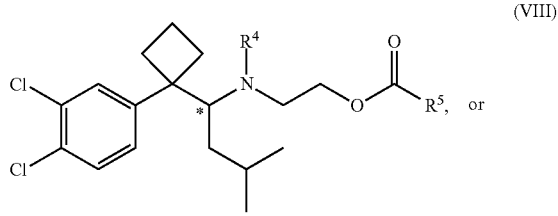

-continued

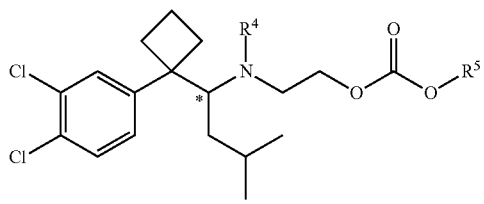

(IX)

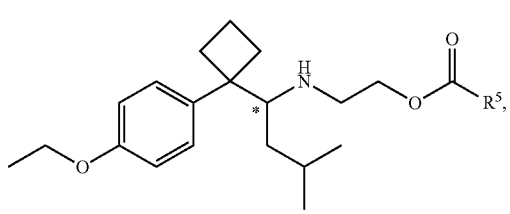

(XII)

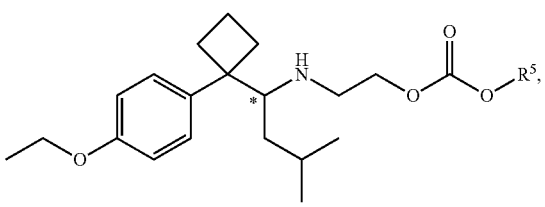

(XIII)

or isomer or pharmaceutically acceptable salt thereof, wherein:

n is 0, 1, 2, 3, 4, or 5;

SP is a spacer, wherein the spacer is $C_{1-6}$ alkylene, and wherein one or more of the carbons of the $C_{1-6}$ alkylene can optionally be replaced with O, S, or $NR^6$, wherein $R^6$ can be H or $C_{1-6}$ alkyl;

X is O, S, NH, $CH_2$, or alkylene;

Z is O, S, NH, $CH_2$, or a direct bond;

$R^1$, $R^2$, $R^3$, $R^4$, and $R^5$ are each independently hydrogen, $C_{1-6}$ alkyl, aryl, arylalkyl, cycloalkyl, cycloheteroalkyl, heteroaryl, heteroarylalkyl, acylalkyloxycarbonyl, acyloxyalkyloxycarbonyl, acylalkyloxycarbonylamino, acyloxyalkyloxycarbonylamino, $C_{1-6}$ alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^2$, $R^3$, $R^4$, and $R^5$ can be substituted with the isotopes $^2H$ (deuterium), $^3H$ (tritium), $^{13}C$, $^{36}Cl$, $^{18}F$, $^{15}N$, $^{17}O$, $^{18}O$, $^{31}P$, $^{32}P$, and $^{35}S$; and "*" denotes a carbon capable of being optically active.

The compounds of the present disclosure include R isomers, S isomers, and mixtures of R and S isomers.

In certain aspects, the present disclosure provides cycloalkylmethylamine derivatives of structural Formulae (X), (XI), (XII), (XIII), (XIV), (XV), (XVI), or (XVII):

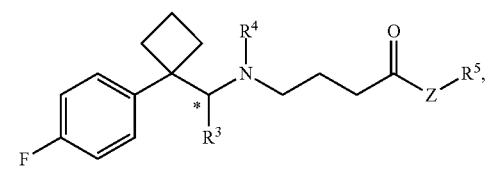

(XIV)

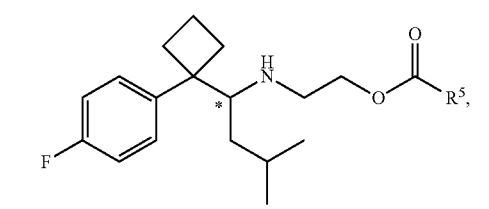

(XV)

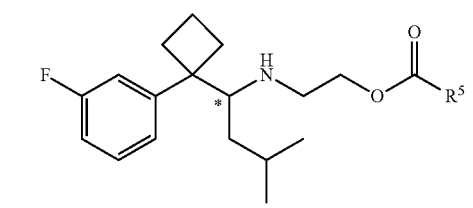

(XVI)

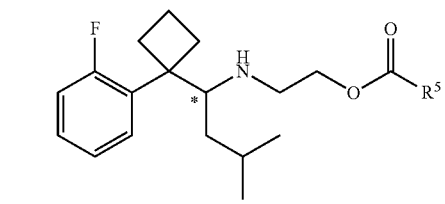

(XVII)

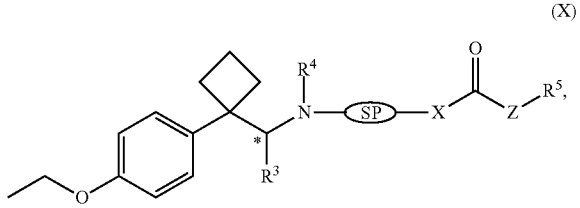

(X)

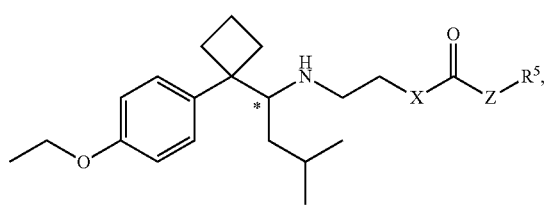

(XI)

or isomer or pharmaceutically acceptable salt thereof, wherein:

n is 0, 1, 2, 3, 4, or 5;

SP is a spacer, wherein the spacer is $C_{1-6}$ alkylene, and wherein one or more of the carbons of the $C_{1-6}$ alkylene can optionally be replaced with O, S, or $NR^6$, wherein $R^6$ can be H or $C_{1-6}$ alkyl;

X is O, S, NH, $CH_2$, or alkylene;

Z is O, S, NH, $CH_2$, or a direct bond;

$R^1$, $R^2$, $R^3$, $R^4$, and $R^5$ are each independently hydrogen, $C_{1-6}$ alkyl, aryl, arylalkyl, cycloalkyl, cycloheteroalkyl, heteroaryl, heteroarylalkyl, acylalkyloxycarbonyl, acyloxyalkyloxycarbonyl, acylalkyloxycarbonylamino, acyloxyalkyloxycarbonylamino, $C_{1-6}$ alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^2$, $R^3$, $R^4$, and $R^5$ can be substituted with the isotopes $^2H$ (deuterium), $^3H$ (tritium), $^{13}C$, $^{36}Cl$, $^{18}F$, $^{15}N$, $^{17}O$, $^{18}O$, $^{31}P$, $^{32}P$, and $^{35}S$; and "*" denotes a carbon capable of being optically active.

The compounds of the invention include both R and S compounds, and mixture of both R and S compounds.

In various aspects, the present disclosure provides pharmaceutical compositions comprising any one of the compounds of structural Formulae (I), (II), (III), (IV), (V), (VI), (VII), (VIII), (IX), (X), (XI), (XII), (XIII), (XIV), (XV), (XVI), or (XVII) and a pharmaceutically acceptable carrier, excipient, or diluent.

In various aspects, the present disclosure provides methods of treating or preventing obesity in a patient, the method comprising administering to a patient in need of such treatment an effective amount of any one of the compounds of structural Formulae (I), (II), (III), (IV), (V), (VI), (VII), (VIII), (IX), (X), (XI), (XII), (XIII), (XIV), (XV), (XVI), or (XVII). In certain aspects, the compound is selected from any one of structural Formulae (I), (II), (III), (IV), (V), (VI), (VII), (VIII), or (IX). In further aspects, the compound is selected from any one of the compounds of EXAMPLES 1-87. In further aspects, the method further comprises treating an obesity-related co-morbid symptom.

In various aspects, the present disclosure provides methods for treating or preventing depression in a patient, the method comprising administering to a patient in need of such treatment an effective amount of any one of the compounds of structural Formulae (I), (II), (III), (IV), (V), (VI), (VII), (VIII), (IX), (X), (XI), (XII), (XIII), (XIV), (XV), (XVI), or (XVII). In certain aspects, the compound is selected from any one of structural Formulae (I), (II), (X), (XI), (XII), (XIII), (XIV), (XV), (XVI), or (XVII). In further aspects, the compound is selected from any one of the compounds of EXAMPLES 1-87. In further aspects, the method further comprises treating a depression-related co-morbid symptom.

DETAILED DESCRIPTION

This invention provides compounds, pharmaceutical compositions and methods for pharmacological treatment of obesity and related co-morbid diseases and/or disorders and depression and co-morbid diseases and/or disorders. This invention also provides methods for synthesis of novel appetite suppressants. However, prior to describing this invention in further detail, the following terms will be first defined.
Definitions Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art. The compositions and formulations described herein can be practiced employing the pharmaceutically acceptable excipients and salts available in *Remington's Pharmaceutical Sciences*, $18^{th}$ Edition (Easton, Pa.: Mack Publishing Company, 1990).

"Compounds of the invention" refers to compounds encompassed by structural Formulae (I) disclosed herein. The compounds of the invention can be identified either by their chemical structure and/or chemical name. When the chemical structure and chemical name conflict, the chemical structures is determinative of the identity of the compound. The compounds of the invention may contain one or more chiral centers and/or double bonds and therefore, may exist as stereoisomers, such as double-bond isomers (i.e., geometric isomers), enantiomers or diastereoisomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass of conventionally found in nature. Examples of isotopes that may be incorporated into the compounds of the invention include, but are not limited to $^2H$, $^3H$, $^{13}C$, $^{15}N$, $^{18}O$, $^{17}O$, $^{31}P$, $^{32}P$, $^{35}S$, $^{18}F$ and a $^{36}Cl$. Further, it should be understood, when partial structures of the compounds of the invention are illustrated, that brackets of dashes indicate the point of attachment of the partial structure to the rest of the molecule.

"Composition of the invention" refers to at least one compound of the invention and a pharmaceutically acceptable vehicle, with which the compound is administered to a patient. When administered to a patient, the compounds of the invention are administered is isolated form, which means separated from a synthetic organic reaction mixture.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to methyl; ethyls such as ethanyl, ethenyl, ethynyl; propyls such as propan-1-yl, propan-2yl, cyclopropan-1-yl, prop-1-en-1-yl, prop-1-en-2-yl, prop-2-en-1-yl (allyl), cycloprop-1-en-1yl, cycloprop-2-en-1yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "$C_{1-6}$ alkyl" encompasses $C_1$ alkyl, $C_2$ alkyl, $C_3$ alkyl, $C_4$ alkyl, $C_5$ alkyl, $C_6$ alkyl, and any sub-range thereof.

The term "alkyl" specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl," are used. Preferably, an alkyl group comprises from 1-20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien 1-yl, etc.; and the like.

"Alkylene" refers to a divalent radical that is a branched or unbranched hydrocarbon fragment containing the specified number of carbon atoms, and having two points of attachment. Alkylenes are optionally substituted with one, two or three substituents. The term "$C_{1-6}$ alkylene" encompasses $C_1$ alkylene, $C_2$ alkylene, $C_3$ alkylene, $C_4$ alkylene, $C_5$ alkylene, $C_6$ alkylene, and any sub-range thereof. Examples of alkylenes include without limitation: methylene (—$CH_2$—, a $C_1$ alkylene), ethylene (—$CH_2CH_2$—, a $C_2$ alkylene), propylene (—$CH_2CH_2CH_2$—, a $C_3$ alkylene), and butylene (—$CH_2CH_2CH_2CH_2$—, a $C_4$ alkylene).

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl and the like.

"Acyloxyalkyloxycarbonyl" refers to a radical —C(O)OR'R"OC(O)R''', where R', R", and R''' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$OC(O)CH$_3$, —C(O)OCH$_2$OC(O)CH$_2$CH$_3$, —C(O)OCH(CH$_3$)OC(O)CH$_2$CH$_3$, —C(O)OCH(CH$_3$)OC(O)C$_6$H$_5$ and the like.

"Acylalkyloxycarbonyl" refers to a radical —C(O)OR'R"C(O)R''' where R', R", and R''' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$C(O)CH$_3$, —C(O)OCH$_2$C(O)CH$_2$CH$_3$, —C(O)OCH(CH$_3$)C(O)CH$_2$CH$_3$, —C(O)OCH(CH$_3$)C(O)C$_6$H$_5$ and the like.

"Acyloxyalkyloxycarbonylamino" refers to a radical —NRC(O)OR'R"OC(O)R''', where R, R', R", and R''' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$OC(O)CH$_3$, —NHC(O)OCH$_2$OC(O)CH$_2$CH$_3$, —NHC(O)OCH(CH$_3$)OC(O)CH$_2$CH$_3$, —NHC(O)OCH(CH$_3$)OC(O)C$_6$H$_5$ and the like.

"Acylalkyloxycarbonylamino" refers to a radical —NRC(O)OR'R"C(O)R''', where R, R', R", and R''' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$C(O)CH$_3$, —NHC(O)OCH$_2$C(O)CH$_2$CH$_3$, —NHC(O)OCH(CH$_3$)C(O)CH$_2$CH$_3$, —NHC(O)OCH(CH$_3$)C(O)C$_6$H$_5$ and the like.

"Acylamino" refers to "Amide" as defined herein.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted by one or more substituents as defined herein. Representative examples include, but are not limited to methoxy, ethoxy, propoxy, butoxy, cyclohexyloxy and the like.

"Alkoxycarbonyl" refers to a radical —C(O)-alkoxy where alkoxy is as defined herein.

"Alkoxycarbonylalkoxy" refers to a radical —OCR'R"C(O)-alkoxy where alkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_3$, —OCH$_2$C(O)OCH$_2$CH$_3$, —OCH(CH$_3$)C(O)OCH$_2$CH$_3$, —OCH(C$_6$H$_5$)C(O)OCH$_2$CH$_3$, —OCH(CH$_2$C$_6$H$_5$)C(O)OCH$_2$CH$_3$, —OC(CH$_3$)(CH$_3$)C(O)OCH$_2$CH$_3$, and the like.

"Alkoxycarbonylalkylamino" refers to a radical —NRCR'R"C(O)-alkoxy where alkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_3$, —N(CH$_3$)CH$_2$C(O)OCH$_2$CH$_3$, —NHCH(CH$_3$)C(O)OCH$_2$CH$_3$, —NHCH(C$_6$H$_5$)C(O)OCH$_2$CH$_3$, —NHCH(CH$_2$C$_6$H$_5$)C(O)OCH$_2$CH$_3$, —NHC(CH$_3$)(CH$_3$)C(O)OCH$_2$CH$_3$, and the like.

"Alkylsulfonyl" refers to a radical —S(O)$_2$R where R is an alkyl, or cycloalkyl group as defined herein that may be optionally substituted by one or more substituents as defined herein. Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined herein that may be optionally substituted by one or more substituents as defined herein. Representative examples include, but are not limited to methylthio, ethylthio, propylthio, butylthio, and the like.

"Amide or Acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, formylamino acetylamino, cyclohexylcarbonylamino, cyclohexylmethylcarbonyl-amino, benzoylamino, benzylcarbonylamino and the like.

"Amino" refers to the radical —$NH_2$

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene, and the like. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or $sp^3$ carbon atom, is replaced with an aryl group. Typically arylalkyl groups include, but not limited to, benzyl, 2-phenylethan-1-yl, 2-phenylethen-1-yl, naphthylmethyl, 2-naphthylethan-1-yl, 2-naphthylethene-1-yl, naphthobenzyl, 2-naphthophenylethan-1-yl and the like. Where specific alkyl moieties are intended, the nomenclature arylalkany, arylalkenyl and/or arylalkynyl is used. Preferably, an arylalkyl group is ($C_6$-$C_{30}$)arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylalkoxy" refers to an —O-arylalkyl radical where arylalkyl is as defined herein that may be optionally substituted by one or more substituents as defined herein.

"Arylalkoxycarbonylalkoxy" refers to a radical —OCR'R"C(O)-arylalkoxy where arylalkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —$OCH_2C(O)OCH_2C_6H_5$, —$OCH(CH_3)C(O)OCH_2C_6H_5$, —$OCH(C_6H_5)C(O)OCH_2C_6H_5$, —$OCH(CH_2C_6H_5)C(O)OCH_2C_6H_5$, —$OC(CH_3)(CH_3)C(O)OCH_2C_6H_5$, and the like.

"Arylalkoxycarbonylalkylamino" refers to a radical —NRCR'R"C(O)-arylalkoxy where arylalkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —$NHCH_2C(O)OCH_2C_6H_5$, —$N(CH_3)CH_2C(O)OCH_2C_6H_5$, —$NHCH(CH_3)C(O)OCH_2C_6H_5$, —$NHCH(C_6H_5)C(O)OCH_2C_6H_5$, —$NHCH(CH_2C_6H_5)C(O)OCH_2C_6H_5$, —$NHC(CH_3)(CH_3)C(O)OCH_2C_6H_5$, and the like.

"Aryloxycarbonyl" refers to radical —C(O)—O-aryl where aryl is defined herein that may be optionally substituted by one or more substituents as defined herein.

"Aryloxycarbonylalkoxy" refers to a radical —OCR'R"C(O)-aryloxy where aryloxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —$OCH_2C(O)OC_6H_5$, —$OCH(CH_3)C(O)OC_6H_5$, —$OCH(C_6H_5)C(O)OC_6H_5$, —$OCH(CH_2C_6H_5)C(O)OC_6H_5$, —$OC(CH_3)(CH_3)C(O)OC_6H_5$, and the like.

"Aryloxycarbonylalkylamino" refers to a radical —NRCR'R"C(O)-aryloxy where aryloxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —$NHCH_2C(O)OC_6H_5$, —$N(CH_3)CH_2C(O)OC_6H_5$, —$NHCH(CH_3)C(O)OC_6H_5$, —$NHCH(C_6H_5)C(O)OC_6H_5$, —$NHCH(CH_2C_6H_5)C(O)OC_6H_5$, —$NHC(CH_3)(CH_3)C(O)OC_6H_5$, and the like.

"Carbamoyl" refers to the radical –C(O)NRR where each R group is independently, hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methylcarbamate (—$NHC(O)OCH_3$), ethylcarbamate (—$NHC(O)OCH_2CH_3$), benzylcarbamate (—$NHC(O)OCH_2C_6H_5$), and the like.

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methyl carbonate (—$C(O)OCH_3$), cyclohexyl carbonate (—$C(O)OC_6H_{11}$), phenyl carbonate (—$C(O)OC_6H_5$), benzyl carbonate (—$C(O)OCH_2C_6H_5$), and the like.

"Carboxy" means the radical —C(O)OH.

"Cyano" means the radical —CN.

"Cycloalkyl" refers to a substituted or unsubstituted cylic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is ($C_3$-$C_{10}$) cycloalkyl, more preferably ($C_3$-$C_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkoxycarbonyl" refers to a radical —C(O)—OR where R is cycloheteroalkyl as defined herein that may be optionally substituted by one or more substituents as defined herein.

"Dialkylamino" means a radical —NRR' where R and R' independently represent an alkyl or cycloalkyl group as defined herein that may be optionally substituted by one or more substituents as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino, and the like.

"Derived from a drug" refers to a fragment that is structurally related to such a drug. The structure of the fragment is identical to the drug except where a hydrogen atom attached to a heteroatom (N or O) has been replaced with a covalent bond to another group (typically, a promoiety). Note that when a drug is a salt form of a carboxylic, phosphonic or phosphoric acid, the corresponding structural fragment derived from such a drug is considered to be derived from the protonated acid form.

"Drug" refers to a compound that exhibits therapeutic and/or prophylactic and/or diagnostic utility when administered in effective amounts to a patient or a mammal.

"Ester" refers to a radical —C(O)OR, where R is alkyl, substituted alkyl, cycloalkyl, substituted cycloalkyl, cycloheteroalkyl, substituted cycloheteroalkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl as defined herein that may be optionally substituted by one or more substituents as defined herein. Representative examples include, but are not limited to, methyl ester (—C(O)OCH$_3$), cyclohexyl ester (—C(O)OC$_6$H$_{11}$), phenyl ester (—C(O)OC$_6$H$_5$), benzyl ester (—C(O)OCH$_2$C$_6$H$_5$), and the like.

"Ether" refers to a radical —OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Halo" means fluoro, chloro, bromo, or iodo.

"Heteroalkoxy" means an —O-heteroalkyl radical where heteroalkyl is as defined herein that may be optionally substituted by one or more substituents as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to —O—, —S—, —O—O—, —S—S—, —OS—, —NR'—, =N—N=, —N=N—, —N=N—NR'—, —PH—, —P(O)$_2$—, —O—P(O)—, —S(O—, —S(O)$_2$—, —SnH$_2$—, and the like, wherein R' is hydrogen, alkyl, substituted alkyl, cycloalkyl, substituted cycloalkyl, aryl or substituted aryl that may be optionally substituted by one or more substituents as defined herein.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined that may be optionally substituted by one or more substituents as defined herein.

"Heteroarylalkyl" refers to an acyclic alkyl radical in which one of the hydrogen atoms bonded to a carbon atom, typically a terminal or sp3 carbon atom, is replaced with a heteroaryl group. Where specific alkyl moieties are intended, the nomenclature heteroarylalkanyl, heteroarylalkenyl and/or heteroarylalkynyl is used. Preferably, the heteroarylalkyl radical is a 6-30 carbon membered heteroarylalkyl, e.g., the alkanyl, alkenyl or alkynyl moiety of the heteroarylalkyl is 1-10 membered and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Hydroxy" means the radical —OH.

"Isomer" refers to compounds of the present invention that possess asymmetric carbon atoms (optical centers) or double bonds, the racemates, diastereomers, enantiomers, geometric isomers, structural isomers and individual isomers are all intended to be encompassed within the scope of the present invention.

"Oxo" means the divalent radical =O.

As used herein, the term "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, laurylsulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Phosphate" refers to a radical —OP(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Phosphonate" refers to a radical —P(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Preventing" or "Prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a group of atoms that when attached to a reactive group in a molecule masks, reduces or prevents that reactivity. Examples of protecting groups can be found in Green et al., "Protective Groups in Organic Chemistry", (Wiley, $2^{nd}$ ed. 1991) and Harrison et al., "Compendium of Synthetic Organic Methods", vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxy-carbonyl ("FMOC"), nitroveratryloxycarbonyl ("NVOC") and the like. Representative hydroxyl protecting groups include, but are not limited to, those where the hydroxyl group is either acylated or alkylated such as benzyl, and trialkylsilyl ethers and allyl ethers.

"Racemate" refers to an equimolar mixture of enantiomers of a chiral molecule.

"Spacer" refers to a $C_{1-6}$ alkylene in which one or more of the carbons of the $C_{1-6}$ alkylene can optionally be replaced with O, S, or $NR^6$, wherein $R^6$ can be H or $C_{1-6}$ alkyl. The $C_{1-6}$ alkylene is optionally substituted. In certain aspects, the $C_{1-6}$ alkylene is optionally substituted by acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonylalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide.

"Substituted" refers to a group in which one or more hydrogen atoms are each independently replaced with the same or different substituents(s). Typical substituents include, but are not limited to, —X, —$R^{54}$, —$O^-$, =O, —$OR^{54}$, —$SR^{54}$, —S, =S, —$NR^{54}R^{55}$, =$NR^{54}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2OR^{54}$, —$OS(O)_2O^{31}$, —$OS(O)_2R^{54}$, —$P(O)(O-)_2$, —$P(O)(OR^{14})(O^{31})$, —$OP(O)(OR^{54})(OR^{55})$, —$C(O)R^{54}$, —$C(O)OR^{54}$, —$C(O)NR^{54}R^{55}$, —$C(O)O^-$, —$C(S)OR^{54}$, —$NR^{56}C(O)NR^{54}R''$, —$NR^{56}C(S)NR^{54}R^{55}$, —$NR^{57}C(NR^{56})NR^{54}R^{55}$, and —$C(NR^{56})NR^{54}R^{55}$, where each X is independently a halogen; each $R^{54}$, $R^{55}$, $R^{56}$ and $R^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{58}R^{59}$, —$C(O)R^{58}$ or —$S(O)_2R^{58}$ or optionally $R^{58}$ and $R^{59}$ together with the atom to which they are both attached form a cycloheteroalkyl or substituted cycloheteroalkyl ring; and $R^{58}$ and $R^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR''')-piperazinyl or imidazolyl group wherein said group may be optionally substituted by one or more substituents as defined herein. R''' hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Thioether" refers to a radical —SR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and is severity and the age, weight, etc., of the patient to be treated, and can be determined by one of skill in the art without undue experimentation.

Reference now will be made in detail to preferred embodiments of the invention. While the invention will be described in conjunction with preferred embodiments, it will be understood that it is not intended to limit the invention to those preferred embodiments. To the contrary, it is intended to cover alternatives, modifications, and equivalents as may be included within the spirit and scope of the invention as defined by the appended claims.

Compounds of the Invention

The present disclosure provides cycloalkylmethylamine derivatives of structural Formulae (I) or (II):

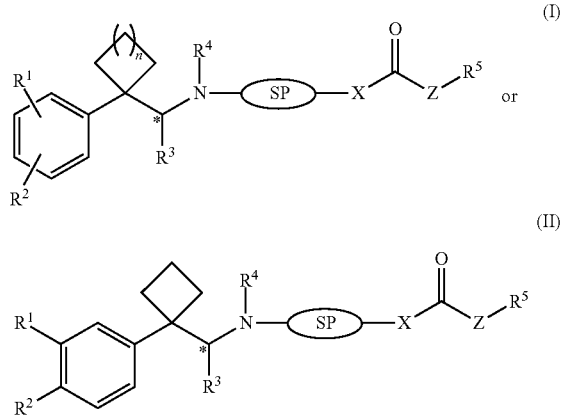

or isomer or pharmaceutically acceptable salt thereof, wherein:

n is 0, 1, 2, 3, 4, or 5;

SP is a spacer, wherein the spacer is $C_{1-6}$ alkylene, and wherein one or more of the carbons of the $C_{1-6}$ alkylene can optionally be replaced with O, S, or $NR^6$, wherein $R^6$ can be H or $C_{1-6}$ alkyl;

X is O, S, NH, $CH_2$, or alkylene;

Z is O, S, NH, $CH_2$, or a direct bond;

$R^1$, $R^2$, $R^3$, $R^4$, and $R^5$ are each independently hydrogen, $C_{1-6}$ alkyl, aryl, arylalkyl, cycloalkyl, cycloheteroalkyl, heteroaryl, heteroarylalkyl, acylalkyloxycarbonyl, acyloxyalkyloxycarbonyl, acylalkyloxycarbonylamino, acyloxyalkyloxycarbonylamino, $C_{1-6}$ alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^2$, $R^3$, $R^4$, and $R^5$ can be substituted with the isotopes $^2H$ (deuterium), 3H (tritium), 13C, 36Cl, 18F, 15N, 17O, 18O, 31P, 32P, and 35S; and "*" denotes a carbon capable of being optically active.

The compounds of the present disclosure include R isomers, S isomers, and mixtures of R and S isomers.

In certain aspects, the compound is of structural Formula (I):

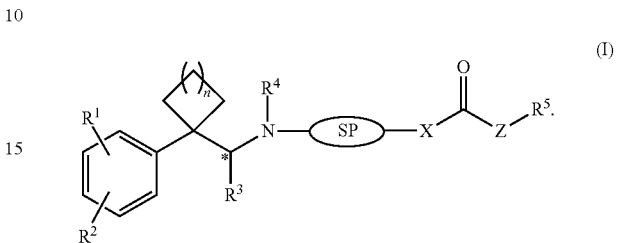

In certain aspects, the compound is of structural Formula (II):

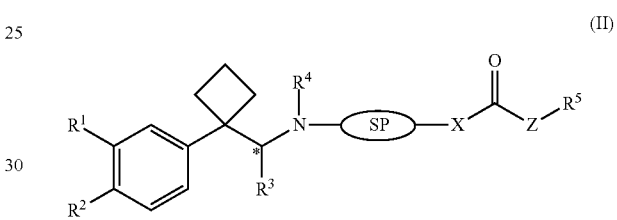

In certain aspects, n is 1; X is O, NH, or $CH_2$; Z is NH, O, or a direct bond; $R^1$ and $R^2$ are each independently hydrogen, halo, or $C_{1-6}$ alkoxy; $R^3$ is $C_{1-6}$ alkyl; and $R^4$ is hydrogen or $C_{1-6}$ alkyl.

In certain aspects, n is 1.

In certain aspects, the spacer is ethylene. In further aspects, the spacer is $C_{1-6}$ alkylene, and wherein one or more of the carbons of the $C_{1-6}$ alkylene is replaced with O, S, or $NR^6$. In certain aspects, one of the carbons in the $C_{1-6}$ alkylene is replaced with an O. In certain aspects, one of the carbons in the $C_{1-6}$ alkylene is replaced with an $NR^6$. In yet further aspects, the spacer is substituted. In some aspects, the spacer is substituted with $C_{1-6}$ alkyl or =O.

In certain aspects, X is O, NH, or $CH_2$. In further aspects, X is O. In further aspects, X is NH. In further aspects, X is $CH_2$.

In certain aspects, Z is NH, O, or a direct bond. In further aspects, Z is a direct bond. In further aspects, Z is O. In further aspects, Z is NH.

In certain aspects, $R^1$ is hydrogen, halo, or $C_{1-6}$ alkoxy. In certain aspects, $R^2$ is hydrogen, halo, or $C_{1-6}$ alkoxy. In further aspects, $R^1$ is halo and $R^2$ is halo. In further aspects, $R^1$ is Cl and $R^2$ is Cl. In further aspects, $R^1$ is hydrogen and $R^2$ is $C_{1-6}$ alkoxy. In further aspects, $R^1$ is hydrogen and $R^2$ is ethoxy. In further aspects, $R^1$ is hydrogen and $R^2$ is F. In further aspects, $R^1$ is F and $R^2$ is hydrogen.

In certain aspects, $R^3$ is $C_{1-6}$ alkyl, wherein one or more of the carbons of the $C_{1-6}$ alkyl can optionally be replaced with O. In further aspects, $R^3$ is hydrogen, methyl, ethyl, propyl, isopropyl, butyl, isobutyl, methoxy, or ethoxy. In further aspects, $R^3$ is isobutyl.

In certain aspects, $R^4$ is hydrogen or $C_{1-6}$ alkyl. In further aspects, $R^4$ is hydrogen.

In certain aspects, $R^5$ is hydrogen, $C_{1-6}$ alkyl, or $C_{1-6}$ alkoxy. In further aspects, $R^5$ is $C_{1-6}$ alkyl. In further aspects, $R^5$ is hydrogen, methyl, ethyl, propyl, isopropyl, butyl, isobutyl, or ethoxy.

In certain aspects, the present disclosure provides cycloalkylmethylamine derivatives of structural Formulae (III), (IV), (V), (VI), (VII), (VIII), or (IX):

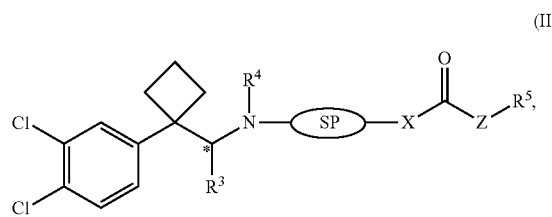
(III)

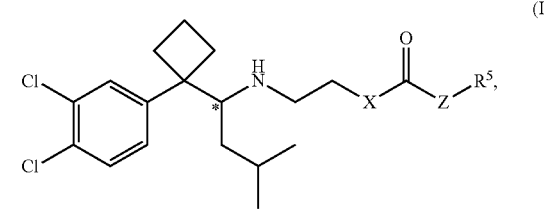
(IV)

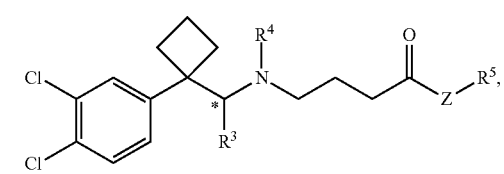
(V)

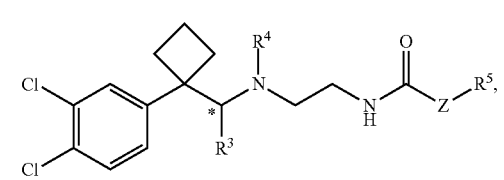
(VI)

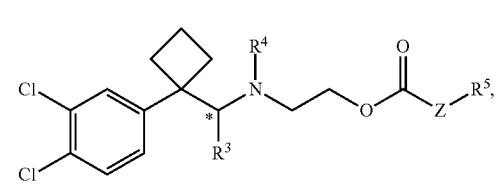
(VII)

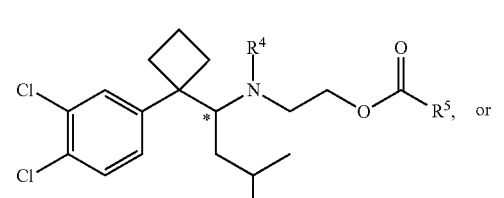
(VIII)

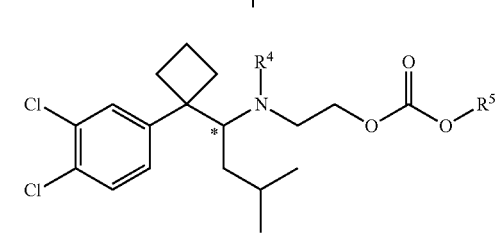
(IX)

or isomer or pharmaceutically acceptable salt thereof, wherein:

n is 0, 1, 2, 3, 4, or 5;

SP is a spacer, wherein the spacer is $C_{1-6}$ alkylene, and wherein one or more of the carbons of the $C_{1-6}$ alkylene can optionally be replaced with O, S, or $NR^6$, wherein $R^6$ can be H or $C_{1-6}$ alkyl;

X is O, S, NH, $CH_2$, or alkylene;

Z is O, S, NH, $CH_2$, or a direct bond;

$R^1$, $R^2$, $R^3$, $R^4$, and $R^5$ are each independently hydrogen, $C_{1-6}$ alkyl, aryl, arylalkyl, cycloalkyl, cycloheteroalkyl, heteroaryl, heteroarylalkyl, acylalkyloxycarbonyl, acyloxyalkyloxycarbonyl, acylalkyloxycarbonylamino, acyloxyalkyloxycarbonylamino, $C_{1-6}$ alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^2$, $R^3$, $R^4$, and $R^5$ can be substituted with the isotopes $^2H$ (deuterium), $^3H$ (tritium), $^{13}C$, $^{36}Cl$, $^{18}F$, $^{15}N$, $^{17}O$, $^{18}O$, $^{31}P$, $^{32}P$, and $^{35}S$; and "*" denotes a carbon capable of being optically active.

The compounds of the present disclosure include R isomers, S isomers, and mixtures of R and S isomers.

In certain aspects, the compound is of structural Formula (III):

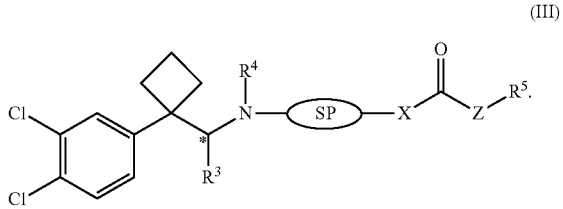
(III)

In certain aspects, the compound is of structural Formula (IV):

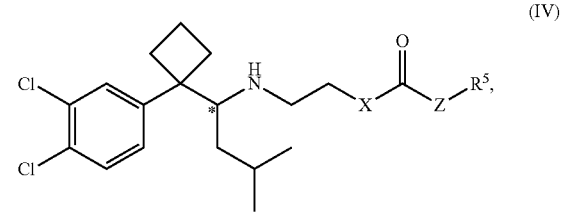
(IV)

In certain aspects, the compound is of structural Formula (V):

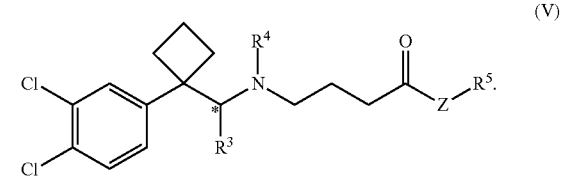
(V)

In certain aspects, the compound is of structural Formula (VI):

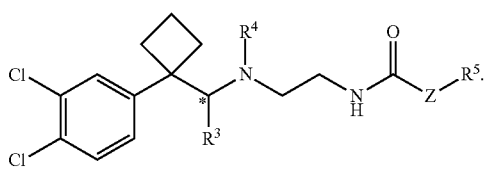

In certain aspects, the compound is of structural Formula (VII):

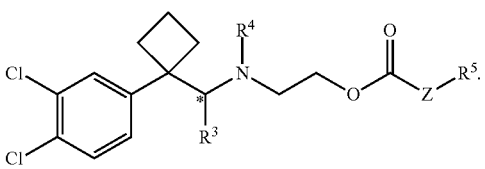

In certain aspects, the compound is of structural Formula Formula (VIII):

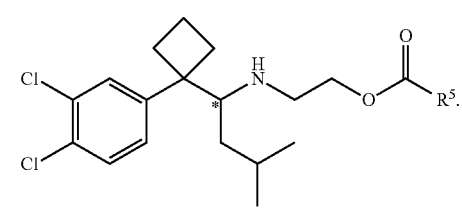

In certain aspects, the compound is of structural Formula (IX):

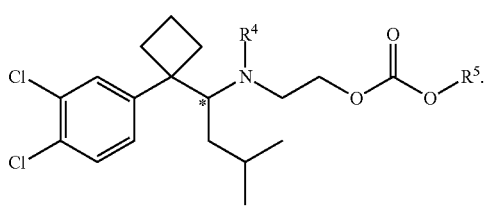

In certain aspects, n is 1; X is O, NH, or $CH_2$; Z is NH, O, or a direct bond; $R^1$ and $R^2$ are each independently hydrogen, halo, or $C_{1-6}$ alkoxy; $R^3$ is $C_{1-6}$ alkyl; and $R^4$ is hydrogen or $C_{1-6}$ alkyl.

In certain aspects, n is 1.

In certain aspects, the spacer is ethylene. In further aspects, the spacer is $C_{1-6}$ alkylene, and wherein one or more of the carbons of the $C_{1-6}$ alkylene is replaced with O, S, or $NR^6$. In certain aspects, one of the carbons in the $C_{1-6}$ alkylene is replaced with an O. In certain aspects, one of the carbons in the $C_{1-6}$ alkylene is replaced with an $NR^6$. In yet further aspects, the spacer is substituted. In some aspects, the spacer is substituted with $C_{1-6}$ alkyl or =O.

In certain aspects, X is O, NH, or $CH_2$. In further aspects, X is O. In further aspects, X is NH. In further aspects, X is $CH_2$.

In certain aspects, Z is NH, O, or a direct bond. In further aspects, Z is a direct bond. In further aspects, Z is O. In further aspects, Z is NH.

In certain aspects, $R^1$ is hydrogen, halo, or $C_{1-6}$ alkoxy. In certain aspects, $R^2$ is hydrogen, halo, or $C_{1-6}$ alkoxy. In further aspects, $R^1$ is halo and $R^2$ is halo. In further aspects, $R^1$ is Cl and $R^2$ is Cl. In further aspects, $R^1$ is hydrogen and $R^2$ is $C_{1-6}$ alkoxy. In further aspects, $R^1$ is hydrogen and $R^2$ is ethoxy. In further aspects, $R^1$ is hydrogen and $R^2$ is F. In further aspects, $R^1$ is F and $R^2$ is hydrogen.

In certain aspects, $R^3$ is $C_{1-6}$ alkyl, wherein one or more of the carbons of the $C_{1-6}$ alkyl can optionally be replaced with O. In further aspects, $R^3$ is hydrogen, methyl, ethyl, propyl, isopropyl, butyl, isobutyl, methoxy, or ethoxy. In further aspects, $R^3$ is isobutyl.

In certain aspects, $R^4$ is hydrogen or $C_{1-6}$ alkyl. In further aspects, $R^4$ is hydrogen.

In certain aspects, $R^5$ is hydrogen, $C_{1-6}$ alkyl, or $C_{1-6}$ alkoxy. In further aspects, $R^5$ is $C_{1-6}$ alkyl. In further aspects, $R^5$ is hydrogen, methyl, ethyl, propyl, isopropyl, butyl, isobutyl, or ethoxy.

In certain aspects, the present disclosure provides cycloalkylmethylamine derivatives of structural Formulae (X), (XI), (XII), (XIII), (XIV), (XV), (XVI), or (XVII):

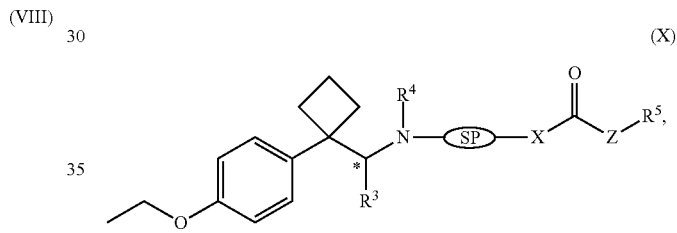

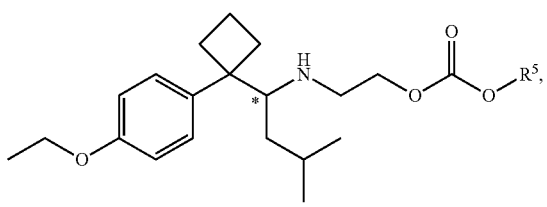

-continued

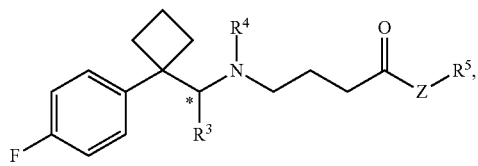
(XIV)

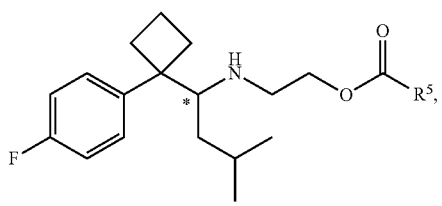
(XV)

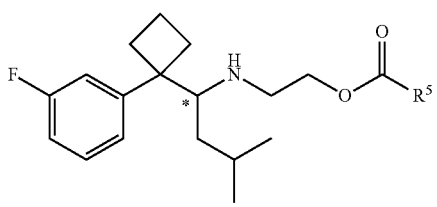
(XVI)

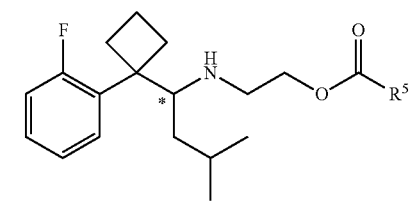
(XVII)

or isomer or pharmaceutically acceptable salt thereof, wherein:

n is 0, 1, 2, 3, 4, or 5;

SP is a spacer, wherein the spacer is $C_{1-6}$ alkylene, and wherein one or more of the carbons of the $C_{1-6}$ alkylene can optionally be replaced with O, S, or $NR^6$, wherein $R^6$ can be H or $C_{1-6}$ alkyl;

X is O, S, NH, $CH_2$, or alkylene;

Z is O, S, NH, $CH_2$, or a direct bond;

$R^1$, $R^2$, $R^3$, $R^4$, and $R^5$ are each independently hydrogen, $C_{1-6}$ alkyl, aryl, arylalkyl, cycloalkyl, cycloheteroalkyl, heteroaryl, heteroarylalkyl, acylalkyloxycarbonyl, acyloxyalkyloxycarbonyl, acylalkyloxycarbonylamino, acyloxyalkyloxycarbonylamino, $C_{1-6}$ alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^2$, $R^3$, $R^4$, and $R^5$ can be substituted with the isotopes $^2H$ (deuterium), $^3H$ (tritium), $^{13}C$, $^{36}Cl$, $^{18}F$, $^{15}N$, $^{17}O$, $^{18}O$, $^{31}P$, $^{32}P$, and $^{35}S$; and "*" denotes a carbon capable of being optically active.

The compounds of the present disclosure include R isomers, S isomers, and mixtures of R and S isomers.

In certain aspects, the compound is of structural Formula Formula (X):

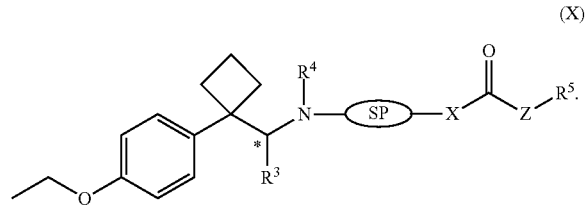
(X)

In certain aspects, the compound is of structural Formula (XI):

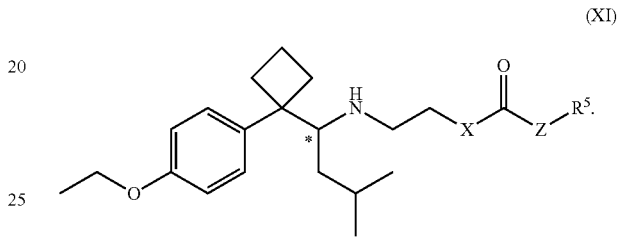
(XI)

In certain aspects, the compound is of structural Formula (XII):

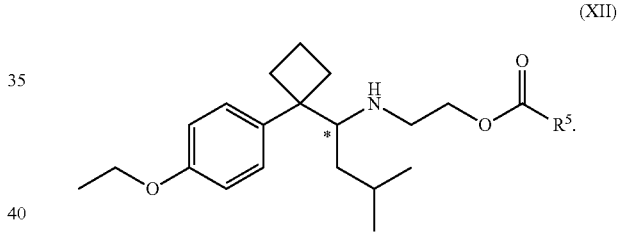
(XII)

In certain aspects, the compound is of structural Formula (XIII):

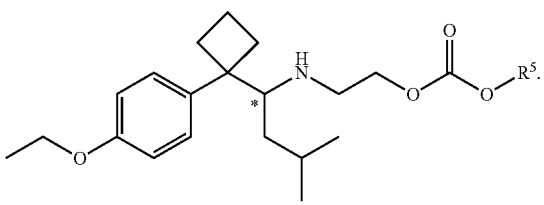
(XIII)

In certain aspects, the compound is of structural Formula (XIV):

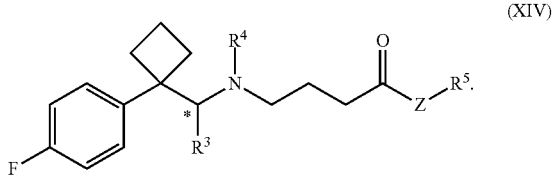
(XIV)

In certain aspects, the compound is of structural Formula (XV):

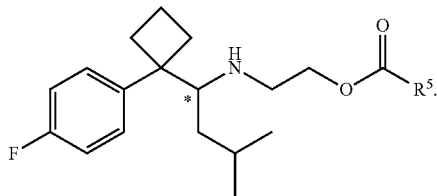

(XV)

In certain aspects, the compound is of structural Formula (XVI):

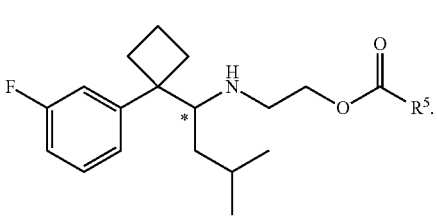

(XVI)

In certain aspects, the compound is of structural Formula (XVII):

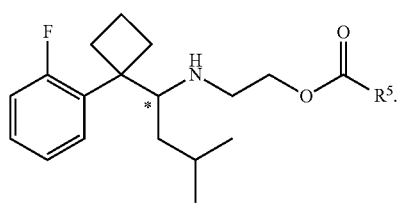

(XVII)

In certain aspects, n is 1; X is O, NH, or CH$_2$; Z is NH, O, or a direct bond; R$^1$ and R$^2$ are each independently hydrogen, halo, or C$_{1-6}$ alkoxy; R$^3$ is C$_{1-6}$ alkyl; and R$^4$ is hydrogen or C$_{1-6}$ alkyl.

In certain aspects, n is 1.

In certain aspects, the spacer is ethylene. In further aspects, the spacer is C$_{1-6}$ alkylene, and wherein one or more of the carbons of the C$_{1-6}$ alkylene is replaced with O, S, or NR$^6$. In certain aspects, one of the carbons in the C$_{1-6}$ alkylene is replaced with an O. In certain aspects, one of the carbons in the C$_{1-6}$ alkylene is replaced with an NR$^6$. In yet further aspects, the spacer is substituted. In some aspects, the spacer is substituted with C$_{1-6}$ alkyl or =O.

In certain aspects, X is O, NH, or CH$_2$. In further aspects, X is O. In further aspects, X is NH. In further aspects, X is CH$_2$.

In certain aspects, Z is NH, O, or a direct bond. In further aspects, Z is a direct bond. In further aspects, Z is O. In further aspects, Z is NH.

In certain aspects, R$^1$ hydrogen, halo, or C$_{1-6}$ alkoxy. In certain aspects, R is hydrogen, halo, or C$_{1-6}$ alkoxy. In further aspects, R$^1$ is halo and R$^2$ is halo. In further aspects, R$^1$ is Cl and R$^2$ is Cl. In further aspects, R$^1$ is hydrogen and R$^2$ is C$_{1-6}$ alkoxy. In further aspects, R$^1$ is hydrogen and R$^2$ is ethoxy. In further aspects, R$^1$ is hydrogen and R$^2$ is F. In further aspects, R$^1$ is F and R$^2$ is hydrogen.

In certain aspects, R$^3$ is C$_{1-6}$ alkyl, wherein one or more of the carbons of the C$_{1-6}$ alkyl can optionally be replaced with O. In further aspects, R$^3$ is hydrogen, methyl, ethyl, propyl, isopropyl, butyl, isobutyl, methoxy, or ethoxy. In further aspects, R$^3$ is isobutyl.

In certain aspects, R$^4$ is hydrogen or C$_{1-6}$ alkyl. In further aspects, R$^4$ is hydrogen.

In certain aspects, R$^5$ is hydrogen, C$_{1-6}$ alkyl, or C$_{1-6}$ alkoxy. In further aspects, R$^5$ is C$_{1-6}$ alkyl. In further aspects, R$^5$ is hydrogen, methyl, ethyl, propyl, isopropyl, butyl, isobutyl, or ethoxy.

The compounds of this invention described herein can have one or more of the following characteristics or properties:
1. Compounds of the invention can have dopamine transporter (DAT), norepinephrine transporter (NET) and serotonin transporter (SERT) inhibitory properties;
2. The primary metabolites, regardless of the electrophysiological properties of the parent drug, has, or have, negligible inhibitory activity at the IKr (HERG) channel at the normal therapeutic concentration of the parent drug in plasma (e.g. the concentration of the metabolite must be at least five times higher than the normal therapeutic concentration of the parent compound before activity at the IKr channel is observed);
3. Oral bioavailability of the compounds is consistent with oral administration using standard pharmacological oral formulations; however, the compounds, and compositions thereof, can also be administered using any delivery system that produces constant and controllable blood levels overt time.

In some embodiments, the subject invention provides compounds having any two or more of the above identified characteristics or properties. In a preferred embodiment the compounds of the invention have all four characteristics or properties.

Additional modifications of the compounds disclosed herein can readily be made by those skilled in the art. Thus, analogs and salts of the exemplified compounds are within the scope of the subject invention. With knowledge of the compounds of the subject invention skilled chemists can use known procedures to synthesize these compounds from available substrates. As used in this application, the term "derivatives" refers to compounds which are substantially the same as another compound but which may have been modified by, for example, adding additional side groups. The term "derivatives" as used in this application also may refer to compounds which are substantially the same as another compound but which have atomic or molecular substitution at certain locations in the compound.

The subject invention further pertains to enantiomerically isolated compounds, and compositions comprising the compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97% enantiomeric excess. In a most preferred embodiment, the compounds are in at least 99% or greater than 99% enantiomeric excess.

Synthesis of the Compounds of the Invention

The compounds of the invention can be obtained via the synthetic methods illustrated in Schemes 1. Several methods have been described in the art for the synthesis of cycloalkylmethylamine analogs (see, e.g. Mattson, R. J. et al. U.S. Pat.

No. 5,596,019; Lulla, A. et al., International Application Publication No. WO 2004/096202; Senanayake, C. H. et al., International Application Publication No. WO 02/083631; Vyas, S. K. et al., International Application Publication No. WO 02/36540; Jerussi, T. P. et al., International Application Publication No. WO 02/060424; Jeffery, J. E. et al., *J. Chem. Soc. Perkin Trans* 1, 1996, 2583-2589.). Other methods are known in the art for synthesizing cycloalkylmethylamines, which are readily accessible to the skilled artisan. The starting materials and intermediates used in the synthesis of target molecules (Scheme 1-4) thereof are commercially available or can be prepared by established procedures (See e.g., Green et al., "Protective Groups in Organic Synthesis," (Wiley, 4$^{rd}$ ed., 2006); Harrison et al "Compendium of Synthetic Organic Methods," vols. 1-8 (John Wiley and Sons, 1971-1996); "Beilstein Handbook of Organic Chemistry, Frankfurt, Germany; Feiser et al, "Reagents for Organic Synthesis," Volumes 1-45, Karger, 1991; March, Advanced Organic Chemistry," Wiley Interscience, 4$^{th}$ ed., 1992; Larock "Comprehensive Organic Transformations," Wiley-VCH Publishers, 2$^{nd}$ ed., 1999; Paquette, "Encyclopedia of Reagents for Organic Synthesis," John Wiley and Sons, 1$^{st}$ ed., 1995).

Accordingly, starting materials useful for preparing compounds of the invention and intermediates thereof are commercially available or can be prepared by well-known synthetic methods. Other methods for the synthesis of cycloalkylmethylamines described herein are either described in the art or will be readily apparent to the skilled artisan in view of the references provided above and may be used to synthesize the compounds of the invention. Accordingly, the methods presented in the Schemes herein are illustrative rather than comprehensive.

Methods

One general method for synthesis of compounds of Formulae (I) is described in Scheme 1. An appropriate substituted phenylacetonitrile (1) was reacted with dibromoalkane (2) in appropriate solvent (e.g., ether, THF, dioxane, DMF, DMSO) at a temperature between 10 and 100° C., preferably between 20 and 75° C. in the presence of a base (e.g., NaH, KOH) to give cycloalkylnitrile (3). The cycloalkylnitrile compounds were used to synthesize compounds (6) using a tandem Grignard-reduction method.

Scheme 1

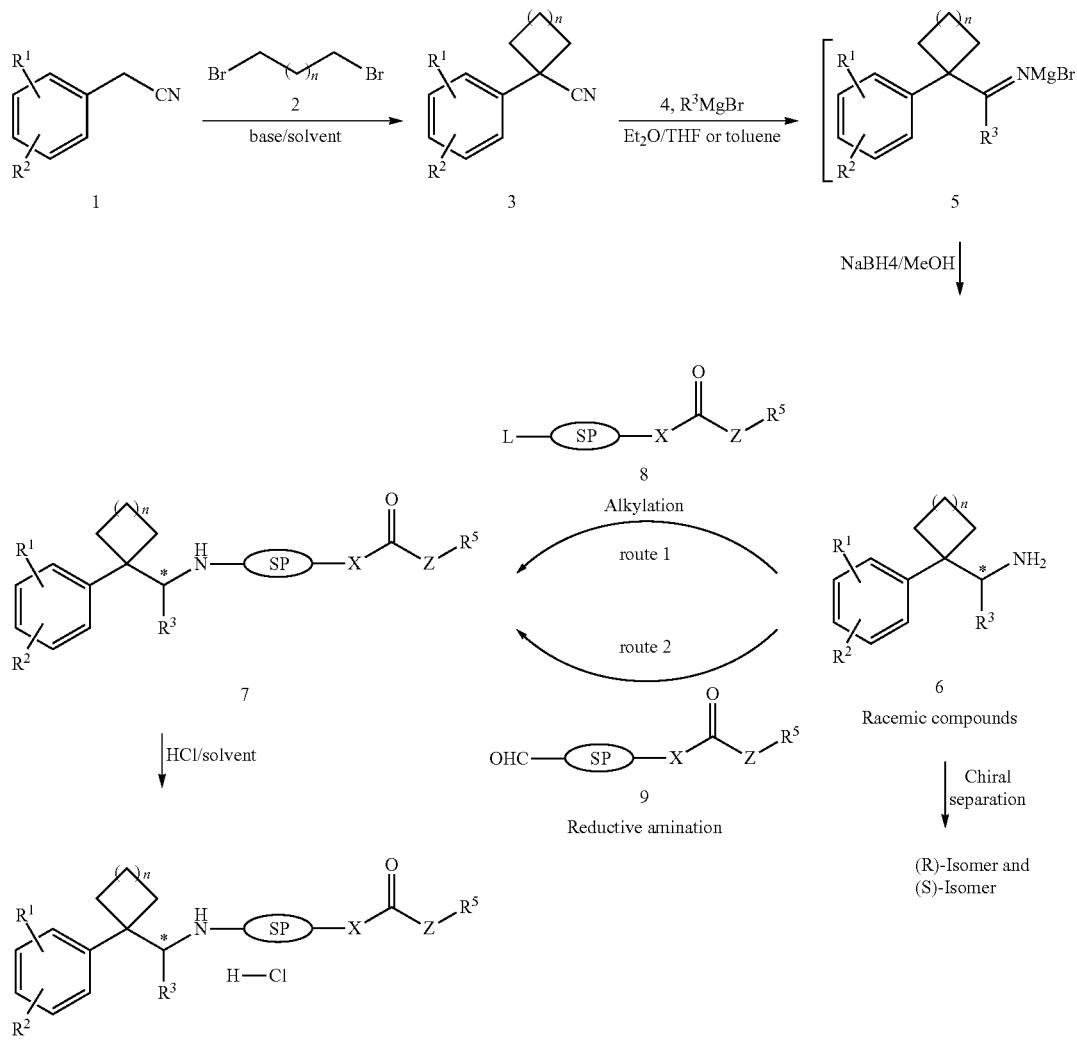

The typical procedure involves the reaction of a compound (3) with an appropriate Grignard reagent ($R^3MgBr$) in presence of toluene at a gentle reflux temperature at a for 10 to 24 hours. Then the resulting adduct was subjected to reduction without any workup procedures using reducing agent like sodium borohydride according to a standard or an established procedure (see, Jeffery et al., J. Chem. Soc., Perkin Trans. 1, 1996, 2583-2589) to produce the corresponding cycloalkylmethylamine (6). The selected racemic amine (6) was separated into corresponding optically pure (R)- and (S)-isomers by a standard chiral crystallization method using optically pure tartaric acid. The target cycloalkylmethylamine derivatives (7) were synthesized by alkylation of amines (6) with appropriate alkylating agents (8) or by reductive amination using appropriate aldehydes (9). The target compounds (7) were converted into corresponding hydrochloride salts (10) using hydrochloric acid (Scheme 1).

In one method cycloalkylmethylamine derivatives comprising Formula (I) was prepared as described in Scheme 2. The cycloalkylmethylamines (6) was alkylated with appropriate 4-nitrosulfonyl ester (18) at room temperature to get the corresponding cycloalkylmethylamine derivative (12) in moderato good yields. The compounds (12) were converted into hydrochloride salts by treating with 2N HCl solution in ether under standard conditions.

Scheme 2

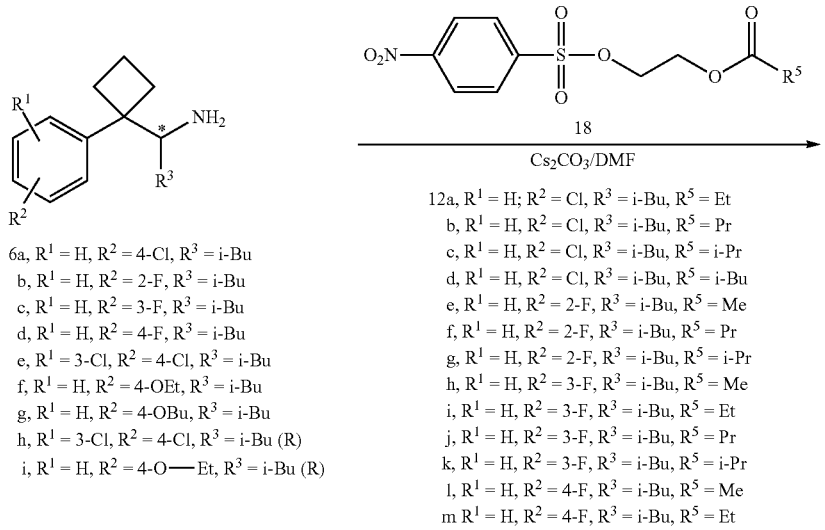

6a, $R^1$ = H, $R^2$ = 4-Cl, $R^3$ = i-Bu
b, $R^1$ = H, $R^2$ = 2-F, $R^3$ = i-Bu
c, $R^1$ = H, $R^2$ = 3-F, $R^3$ = i-Bu
d, $R^1$ = H, $R^2$ = 4-F, $R^3$ = i-Bu
e, $R^1$ = 3-Cl, $R^2$ = 4-Cl, $R^3$ = i-Bu
f, $R^1$ = H, $R^2$ = 4-OEt, $R^3$ = i-Bu
g, $R^1$ = H, $R^2$ = 4-OBu, $R^3$ = i-Bu
h, $R^1$ = 3-Cl, $R^2$ = 4-Cl, $R^3$ = i-Bu (R)
i, $R^1$ = H, $R^2$ = 4-O—Et, $R^3$ = i-Bu (R)

12a, $R^1$ = H; $R^2$ = Cl, $R^3$ = i-Bu, $R^5$ = Et
b, $R^1$ = H, $R^2$ = Cl, $R^3$ = i-Bu, $R^5$ = Pr
c, $R^1$ = H, $R^2$ = Cl, $R^3$ = i-Bu, $R^5$ = i-Pr
d, $R^1$ = H, $R^2$ = Cl, $R^3$ = i-Bu, $R^5$ = i-Bu
e, $R^1$ = H, $R^2$ = 2-F, $R^3$ = i-Bu, $R^5$ = Me
f, $R^1$ = H, $R^2$ = 2-F, $R^3$ = i-Bu, $R^5$ = Pr
g, $R^1$ = H, $R^2$ = 2-F, $R^3$ = i-Bu, $R^5$ = i-Pr
h, $R^1$ = H, $R^2$ = 3-F, $R^3$ = i-Bu, $R^5$ = Me
i, $R^1$ = H, $R^2$ = 3-F, $R^3$ = i-Bu, $R^5$ = Et
j, $R^1$ = H, $R^2$ = 3-F, $R^3$ = i-Bu, $R^5$ = Pr
k, $R^1$ = H, $R^2$ = 3-F, $R^3$ = i-Bu, $R^5$ = i-Pr
l, $R^1$ = H, $R^2$ = 4-F, $R^3$ = i-Bu, $R^5$ = Me
m $R^1$ = H, $R^2$ = 4-F, $R^3$ = i-Bu, $R^5$ = Et

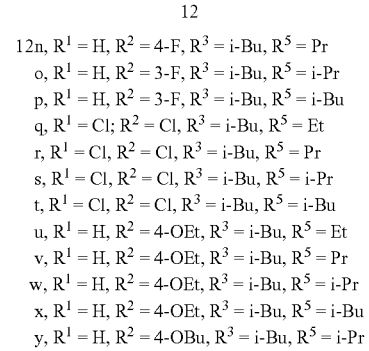

12

12n, $R^1$ = H, $R^2$ = 4-F, $R^3$ = i-Bu, $R^5$ = Pr
o, $R^1$ = H, $R^2$ = 3-F, $R^3$ = i-Bu, $R^5$ = i-Pr
p, $R^1$ = H, $R^2$ = 3-F, $R^3$ = i-Bu, $R^5$ = i-Bu
q, $R^1$ = Cl; $R^2$ = Cl, $R^3$ = i-Bu, $R^5$ = Et
r, $R^1$ = Cl, $R^2$ = Cl, $R^3$ = i-Bu, $R^5$ = Pr
s, $R^1$ = Cl, $R^2$ = Cl, $R^3$ = i-Bu, $R^5$ = i-Pr
t, $R^1$ = Cl, $R^2$ = Cl, $R^3$ = i-Bu, $R^5$ = i-Bu
u, $R^1$ = H, $R^2$ = 4-OEt, $R^3$ = i-Bu, $R^5$ = Et
v, $R^1$ = H, $R^2$ = 4-OEt, $R^3$ = i-Bu, $R^5$ = Pr
w, $R^1$ = H, $R^2$ = 4-OEt, $R^3$ = i-Bu, $R^5$ = i-Pr
x, $R^1$ = H, $R^2$ = 4-OEt, $R^3$ = i-Bu, $R^5$ = i-Bu
y, $R^1$ = H, $R^2$ = 4-OBu, $R^3$ = i-Bu, $R^5$ = i-Pr

The key building blocks (18) used in the synthesis of cycloalkylmethylamine derivatives were synthesized in two steps as illustrated in scheme 3. The carboxylic acids 14 were heated with ethylene glycol in presence of catalytic amounts of sulfuric acid to get the corresponding esters (16) in nearly quantitative yields. The ethylene glycol esters (16) were treated with 4-nitrosulfonyl chloride (17) in presence of a mild base triethylamine in dichloromethane at 0° C. to get the corresponding alkylating agent (18) in good yields.

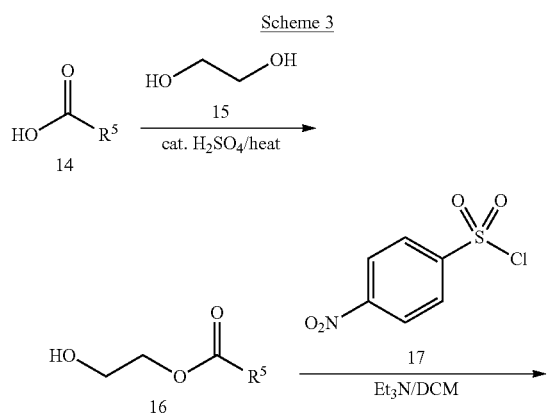

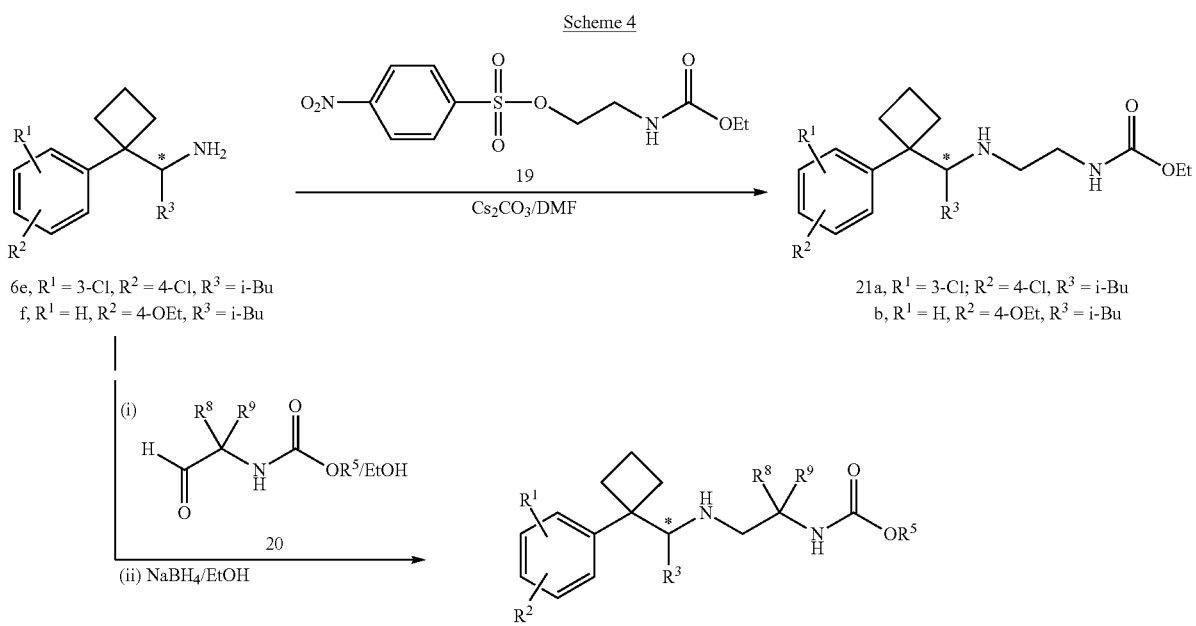

14, 16, 18a, $R^5$ = Et
c, $R^5$ = i-Pr

In another method cycloalkylmethylamine derivatives comprising Formula (I) was prepared as described in Scheme 4. The cycloalkylmethylamine 6 were alkylated with appropriate 4-nitrophenylsylfonyloxyethyl carbamate (19) as described for the synthesis cycloalkylmethylamine derivatives (12) in scheme 2 to get the corresponding carbamate derivatives (21) in moderate yields. The carbamate derivatives (21) were also prepared by reductive alkylation of amines (6) with appropriate aldehydes (20) under mild conditions in moderate to good yields (Scheme 4). The amine (6) was treated with aldehyde (2) in anhydrous methanol at room temperature for 15 hours followed by reacting with sodium borohydride (NaBH$_4$) at 0° C. to get the corresponding carbamate derivative of cycloalkylmethylamine (21). The selected optically pure (R)-cycloalkylmethylamine derivatives (21c-d) were also prepared from the corresponding optically pure (R)-cycloalkylmethylamines. The selected racemic carbamate derivatives (21) were subjected to chiral HPLC separation to get the corresponding optically pure (R)- and (S)-carbamates.

21a, $R^1$ = 3-Cl; $R^2$ = 4-Cl, $R^3$ = i-Bu, $R^5$ = Et, $R^8$ = $R^9$ = H, Racemic
b, $R^1$ = H, $R^2$ = 4-OEt, $R^3$ = i-Bu, $R^5$ = Et, $R^8$ = $R^9$ = H, Racemic
c, $R^1$ = 3-Cl; $R^2$ = 4-Cl, $R^3$ = i-Bu, $R^5$ = Et, $R^8$ = $R^9$ = H, (R)-Isomer
d, $R^1$ = H, $R^2$ = 4-OEt, $R^3$ = i-Bu, $R^5$ = Et, $R^8$ = $R^9$ = H, (R)-Isomer
e, $R^1$ = H, $R^2$ = 4-OEt, $R^3$ = i-Bu, $R^5$ = i-Pr, $R^8$ = $R^9$ = H, Racemic
f, $R^1$ = Cl, $R^2$ = Cl, $R^3$ = i-Bu, $R^5$ = i-Pr, $R^8$ = $R^9$ = H, Racemic
g, $R^1$ = Cl, $R^2$ = Cl, $R^3$ = i-Bu, $R^5$ = Et, $R^8$ = $R^9$ = Me, Racemic
h, $R^1$ = Cl, $R^2$ = Cl, $R^3$ = i-Bu, $R^5$ = i-Pr, $R^8$ = $R^9$ = Me, Racemic
i, $R^1$ = H, $R^2$ = 4-OEt, $R^3$ = i-Bu, $R^5$ = Et, $R^8$ = $R^9$ = Me, Racemic
j, $R^1$ = H, $R^2$ = 4-OEt, $R^3$ = i-Bu, $R^5$ = i-Pr, $R^8$ = $R^9$ = Me, Racemic The starting building block 4-nitrosulfoxyethanolamine carbamates (19) were prepared as illustrated in scheme 5. N-hydroxysuccinimide was reacted with appropriate alkyl chloroformate (22) followed by ethanolamine to get the carbamate derivatives 24. The carbamates 24 were treated with 4-nitrosulfonyl chloride in presence of triethylamine in dichloromethane to get the corresponding building block carbamates 19 in moderate to good yields.

Scheme 5

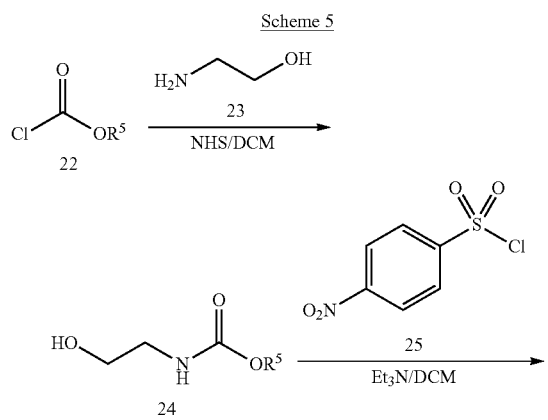

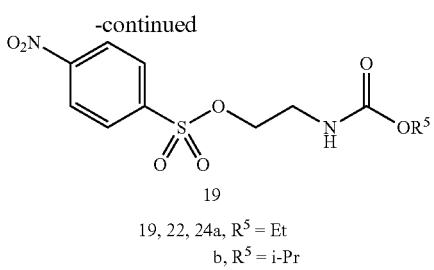

19, 22, 24a, $R^5$ = Et
b, $R^5$ = i-Pr

Similarly, the aldehyde building blocks (20) used in the preparation of (21) were prepared as illustrated in the scheme 6. The carbamates 27 were prepared under identical reaction conditions described for carbamates 24 in scheme 5. The carbamates were oxidized under mild conditions using commercially available oxidizing agents such as pyridine sulfur trioxide, pyridinium chlorochromate (PCC) or Swem oxidation conditions to get the corresponding aldehydes 20. The unsubstituted carbamate 29b-c were aso prepared from aminoacetaldehyde diethyl acetal (28). The carbamate derivatives of acetal 28 were prepared by reacting with appropriate chloroformate 22 under identical conditions described for the carbamates 27 in good yields. The carbamate derivatives 29 were treated with 2N hydrochloric acid in ether to get the corresponding aldehyde 20.

Scheme 6

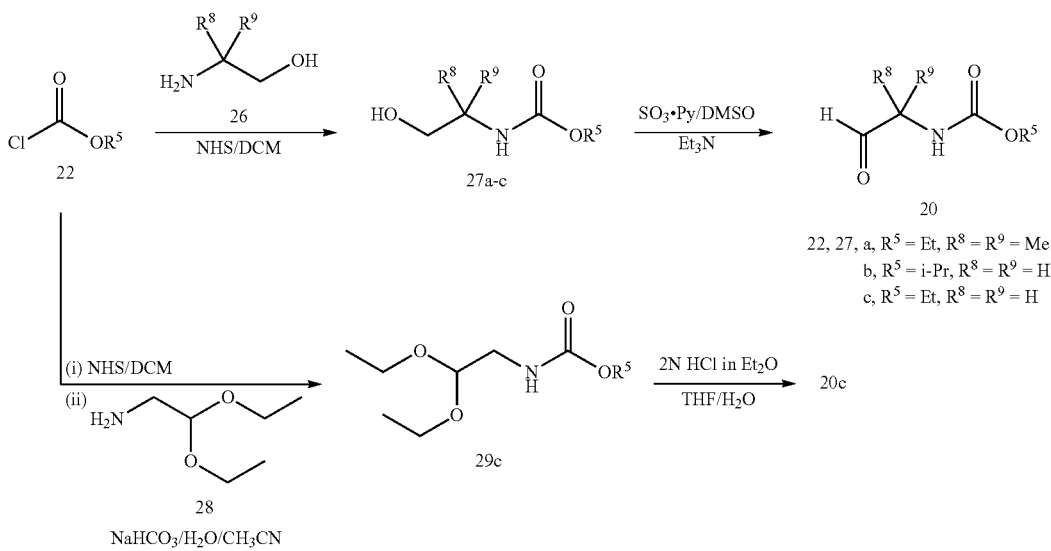

22, 27, a, $R^5$ = Et, $R^8$ = $R^9$ = Me
b, $R^5$ = i-Pr, $R^8$ = $R^9$ = H
c, $R^5$ = Et, $R^8$ = $R^9$ = H

In another method cycloalkylmethylamine derivatives comprising Formula (I) was prepared as described in Scheme 7. The amide derivatives (31) of cycloalkylmethylamines 6 were synthesized from aldehydes 30 under identical reductive amination conditions described for carbamate derivatives (21a-c) in scheme 4 in good yields. The racemic amide derivatives (31a-b) were subjected to chiral HPLC separation to get the corresponding optically pure (R)- and (S)-amides.

Scheme 7

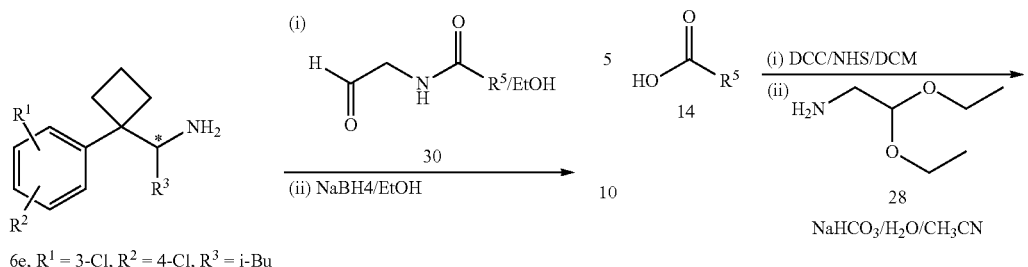

6e, R¹ = 3-Cl, R² = 4-Cl, R³ = i-Bu
f, R¹ = H, R² = 4-OEt, R³ = i-Bu

31a, R¹ = 3-Cl; R² = 4-Cl, R³ = i-Bu, R⁵ = Pr
b, R¹ = H, R² = 4-OEt, R³ = i-Bu, R⁵ = Pr

The amide building blocks used in the synthesis of cycloalkylmethylamine derivatives 31a-b were prepared as illustrated in scheme 8. The appropriate carboxylic acids 14 were coupled with aminoacetaldehyde diethyl acetal under standard coupling conditions using N,N-dicyclohexylcarbodiimide (DCC) and N-hydroxysuccinimide (NHS) in dichloromethane. The amides 33 were treated with trifluro acetic acid (TFA) in dichloromethane (DCM) at room temperature to get the corresponding aldehyde building blocks 30.

Scheme 8

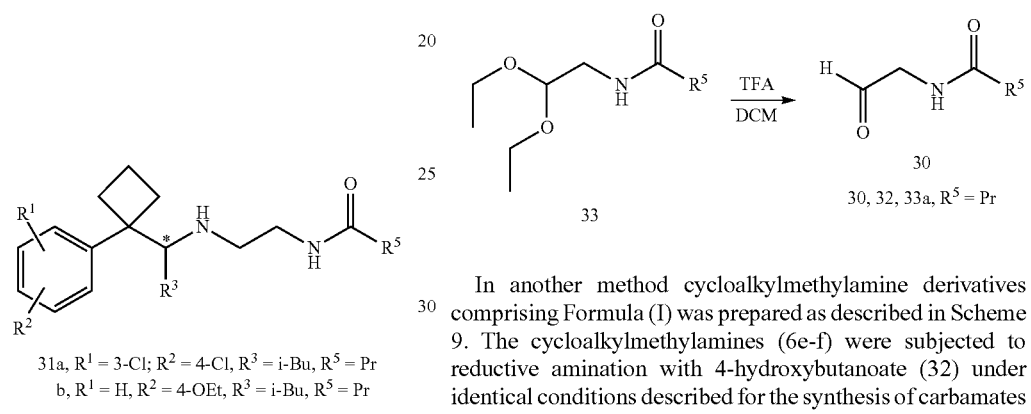

30, 32, 33a, R⁵ = Pr

In another method cycloalkylmethylamine derivatives comprising Formula (I) was prepared as described in Scheme 9. The cycloalkylmethylamines (6e-f) were subjected to reductive amination with 4-hydroxybutanoate (32) under identical conditions described for the synthesis of carbamates (21a-j) in scheme 4 and amides (31a-b) in scheme 7 to get the corresponding esters (13a-b) in good yields. The esters (13a-b) were treated with ammonia solution in methanol to get the corresponding amide derivative (33a-b) in good yields. The substituted amides 33c-j were synthesized by reacting esters (13a-b) with an appropriate amine in presence of trimethylaluminum (AlMe₃) in toluene as illustrated in scheme 9. The selected racemic amide derivatives (33) were subjected to chiral HPLC separation to get the corresponding optically pure (R)- and (S)-amides.

Scheme 9

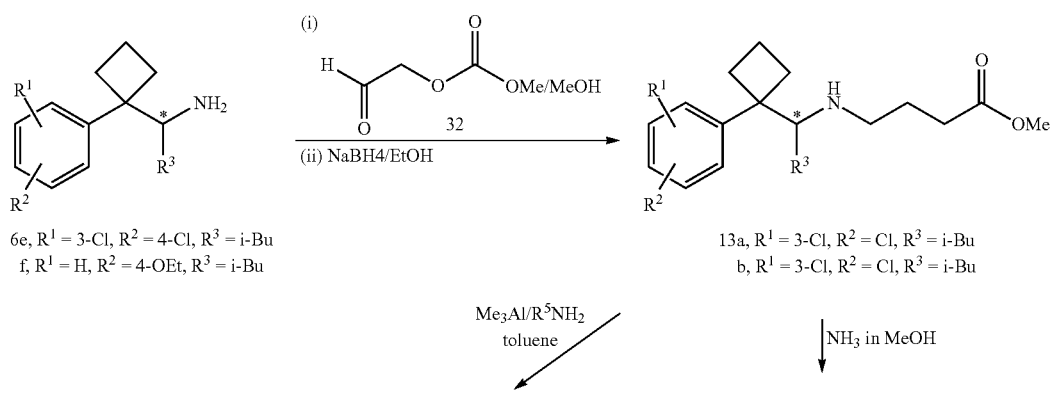

6e, R¹ = 3-Cl, R² = 4-Cl, R³ = i-Bu
f, R¹ = H, R² = 4-OEt, R³ = i-Bu

13a, R¹ = 3-Cl, R² = Cl, R³ = i-Bu
b, R¹ = 3-Cl, R² = Cl, R³ = i-Bu

Me₃Al/R⁵NH₂
toluene

NH₃ in MeOH

-continued

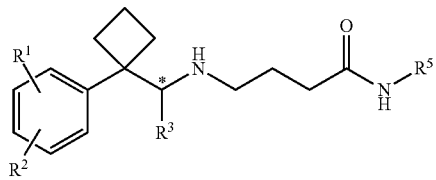

33c, R¹ = 3-Cl; R² = 4-Cl, R³ = i-Bu, R⁵ = Me
d, R¹ = 3-Cl; R² = 4-Cl, R³ = i-Bu, R⁵ = Et
e, R¹ = 3-Cl; R² = 4-Cl, R³ = i-Bu, R⁵ = Pr
f, R¹ = 3-Cl; R² = 4-Cl, R³ = i-Bu, R⁵ = i-Pr
g, R¹ = H; R² = 4-OEt, R³ = i-Bu, R⁵ = Me
h, R¹ = H; R² = 4-OEt, R³ = i-Bu, R⁵ = Et
i, R¹ = H; R² = 4-OEt, R³ = i-Bu, R⁵ = Pr
j, R¹ = H; R² = 4-OEt, R³ = i-Bu, R⁵ = i-Pr

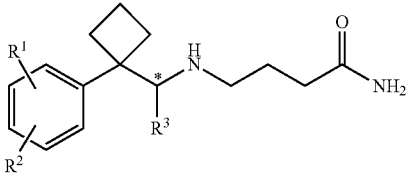

33a, R¹ = 3-Cl; R² = 4-Cl, R³ = i-Bu
b, R¹ = H, R² = 4-OEt, R³ = i-Bu

In another method cycloalkylmethylamine derivatives comprising Formula (I) was prepared as described in Scheme 10. The carbonate derivatives (35a-c) of cycloalkylamines (6e-f) were synthesized from aldehydes (34) using reductive amination conditions as described for the synthesis of carbamates (21a-j) in scheme 4 and amides (31a-b) in scheme 7.

Scheme 10

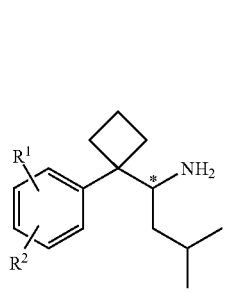

6e, R¹ = 3-Cl,
    R² = 4-Cl, R³ = i-Bu
f, R¹ = H,
    R² = 4-OEt, R³ = i-Bu

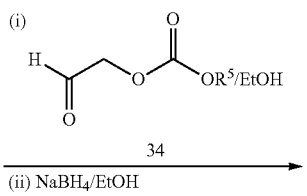

(ii) NaBH₄/EtOH

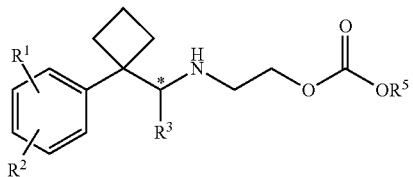

34, 35a, R¹ = 3-Cl; R² = 4-Cl, R³ = i-Bu, R⁵ = i-Pr
b, R¹ = H; R² = 4-OEt, R³ = i-Bu, R⁵ = i-Pr
c, R¹ = H; R² = 4-OBu, R³ = i-Bu, R⁵ = Et

The aldehyde building blocks (34) used in the synthesis of the target carbonate derivatives (35a-c) were prepared in two steps as illustrated in scheme 11. Ethylene glycol was reacted with appropriate chloroformate (36) in presence of pyridine in dichloromethane to get carbonates (38) in good yields. The carbonates (38) were oxidized under mild conditions using pyridine sulfurtrioxide in presence of triethylamine to get the corresponding aldehydes (34a-b).

Scheme 11

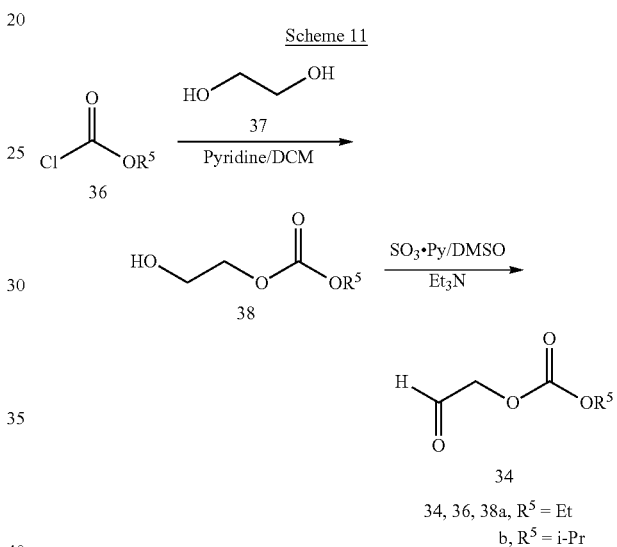

34, 36, 38a, R⁵ = Et
        b, R⁵ = i-Pr

Therapeutic Uses of Compounds of Structural Formulae

In various aspects, the present disclosure provides methods of treating or preventing obesity in a patient, the method comprising administering to a patient in need of such treatment an effective amount of any one of the compounds of structural Formulae (I), (II), (III), (IV), (V), (VI), (VII), (VIII), (IX), (X), (XI), (XII), (XIII), (XIV), (XV), (XVI), or (XVII). In certain aspects, the compound is selected from any one of structural Formulae (I), (II), (III), (IV), (V), (VI), (VII), (VIII), or (IX). In further aspects, the compound is selected from any one of the compounds of EXAMPLES 1-87. In further aspects, the method further comprises treating an obesity-related co-morbid symptom.

The present invention provides methods of treating and preventing obesity and associated co-morbid conditions. The term "co-morbid conditions associated with obesity" used in this document means medical conditions known to those skilled in the art to be associated with obesity. The term includes but not limited to the following: diabetes including non-insulin dependent diabetes mellitus, impaired glucose tolerance, hypertension, coronary thrombosis, stroke, depression, anxiety, psychoses (for example schizophrenia), tardive dyskinesia, drug addiction, drug abuse, cognitive disorders, Alzheimer's disease, cerebral ischaemia, obsessive-compulsive behavior, panic attacks, social phobias, eating disorders such as bulimia, anorexia, snacking and binge eating, lipid syndromes, hyperglycemia, hyperlipidemia, and stress in mammals particularly humans.

In addition, the compounds, compositions, and methods of the present invention can be used in the treatment or prevention of metabolic diseases and conditions arising therefrom, or for example non exercise activity thermogenesis and increased metabolic rate, sexual dysfunction, sleep apnoea, premenstrual syndrome, urinary incontinence including stress incontinence, hyperactivity disorders, hiatial hernia, and reflux esophagitis, pain, especially neuropathic pain, weight gain associated with drug treatment, chronic fatigue syndrome, osteoarthritis and gout, cancers associated with weight gain, menstrual dysfunction, gallstones, orthostatic hypotension and pulmonary hypertension.

The compounds, compositions, and methods of the present invention can be useful in preventing cardiovascular disease, and in reducing platelet adhesiveness, in aiding weight loss after pregnancy, reducing the craving to smoke and in aiding weight loss after smoking cessation. The present invention can also be useful in lowering uric acid levels and lipid levels in mammals particularly humans.

In accordance with the invention, a compound and/or a composition containing a compound of structural Formula (I) is administered to a patient, preferably a human, suffering from obesity and associated with co-morbid diseases and/or disorders Further, in certain embodiments, the compounds and/or compositions of the invention are administered to a patient, preferably a human, as a preventive measure against various diseases or disorders. Thus, the compounds and/or compositions containing compound(s) of structural Formula (I) may be administered as a preventive measure to a patient having a predisposition for obesity and associated co-morbid diseases and/or disorders (see, Montana, J. G. International Application Publication No. WO 2004/058237; Lulla, A. et al., International Application Publication No. WO 2004/096202; Jerussi, T. P. et al., International Application Publication No. WO 02/060424; Senanayake, C. H. et al., International Application Publication No. WO 01/51453; Heal, D. J. International Application Publication No. WO 01/00205; Birch, A. M. et al., International Application Publication No. WO 01/00187; Mueller, P. International Application Publication No. WO 00/32178; Bailey, C. International Application Publication No. WO 98/11884; Kelly, P. International Application Publication No. WO 98/13034).

Thus, those of skill in the art may readily assay and use the compounds and/or compositions containing compound(s) of structural Formulae (I) to treat obesity and associated co-morbid diseases and/or disorders.

In various aspects, the present disclosure provides methods for treating or preventing depression in a patient, the method comprising administering to a patient in need of such treatment an effective amount of any one of the compounds of structural Formulae (I), (II), (III), (IV), (V), (VI), (VII), (VIII), (IX), (X), (XI), (XII), (XIII), (XIV), (XV), (XVI), or (XVII). In certain aspects, the compound is selected from any one of structural Formulae (I), (II), (X), (XI), (XII), (XIII), (XIV), (XV), (XVI), or (XVII). In further aspects, the compound is selected from any one of the compounds of EXAMPLES 1-87. In further aspects, the method further comprises treating a depression-related co-morbid symptom.
Therapeutic/Prophylactic Administration The compounds, and/or compositions containing compounds(s), of structural Formula (I) can be advantageously used in human medicine. As previously described in Section 4.4 above, compounds and compositions containing compound(s) of structural Formulae (I) are useful for the treatment or prevention of obesity and associated co-morbid diseases and/or disorders.

When used to treat or prevent the above disease or disorders compounds and/or compositions of the invention can be administered or applied singly, in combination with other agents. The compounds and/or compositions of the invention can also be administered or applied singly, in combination with other pharmaceutically active agents, including other compounds and/or compositions of the invention.

The current invention provides methods of treatment and prophylaxis by administration to a patient of a therapeutically effective amount of a composition and/or compound of the invention. The patient may be an animal, is more preferably a mammal, and most preferably a human.

The present compounds and/or compositions of the invention, which comprise one or more compounds and/or compositions of the invention are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin.

In particularly, preferred embodiments, the compounds and/or compositions of the invention can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In another embodiment, polymeric materials can be used (see "Medical Applications of Controlled Release," Langer and Wise (eds.), Wiley, New York (1984); Ranger and Peppas, 1983, J. Macromol. Sci. Rev. Macromol Chem. 23:61; see also Levy et al., 1985, Science 228:190; During et al., 1989, Ann Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described in the art (Bamba et al., Int. J. Pharm., 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems sold by Alza Corporation of Mountain View, Calif. are used for oral sustained release delivery devices (See for example, Theeuwes et al., U.S. Pat. No. 3,845,770; and Theeuwes et al, U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

The compounds, and/or compositions containing compound(s) of structural Formula (I) of the invention may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

Compositions of the Invention

In various aspects, the present disclosure provides pharmaceutical compositions comprising any one of the compounds of structural Formulae (I), (II), (III), (IV), (V), (VI), (VII), (VIII), (IX), (X), (XI), (XII), (XIII), (XIV), (XV), (XVI), or (XVII) and a pharmaceutically acceptable carrier, excipient, or diluent.

The present composition contain a therapeutically effective amount of one or more compounds of the invention, preferably in purified form, together with a suitable amount of a pharmaceutically acceptable vehicle, which so as to provide the form for proper administration to a patient. When administered to a patient, the compounds of the invention and pharmaceutically acceptable vehicles are preferably sterile. Water is preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making levigating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17$^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about mM to about 50 mM) etc. Additionally, flavoring agents, preservatives, coloring agents, bile salts, acylcarnitines and the like may be added.

Compositions for administration via other routes may also be contemplated. For buccal administration, the compositions may take the form of tablets, lozenzes, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Methods of Use and Doses

A compound of the invention, or compositions thereof, will generally be used in an amount effective to achieve the intended purpose. For use to treat or prevent obesity and associated co-morbid diseases and/or disorders the compounds of Formula (I) and compositions containing a compound of Formulae (I) are administered or applied in a therapeutically effective amount.

In various aspects, the present disclosure provides methods of treating or preventing obesity in a patient, the method comprising administering to a patient in need of such treatment an effective amount of any one of the compounds of structural Formulae (I), (II), (III), (IV), (V), (VI), (VII), (VIII), (IX), (X), (XI), (XII), (XIII), (XIV), (XV), (XVI), or (XVII). In certain aspects, the compound is selected from any one of structural Formulae (I), (II), (III), (IV), (V), (VI), (VII), (VIII), or (IX). In further aspects, the compound is selected from any one of the compounds of EXAMPLES 1-87. In further aspects, the method further comprises treating an obesity-related co-morbid symptom.

In various aspects, the present disclosure provides methods for treating or preventing depression in a patient, the method comprising administering to a patient in need of such treatment an effective amount of any one of the compounds of structural Formulae (I), (II), (III), (IV), (V), (VI), (VII), (VIII), (IX), (X), (XI), (XII), (XIII), (XIV), (XV), (XVI), or (XVII). In certain aspects, the compound is selected from any one of structural Formulae (I), (II), (X), (XI), (XII), (XIII), (XIV), (XV), (XVI), or (XVII). In further aspects, the compound is selected from any one of the compounds of EXAMPLES 1-87. In further aspects, the method further comprises treating a depression-related co-morbid symptom.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

The compounds and/or compositions containing compound(s), of structural Formulae (I) for the pharmacological treatment of obesity and related co-morbid indications may be administered in the range 0.1 mg to 500 mg preferably 1 mg to 100 mg per day given in one or more doses and more preferably 5 mg, 10 mg, 15 mg, 20 mg, 25 mg, 35 mg or 50 mg per day and most preferably 25 mg.

The compounds of the invention are preferably assayed in vitro and in vivo, for the desired therapeutic or prophylactic activity, prior to use in humans. The compounds of the invention may also be demonstrated to be effective and safe using animal model systems.

Preferably, the therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

Exemplary Aspects

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

Atm=Atmosphere
CDI=1,1'-Carbonyldiimidazole
DCM=dichloromethane
DMAP=4-N,N-dimethylaminopyridine
DMF=N,N-dimethylformamide
g=gram
h=hours
L=liter
LC/MS=liquid chromatography/mass spectroscopy
M=molar
mL=milliliter
mmol=millimols
nM=nanomolar
µM=micromolar
MTBE=methyl tert-butyl ether
rt=room temperature
TEA=triethylamine
THF=tetrahydrofuran
TFA=trifluoroacetic acid General Procedure for Synthesis of Compounds 6a-g (Scheme 1)

To a stirred solution of Grignard reagent (2M solution in ether, 0.065 mol) under nitrogen atmosphere was added drop wise a solution of phenylcyclobutanecarbonitrile (0.026 mol) in 50 mL of toluene at 0° C. Then the reaction mixture was slowly heated at 92° C. for 18 h. The progress of the reaction was monitored by thin layer chromatography (TLC). The reaction mixture was cooled to room temperature and concentrated under reduced pressure. The residue was diluted with 30 mL of anhydrous methanol and cooled down at 0° C., and NaBH$_4$ (2.5 g) was added slowly portion wise. The resulting mixture was stirred until complete conversion of imine intermediate to the corresponding amine. After the reaction was completed, methanol was removed by evaporation. The residue was diluted with ethyl acetate, washed with saturated sodium bicarbonate, dried over MgSO$_4$ and evaporated under reduce pressure to give corresponding phenylcyclobutylmethylamine 6 which was purified by column chromatography on silica gel using a gradient of hexane and ethyl acetate. The pure products 6a-g gave satisfactory 1H NMR and/or Mass spectral data.

EXAMPLE 1

1-(1-(4-Chlorophenyl)cyclobutyl)-3-methylbutan-1-amine (6a)

Colorless oil (4.7 g, 72%). $^1$HNMR (400 MHz, CDCl$_3$): δ 0.84 (d, J=6.8 Hz, 3H); 0.88 (d, J=6.8 Hz, 3H); 1.13-1.23 (m, 2H); 1.66-1.68 (m, 1H); 1.79-1.84 (m, 1H); 1.90-1.96 (m, 1H); 2.15-2.16 (m, 1H); 2.25-2.33 (m, 3H); 2.98 (d, J=10.8 Hz, 1H); 7.06 (dd, J=1.6; 8.4 Hz, 2H); 7.24 (dd, J=1.6; 8.4 Hz, 2H). MS (ESI): m/z=252.10 (M+H$^+$).

EXAMPLE 2

1-(1-(2-Fluorophenyl)cyclobutyl)-3-methylbutan-1-amine (6b)

Colorless oil (2.8 g, 70%). $^1$HNMR (400 MHz, CDCl$_3$): δ 0.54-0.61 (m, 1H); 0.84 (d, J=6.8 Hz, 3H); 0.88 (d, J=6.8 Hz, 3H); 1.14-1.24 (m, 1H); 1.66-1.70 (m, 1H); 1.79-1.82 (m, 1H); 1.92-1.99 (m, 1H); 2.13-2.18 (m, 1H); 2.26-2.37 (m, 3H); 2.97 (d, J=10.8 Hz, 1H); 6.96 (m, 2H); 7.08 (m, 2H). MS (ESI): m/z=236.2 (M+H$^+$).

EXAMPLE 3

1-(1-(3-Fluorophenyl)cyclobutyl)-3-methylbutan-1-amine (6c)

Colorless oil (2.2 g, 70%). $^1$HNMR (400 MHz, CDCl$_3$): δ 0.58-0.65 (m, 1H); 0.84 (d, J=6.8 Hz, 3H); 0.88 (d, J=6.8 Hz, 3H); 1.15-1.21 (m, 1H); 1.67-1.70 (m, 1H); 1.80-1.86 (m, 1H); 1.93-1.98 (m, 1H); 2.12-2.18 (m, 1H); 2.28-2.37 (m, 3H); 2.97 (dd, J=2.0 Hz; 10.8 Hz, 1H); 6.82-6.92 (m, 3H); 7.21-7.27 (m, 1H). MS (ESI): m/z=236.2 (M+H$^+$).

EXAMPLE 4

1-(1-(4-Fluorophenyl)cyclobutyl)-3-methylbutan-1-amine (6d)

Colorless oil (2.2 g, 70%). $^1$HNMR (400 MHz, CDCl$_3$): δ 0.58-0.65 (m, 1H); 0.84 (d, J=6.8 Hz, 3H); 0.88 (d, J=6.8 Hz, 3H); 1.15-1.21 (m, 1H); 1.67-1.70 (m, 1H); 1.80-1.86 (m, 1H); 1.93-1.98 (m, 1H); 2.12-2.18 (m, 1H); 2.28-2.37 (m, 3H); 2.97 (dd, J=2.0 Hz; 10.8 Hz, 1H); 6.93-7.08 (m, 3H); 7.12-7.16 (m, 1H). MS (ESI): m/z=236.2 (M+H$^+$).

EXAMPLE 5

1-(1-(3,4-Dichlorophenyl)cyclobutyl)-3-methylbutan-1-amine (6e)

Colorless oil (3.6 g, 70%). $^1$HNMR (400 MHz, CDCl$_3$): δ 0.53-0.60 (m, 1H); 0.84 (d, J=6.8 Hz, 3H); 0.88 (d, J=6.8 Hz, 3H); 1.10-1.13 (m, 1H); 1.63-1.67 (m, 1H); 1.77-1.83 (m, 1H); 1.91-1.97 (m, 1H); 2.12-2.16 (m, 1H); 2.21-2.33 (m, 3H); 2.97 (d, J=10.8 Hz, 1H); 6.96 (dd, J=2.0 Hz; 8.4 Hz, 1H); 7.19 (d, J=2 Hz; 1H); 7.32 (d, J=8.4 Hz, 1H). MS (ESI): m/z=287.20 (M+H$^+$).

EXAMPLE 6

1-(1-(4-Ethoxyphenyl)cyclobutyl)-3-methylbutan-1-amine (6f)

Colorless oil (1.06 g, 72%). $^1$HNMR (400 MHz, CDCl$_3$): δ 0.57-0.64 (m, 1H); 0.84 (d, J=6.8 Hz, 3H); 0.88 (d, J=6.8 Hz, 3H); 1.15-1.21 (m, 1H); 1.40 (t, J=6.8 Hz, 3H); 1.67-1.69 (m, 1H); 1.79-1.84 (m, 1H); 1.90-1.96 (m, 1H); 2.14-2.16 (m, 1H); 2.27-2.36 (m, 3H); 2.98 (dd, J=2.0 Hz; 10.8 Hz, 1H); 4.02 (q, J=6.8 Hz, 2H); 6.83 (d, J=8.4 Hz, 2H); 7.05 (d, J=8.4 Hz, 2H). MS (ESI): m/z=262.20 (M+H$^+$).

EXAMPLE 7

1-(1-(4-Buthoxyphenyl)cyclobutyl)-3-methylbutan-1-amine (6g)

Colorless oil (2.74 g, 73%). $^1$HNMR (400 MHz, CDCl$_3$): δ 0.56-0.63 (m, 1H); 0.84 (d, J=6.8 Hz, 3H); 0.88 (d, J=6.8 Hz, 3H); 0.95 (t, J=7.2 Hz, 3H); 1.09 (sbroad, 2H); 1.13-1.20 (m, 1H); 1.43-1.52 (m, 2H); 1.63-1.66 (m, 1H); 1.70-1.83 (m, 3H); 1.88-1.96 (m, 1H); 2.10-2.16 (m, 1H); 2.25-2.36 (m, 3H); 2.98 (dd, J=2.0 Hz; 10.8 Hz, 1H); 3.93 (t, J=6.4 Hz, 2H); 6.82 (d, J=8.4 Hz, 2H); 7.03 (d, J=8.4 Hz, 2H). MS (ESI): m/z=290.20 (M+H$^+$).

EXAMPLE 8

Procedure for Preparation of Optically Pure Cycloalkylmethylamines 6h-i

The optical pure (R)-isomers of 6h-i were prepared from the corresponding racemic 6e-g by standard chiral separation method using crystallization technique.

(R)-1-(1-(3,4-Dichlorophenyl)cyclobutyl)-3-methylbutan-1-amine (h)

A mixture of racemic didesmethylsibutramine (7 g, 0.024 mol) and toluene (70 mL) was heated to 70-80° C. and (D)-tartaric acid (3.67 g, 0.024 mol) in water (7 mL) and acetone (3.5 mL) was added slowly. The resulting mixture was refluxed for 30 minutes, after which the water and acetone were removed by distillation. The resulting mixture was cooled to room temperature to provide slurry which was then filtered. The resulting wet cake was washed two times with MTBE (7 mL×2) and dried to yield (R/S)-DDMS.(D)-TA isolated as an off-white solid (10.72 g, 100%). The (R)-complex complex was submitted to further resolution.

The mixture of (R)-DDMS.(D)-TA (10.72 g) and acetone/water/ethanol (107 mL:14.4 mL:7 mL) was refluxed (90° C.) for 1 hour. The mixture was then cooled to room temperature and the resulting slurry was filtered and dried to give (R)-DDMS.(D)-TA isolated as a white solid (3.28 g, 31%). expected ee: 92%. The (R)-compless was submitted to further resolution.

The mixture of (R)-DDMS.(D)-TA (3.28 g, ~92% ee) and acetonitrile/water/ethanol (39.36 mL:8.52 mL:3.9 mL) was refluxed (90° C.) for 1 hour. The mixture was then cooled to room temperature and the resulting slurry was filtered and dried to give (R)-DDMS.(D)-TA isolated as a white solid (2.8 g, 85%). Expected ee 99.7%. The mixture was submitted to decomplxation The mixture of (R)-DDMS.(D)-TA (2.809 g) and NaOH (5 mL, 3N) and toluene (25 mL) was stirred for 30 min. The organic phase was washed with water (10 mL), dried over Na$_2$SO$_4$ and evaporated to give (R)-1-(1-(3,4-dichlorophenyl)cyclobutyl)-3-methylbutan-1-amine as colorless oil (1.07 g, 58%). The ee was supported by mosher procedure (Ref. U.S. Pat. No. 6,974,838 B2)

EXAMPLE 9

Colorless oil (1.07 g, 58%). $^1$HNMR (400 MHz, CDCl$_3$): δ 0.53-0.60 (m, 1H); 0.84 (d, J=6.8 Hz, 3H); 0.88 (d, J=6.8 Hz, 3H); 1.10-1.13 (m, 1H); 1.63-1.67 (m, 1H); 1.77-1.83 (m, 1H); 1.91-1.97 (m, 1H); 2.12-2.16 (m, 1H); 2.21-2.33 (m, 3H); 2.97 (d, J=10.8 Hz, 1H); 6.96 (dd, J=2.0 Hz; 8.4 Hz, 1H); 7.19 (d, J=2 Hz; 1H); 7.32 (d, J=8.4 Hz, 1H). MS (ESI): m/z=287.20 (M+H$^+$).

EXAMPLE 10

(R)-1-(1-(4-Ethoxyphenyl)cyclobutyl)-3-methylbutan-1-amine (6i)

Colorless oil (1.07 g, 58%). $^1$HNMR (400 MHz, CDCl$_3$): δ 0.57-0.64 (m, 1H); 0.84 (d, J=6.8 Hz, 3H); 0.88 (d, J=6.8 Hz, 3H); 1.15-1.21 (m, 1H); 1.40 (t, J=6.8 Hz, 3H); 1.67-1.69 (m, 1H); 1.79-1.84 (m, 1H); 1.90-1.96 (m, 1H); 2.14-2.16 (m, 1H); 2.27-2.36 (m, 3H); 2.98 (dd, J=2.0 Hz; 10.8 Hz, 1H); 4.02 (q, J=6.8 Hz, 2H); 6.83 (d, J=8.4 Hz, 2H); 7.05 (d, J=8.4 Hz, 2H). MS (ESI): m/z=262.2 (M+H$^+$).

EXAMPLE 11

General Procedure for Synthesis of Compounds 12a-y (Scheme 2)

To a stirred solution of cesium carbonate (1.02 g, 5 eq) in 3 mL of DMF was added appropriate phenylcyclobutylmethylamine (0.00075 mol) and the resulting mixture was stirred at room temperature for 4 hrs. Then a solution 2-(((4-nitrophenyl)sulfonyl)oxy)ethyl ester (0.0025 mol. 4 eq) in 3 mL of DMF was added over a period of 5 minutes. The resulting mixture was stirred at room temperature for overnight. The progress of the reaction was monitored by thin layer chromatography (TLC). The reaction mixture was filtered, diluted with 10 mL of ethyl acetate, washed with brine and dried over Na$_2$SO$_4$, evaporated to give corresponding phenylcyclobutylmethylamine ester 12 which was purified by silica gel column chromatography using gradient of hexane and ethyl acetate. The pure products 12a-y were isolated as colorless thick oil in 49-69% yield.

EXAMPLE 12

2-((1-(1-(4-Chlorophenyl)cyclobutyl)-3-methylbutyl)amino)ethyl propionate (12a)

Colorless oil (0.140 g, 20%). $^1$HNMR (400 MHz, CDCl$_3$): δ 0.62-0.69 (m, 1H); 0.83 (d, J=6.8 Hz, 3H); 0.88 (d, J=6.8 Hz, 3H); 1.06-1.09 (m, 1H); 1.14 (t, J=7.6 Hz, 3H); 1.60-1.64 (m, 1H); 1.75-1.79 (m, 1H); 1.85-1.91 (m, 1H); 2.15-2.17 (m, 1H); 2.24-2.40 (m, 5H); 2.75 (dd, J=2.4 Hz; 10.0 Hz, 1H); 2.96-3.00 (m, 2H); 4.12 (t, J=4.4 Hz, 2H); 7.16 (d, J=8.4 Hz, 2H); 7.26 (d, J=8.4 Hz, 2H). MS (ESI): m/z=352.20 (M+H$^+$).

EXAMPLE 13

2-((1-(1-(4-Chlorophenyl)cyclobutyl)-3-methylbutyl)amino)ethyl butyrate 12b (Scheme 2)

Colorless oil (0.12 g, 17%). $^1$HNMR (400 MHz, CDCl$_3$): δ 0.62-0.69 (m, 1H); 0.83 (d, J=6.8 Hz, 3H); 0.88 (d, J=6.8 Hz, 3H); 0.92 (t, J=7.6 Hz, 3H); 1.06-1.11 (m, 1H); 1.60-1.70 (m, 4H); 1.75-1.79 (m, 1H); 1.86-1.91 (m, 1H); 2.15-2.17 (m, 1H); 2.24-2.32 (m, 4H); 2.35-2.39 (m, 1H); 2.75 (dd, J=2.4 Hz; 10.0 Hz, 1H); 2.96-3.01 (m, 2H); 4.12 (t, J=4.4 Hz, 2H); 7.16 (d, J=8.4 Hz, 2H); 7.26 (d, J=8.4 Hz, 2H). MS (ESI): m/z=366.2 (M+H$^+$).

EXAMPLE 14

2-((1-(1-(4-Chlorophenyl)cyclobutyl)-3-methylbutyl)amino)ethyl isobutyrate 12c (Scheme 2)

Colorless oil (0.08 g, 20%). $^1$HNMR (400 MHz), CDCl$_3$): d 0.62-0.69 (m, 1H); 0.84 (d, J=6.8 Hz, 3H); 0.88 (d, J=6.8 Hz, 3H); 1.06-1.11 (m, 1H); 1.18 (d=J=6.4 Hz, 6H); 1.59-1.65 (m, 1H); 1.75-1.79 (m, 1H); 1.88-1.92 (m, 1H); 2.15-2.17 (m, 1H); 2.26-2.31 (m, 1H); 2.38-2.40 (m, 1H); 2.50-2.60 (m, 3H); 2.74-2.76 (m, 1H); 2.97-3.01 (m, 2H); 4.12 (t, J=4.4 Hz, 2H); 7.17 (d, J=8.8 Hz, 2H); 7.26 (d, J=8.8 Hz, 2H). MS (ESI): m/z=366.2 (M+H$^+$).

EXAMPLE 15

2-((1-(1-(4-Chlorophenyl)cyclobutyl)-3-methylbutyl)amino)ethyl 3-methylbutanoate 12d (Scheme 2)

Colorless oil (0.22 g, 40%). ($^1$HNMR (400 MHz), CDCl$_3$): δ 0.62-0.69 (m, 1H); 0.84 (d, J=6.8 Hz, 3H); 0.88 (d, J=6.8 Hz, 3H); 0.95 (d, J=6.8 Hz, 6H); 0.94-0.95 (m, 1H); 0.98-1.12 (m, 1H); 1.61-1.65 (m, 1H); 1.76-1.80 (m, 1H); 1.87-1.92 (m, 1H); 2.05-2.10 (m, 2H); 2.17-2.31 (m, 5H); 2.36-2.40 (m, 1H); 2.75 (dd, J=2.4 Hz, 10 Hz, 1H); 2.83-2.94-3.02 (m, 2H); 4.10 (t, J=4.4 Hz, 2H); 7.17 (d, J=8.4 Hz, 1H); 7.26 (d, J=8.4 Hz, 1H). MS (ESI): m/z=380.2 (M+H$^+$).

EXAMPLE 16

2-((1-(1-(2-Fluorophenyl)cyclobutyl)-3-methylbutyl)amino)ethyl acetate 12e (Scheme 2)

Colorless oil (0.1 g, 20%). $^1$HNMR (400 MHz), CDCl$_3$): δ 0.63-0.69 (m, 1H); 0.83 (d, J=6.8 Hz, 3H); 0.87 (d, J=6.8 Hz, 3H); 0.91-0.95 (m, 1H); 1.59-1.66 (m, 1H); 1.72-1.81 (m, 1H); 1.85-1.92 (m, 1H); 2.06 (s, 3H); 2.12-2.19 (m, 2H); 2.23-2.41 (m, 3H); 2.73 (dd, J=2.8 Hz; 10.0 Hz, 1H); 2.97 (t, J=6.4 Hz, 2H); 4.10 (t, J=5.6 Hz, 2H); 6.90-7.19 (m, 4H). MS (ESI): m/z=322.1 (M+H$^+$).

EXAMPLE 17

2-((1-(1-(2-Fluorophenyl)cyclobutyl)-3-methylbutyl)amino)ethyl butyrate 12f (Scheme 2)

Colorless oil (0.3 g, 41%). $^1$HNMR (400 MHz), CDCl$_3$): δ 0.62-0.69 (m, 1H); 0.83 (d, J=6.8 Hz, 3H); 0.87 (d, J=6.8 Hz, 3H); 0.94 (t, J=7.6 Hz, 3H); 0.91-0.95 (m, 1H); 1.59-1.68 (m, 3H); 1.75-1.79 (m, 1H); 1.85-1.92 (m, 1H); 2.04-2.17 (m, 1H); 2.19-2.37 (m, 5H); 2.73 (dd, J=2.8 Hz; 10.0 Hz, 1H); 2.97 (t, J=6.4 Hz, 2H); 4.10 (t, J=5.6 Hz, 2H); 6.97-7.22 (m, 4H). MS (ESI): m/z=350.2 (M+H$^+$).

EXAMPLE 18

2-((1-(1-(2-Fluorophenyl)cyclobutyl)-3-methylbutyl)amino)ethyl isobutyrate 12g (Scheme 2)

Colorless oil (0.11 g, 23%). $^1$HNMR (400 MHz), CDCl$_3$): δ 0.84 (d, J=6.8 Hz, 6H); 0.91-0.95 (m, 1H); 1.20 (d, J=6.8 Hz, 6H); 1.26-1.31 (m, 2H); 1.62-1.69 (m, 1H); 1.79-1.84 (m, 1H); 1.93-2.00 (m, 1H); 2.29-2.42 (m, 4H); 2.50-2.57 (m, 1H); 2.84-3.01 (m, 3H); 4.10 (t, J=4.4 Hz, 2H); 6.97-7.18 (m, 4H). MS (ESI): m/z=350.2 (M+H$^+$).

EXAMPLE 19

2-((1-(1-(3-Fluorophenyl)cyclobutyl)-3-methylbutyl)amino)ethyl acetate 12h (Scheme 2)

Colorless oil (0.12 g, 20%). $^1$HNMR (400 MHz), CDCl$_3$): δ 0.63-0.69 (m, 1H); 0.83 (d, J=6.8 Hz, 3H); 0.87 (d, J=6.8 Hz, 3H); 0.91-0.95 (m, 1H); 1.59-1.66 (m, 1H); 1.72-1.81 (m, 1H); 1.85-1.92 (m, 1H); 2.06 (s, 3H); 2.12-2.19 (m, 2H); 2.23-2.41 (m, 3H); 2.73 (dd, J=2.8 Hz; 10.0 Hz, 1H); 2.97 (t, J=6.4 Hz, 2H); 4.10 (t, J=5.6 Hz, 2H); 6.97-7.20 (m, 4H). MS (ESI): m/z=322.1 (M+H$^+$).

EXAMPLE 20

2-((1-(1-(3-Fluorophenyl)cyclobutyl)-3-methylbutyl)amino)ethyl propionate 12i (Scheme 2)

Colorless oil (0.11 g, 20%). $^1$HNMR (400 MHz), CDCl$_3$): δ 0.63-0.69 (m, 1H); 0.83 (d, J=6.8 Hz, 3H); 0.87 (d, J=6.8 Hz, 3H); 0.91-0.95 (m, 1H); 1.20 (d, J=7.6 Hz, 3H); 1.59-1.66 (m, 1H); 1.72-1.81 (m, 1H); 1.85-1.92 (m, 1H); 2.12-2.19 (m, 2H); 2.23-2.41 (m, 5H); 2.73 (dd, J=2.8 Hz; 10.0 Hz, 1H); 2.97 (t, J=6.4 Hz, 2H); 4.10 (t, J=5.6 Hz, 2H); 6.97-7.20 (m, 4H). MS (ESI): m/z=336.1 (M+H$^+$).

EXAMPLE 21

2-((1-(1-(3-Fluorophenyl)cyclobutyl)-3-methylbutyl)amino)ethyl butyrate 12j (Scheme 2)

Colorless oil (0.2 g, 35%). $^1$HNMR (400 MHz), CDCl$_3$): δ 0.62-0.69 (m, 1H); 0.83 (d, J=6.8 Hz, 3H); 0.87 (d, J=6.8 Hz, 3H); 0.94 (t, J=7.6 Hz, 3H); 0.91-0.95 (m, 1H); 1.59-1.68 (m, 3H); 1.75-1.79 (m, 1H); 1.85-1.92 (m, 1H); 2.04-2.17 (m, 1H); 2.19-2.37 (m, 5H); 2.73 (dd, J=2.8 Hz; 10.0 Hz, 1H); 2.97 (t, J=6.4 Hz, 2H); 4.10 (t, J=5.6 Hz, 2H); 6.97-6.98 (t-broad, 2H); 7.20-7.21 (t-broad, 2H). MS (ESI): m/z=350.2 (M+H$^+$).

EXAMPLE 22

2-((1-(1-(3-Fluorophenyl)cyclobutyl)-3-methylbutyl)amino)ethyl isobutyrate 12k (Scheme 2)

Colorless oil (0.09 g, 22%). $^1$HNMR (400 MHz), CDCl$_3$): δ 0.84 (d, J=6.8 Hz, 6H); 0.91-0.95 (m, 1H); 1.20 (d, J=6.8 Hz, 6H); 1.26-1.31 (m, 2H); 1.62-1.69 (m, 1H); 1.79-1.84 (m, 1H); 1.93-2.00 (m, 1H); 2.29-2.42 (m, 4H); 2.50-2.57 (m, 1H); 2.84-3.01 (m, 3H); 4.10 (t, J=4.4 Hz, 2H); 7.06-7.17 (m, 4H). MS (ESI): m/z=350.2 (M+H$^+$).

EXAMPLE 23

2-((1-(1-(4-Fluorophenyl)cyclobutyl)-3-methylbutyl)amino)ethyl acetate 12l (Scheme 2)

Colorless oil (0.2 g, 38%). $^1$HNMR (400 MHz), CDCl$_3$): δ 0.63-0.69 (m, 1H); 0.83 (d, J=6.8 Hz, 3H); 0.87 (d, J=6.8 Hz, 3H); 0.91-0.95 (m, 1H); 1.59-1.66 (m, 1H); 1.72-1.81 (m, 1H); 1.85-1.92 (m, 1H); 2.06 (s, 3H); 2.12-2.19 (m, 2H); 2.23-2.41 (m, 3H); 2.73 (dd, J=2.8 Hz; 10.0 Hz, 1H); 2.97 (t, J=6.4 Hz, 2H); 4.10 (t, J=5.6 Hz, 2H); 6.97 (dd, J=8.4 Hz; 11.6 Hz, 1H); 7.06 (dd, J=1.6 Hz; 7.6 Hz, 1H); 7.12-7.17 (m, 2H). MS (ESI): m/z=322.1 (M+H$^+$).

EXAMPLE 24

2-((1-(1-(4-Fluorophenyl)cyclobutyl)-3-methylbutyl)amino)ethyl propionate 12m (Scheme 2)

Colorless oil (0.15 g, 34%). $^1$HNMR (400 MHz), CDCl$_3$): δ 0.63-0.69 (m, 1H); 0.83 (d, J=6.8 Hz, 3H); 0.87 (d, J=6.8 Hz, 3H); 0.91-0.95 (m, 1H); 1.20 (d, J=7.6 Hz, 3H); 1.59-1.66 (m, 1H); 1.72-1.81 (m, 1H); 1.85-1.92 (m, 1H); 2.12-2.19 (m, 2H); 2.23-2.41 (m, 5H); 2.73 (dd, J=2.8 Hz; 10.0 Hz, 1H); 2.97 (t, J=6.4 Hz, 2H); 4.10 (t, J=5.6 Hz, 2H); 6.97 (dd, J=1.6 Hz; 7.6 Hz, 2H); 7.20 (dd, J=1.6 Hz; 7.6 Hz, 2H). MS (ESI): m/z=336.1 (M+H$^+$).

EXAMPLE 25

2-((1-(1-(4-Fluorophenyl)cyclobutyl)-3-methylbutyl)amino)ethyl butyrate 12n (Scheme 2)

Colorless oil (0.2 g, 40%). $^1$HNMR (400 MHz), CDCl$_3$): δ 0.62-0.69 (m, 1H); 0.83 (d, J=6.8 Hz, 3H); 0.87 (d, J=6.8 Hz, 3H); 0.94 (t, J=7.6 Hz, 3H); 0.91-0.95 (m, 1H); 1.59-1.68 (m, 3H); 1.75-1.79 (m, 1H); 1.85-1.92 (m, 1H); 2.04-2.17 (m, 1H); 2.19-2.37 (m, 5H); 2.73 (dd, J=2.8 Hz; 10.0 Hz, 1H); 2.97 (t, J=6.4 Hz, 2H); 4.10 (t, J=5.6 Hz, 2H); 6.97 (dd, J=1.6 Hz; 7.6 Hz, 2H); 7.20 (dd, J=1.6 Hz; 7.6 Hz, 2H). MS (ESI): m/z=350.2 (M+H$^+$).

EXAMPLE 26

2-((1-(1-(3-Fluorophenyl)cyclobutyl)-3-methylbutyl)amino)ethyl isobutyrate 12o (Scheme 2)

Colorless oil (0.1 g, 20%). $^1$HNMR (400 MHz), CDCl$_3$): δ 0.84 (d, J=6.8 Hz, 6H); 0.91-0.95 (m, 1H); 1.20 (d, J=6.8 Hz, 6H); 1.26-1.31 (m, 2H); 1.62-1.69 (m, 1H); 1.79-1.84 (m, 1H); 1.93-2.00 (m, 1H); 2.29-2.42 (m, 4H); 2.50-2.57 (m, 1H); 2.84-3.01 (m, 3H); 4.10 (t, J=4.4 Hz, 2H); 6.97 (dd, J=8.4 Hz; 11.6 Hz, 1H); 7.06 (dd, J=1.6 Hz; 7.6 Hz, 1H); 7.12-7.17 (m, 2H). MS (ESI): m/z=350.2 (M+H$^+$).

EXAMPLE 27

2-((1-(1-(3-Fluorophenyl)cyclobutyl)-3-methylbutyl)amino)ethyl 3-methylbutanoate 12p (Scheme 2)

Colorless oil (91 mg, 13%) $^1$HNMR (400 MHz), CDCl$_3$): δ 0.85 (d, J=6.8 Hz, 6H); 0.91-0.95 (m, 1H); 0.95 (d, J=6.8 Hz, 6H); 1.25-1.26 (m, 2H); 1.63-1.69 (m, 1H); 1.80-1.84 (m, 1H); 1.93-1.98 (m, 1H); 2.07-2.10 (m, 1H); 2.17-2.31 (m, 2H); 2.340-2.40 (m, 4H); 2.83-2.87.01 (m, 3H); 4.10 (t, J=4.4 Hz, 2H); 6.97 (dd, J=8.8 Hz; 11.6 Hz, 1H); 7.06 (dd, J=1.6 Hz; 7.6 Hz, 1H); 7.12-7.17 (m, 2H). MS (ESI): m/z=364.3 (M+H$^+$).

EXAMPLE 28

2-((1-(1-(3,4-Dichlorophenyl)cyclobutyl)-3-methylbutyl)amino)ethyl propionate 12q (Scheme 2)

Colorless oil (94 mg, 14%). $^1$HNMR (400 MHz), CDCl$_3$): δ 0.61-0.68 (m, 1H); 0.84 (d, J=6.8 Hz, 3H); 0.89 (d, J=6.8 Hz, 3H); 1.03-1.04 (m, 1H); 1.14 (t, J=7.6 Hz, 3H); 1.62-1.63 (m, 1H); 1.75-1.78 (m, 1H); 1.88-1.91 (m, 1H); 2.21-2.38 (m, 6H); 2.75 (dd, J=2.4 Hz; 10.0 Hz, 1H); 2.96-3.02 (m, 2H);

4.12 (t, J=4.4 Hz, 2H); 7.06 (dd, J=2.4 Hz; 8.4 Hz, 1H); 7.31 (d, J=2.0 Hz, 1H); 7.34 (d, J=8.4 Hz, 1H). MS (ESI): m/z=387.2 (M+H$^+$).

EXAMPLE 29

2-((1-(1-(3,4-Dichlorophenyl)cyclobutyl)-3-methylbutyl)amino)ethyl butyrate 12r (Scheme 2)

Colorless oil (0.12 g, 40%). $^1$HNMR (400 MHz), CDCl$_3$): δ 0.62-0.67 (m, 1H); 0.84 (d, J=6.8 Hz, 3H); 0.89 (d, J=6.8 Hz, 3H); 0.96 (t, J=7.6 Hz, 3H); 1.04-1.10 (m, 1H); 1.62-1.73 (m, 4H); 1.75-1.82 (m, 1H); 1.88-1.93 (m, 1H); 2.10-2.32 (m, 6H); 2.35-2.40 (m, 1H); 2.75 (dd, J=2.4 Hz; 10.0 Hz, 1H); 2.95-3.05 (m, 2H); 4.12 (t, J=4.4 Hz, 2H); 7.06 (dd, J=2.0 Hz; 8.4 Hz, 1H); 7.31 (d, J=2.0 Hz, 1H); 7.34 (d, J=8.4 Hz, 1H). MS (ESI): m/z=401.3 (M+H$^+$).

EXAMPLE 30

2-((1-(1-(3,4-Dichlorophenyl)cyclobutyl)-3-methylbutyl)amino)ethyl isobutyrate 12s (Scheme 2)

Colorless oil (0.18 g, 26%). $^1$HNMR (400 MHz), CDCl$_3$): δ 0.52-0.62 (m, 1H); 0.78 (d, J=6.8 Hz, 3H); 0.82 (d, J=6.8 Hz, 3H); 0.97-1.04 (m, 1H); 1.09 (d=J=6.4 Hz, 6H); 1.53-1.56 (m, 1H); 1.69-1.73 (m, 1H); 1.82-1.85 (m, 1H); 2.07-2.17 (m, 1H); 2.15-2.21 (m, 2H); 2.31-2.33 (m, 1H); 2.44-2.51 (m, 1H); 2.70 (dd, J=2.4 Hz; 10.0 Hz, 1H); 2.87-3.00 (m, 2H); 4.12 (t, J=4.4 Hz, 2H); 7.00 (dd, J=2.4 Hz; 8.4 Hz, 1H); 7.24 (d, J=2.0 Hz, 1H); 7.27 (d, J=8.4 Hz, 1H). MS (ESI): m/z=401.3 (M+H$^+$).

EXAMPLE 31

2-((1-(1-(3,4-Dichlorophenyl)cyclobutyl)-3-methylbutyl)amino)ethyl 3-methylbutanoate 12t (Scheme 2)

Colorless oil (0.13 g, 39%). $^1$HNMR (400 MHz), CDCl$_3$): δ 0.85 (d, J=6.8 Hz, 6H); 0.91-0.95 (m, 1H); 0.95 (d, J=6.8 Hz, 6H); 1.25-1.26 (m, 2H); 1.63-1.69 (m, 1H); 1.80-1.84 (m, 1H); 1.93-1.98 (m, 1H); 2.07-2.10 (m, 1H); 2.17-2.31 (m, 2H); 2.340-2.40 (m, 4H); 2.83-2.87.01 (m, 3H); 4.10 (t, J=4.4 Hz, 2H); 7.00 (dd, J=2.4 Hz; 8.4 Hz, 1H); 7.24 (d, J=2.0 Hz, 1H); 7.27 (d, J=8.4 Hz, 1H). MS (ESI): m/z=415.3 (M+H$^+$).

EXAMPLE 32

2-((1-(1-(4-Ethoxyphenyl)cyclobutyl)-3-methylbutyl)amino)ethyl propionate 12u (Scheme 2)

Colorless oil (84 mg, 12%). $^1$HNMR (400 MHz), CDCl$_3$): δ 0.65-0.72 (m, 1H); 0.83 (d, J=6.8 Hz, 3H); 0.88 (d, J=6.8 Hz, 3H); 1.06-1.10 (m, 1H); 1.14 (t, J=7.6 Hz, 3H); 1.40 (t, J=7.2 Hz, 3H); 1.60-1.64 (m, 1H); 1.75-1.87 (m, 2H); 2.12-2.16 (m, 1H); 2.27-2.37 (m, 5H); 2.71 (dd, J=2.8 Hz; 10.0 Hz, 1H); 2.93-2.99 (m, 2H); 4.02 (q, J=7.2 Hz, 2H); 4.12 (t, J=4.4 Hz, 2H); 6.83 (d, J=8.8 Hz, 2H); 7.15 (d, J=8.8 Hz, 2H). MS (ESI): m/z=362.3 (M+H$^+$).

EXAMPLE 33

2-((1-(1-(4-Ethoxyphenyl)cyclobutyl)-3-methylbutyl)amino)ethyl butyrate 12v (Scheme 2)

Colorless oil (0.2, 40%). $^1$HNMR (400 MHz), CDCl$_3$): δ 0.66-0.72 (m, 1H); 0.83 (d, J=6.8 Hz, 3H); 0.88 (d, J=6.8 Hz, 3H); 0.94 (t, J=7.6 Hz, 3H); 1.06-1.12 (m, 1H); 1.40 (t, J=6.8 Hz, 3H); 1.60-1.69 (m, 3H); 1.75-1.80 (m, 1H); 1.82-1.85 (m, 1H); 2.12-2.16 (m, 1H); 2.27-2.37 (m, 5H); 2.71 (dd, J=2.8 Hz; 10.0 Hz, 1H); 2.93-2.99 (m, 2H); 4.02 (q, J=7.2 Hz, 2H); 4.12 (t, J=4.4 Hz, 2H); 6.83 (d, J=8.8 Hz, 2H); 7.15 (d, J=8.8 Hz, 2H). MS (ESI): m/z=376.3 (M+H$^+$).

EXAMPLE 34

2-((1-(1-(4-Ethoxyphenyl)cyclobutyl)-3-methylbutyl)amino)ethyl isobutyrate 12w (Scheme 2)

Colorless oil (0.15 g, 40%). $^1$HNMR (400 MHz), CDCl$_3$): δ 0.65-0.72 (m, 1H); 0.83 (d, J=6.8 Hz, 3H); 0.88 (d, J=6.8 Hz, 3H); 1.06-1.10 (m, 1H); 1.07 (d=J=6.4 Hz, 6H); 1.32 (t, J=7.2 Hz, 3H); 1.53-1.59 (m, 1H); 1.68-1.73 (m, 1H); 1.75-1.80 (m, 1H); 2.07-2.11 (m, 1H); 2.20-2.30 (m, 3H); 2.43-2.50 (m, 1H); 2.65 (dd, J=2.8 Hz; 10.0 Hz, 1H); 2.88-2.94 (m, 2H); 3.97 (q, J=7.2 Hz, 2H); 4.03 (t, J=4.4 Hz, 2H); 6.76 (d, J=8.8 Hz, 2H); 7.0821 (d, J=8.8 Hz, 2H). MS (ESI): m/z=376.3 (M+H$^+$).

EXAMPLE 35

2-((1-(1-(4-Ethoxyphenyl)cyclobutyl)-3-methylbutyl)amino)ethyl 3-methylbutanoate 12x (Scheme 2)

Colorless oil (0.08 g, 20%). $^1$HNMR (400 MHz), CDCl$_3$): δ 0.65-0.79 (m, 1H); 0.83 (d, J=6.8 Hz, 3H); 0.88 (d, J=6.8 Hz, 3H); 0.95 (d=J=6.4 Hz, 6H); 1.06-1.12 (m, 1H); 1.23-1.25 (m, 1H); 1.32 (t, J=7.2 Hz, 3H); 1.62-1.65 (m, 1H); 1.74-1.79 (m, 1H); 1.82-1.88 (m, 1H); 2.04-2.18 (m, 4H); 2.26-2.37 (m, 3H); 2.71 (dd, J=2.8 Hz; 10.0 Hz, 1H); 2.93-3.00 (m, 2H); 4.02 (q, J=7.2 Hz, 2H); 4.09 (t, J=4.4 Hz, 2H); 6.83 (d, J=8.4 Hz, 2H); 7.0821 (d, J=8.4 Hz, 2H). MS (ESI): m/z=390.3 (M+H$^+$).

EXAMPLE 36

2-((1-(1-(4-Butoxyphenyl)cyclobutyl)-3-methylbutyl)amino)ethyl isobutyrate 12y (Scheme 2)

Colorless oil (0.2 g, 39%). $^1$HNMR (400 MHz), CDCl$_3$): δ 0.64-0.71 (m, 1H); 0.82 (d, J=6.8 Hz, 3H); 0.88 (d, J=6.8 Hz, 3H); 0.96 (t, J=7.2 Hz, 3H); 1.04-1.11 (m, 1H); 1.13 (d=J=2.4 Hz, 3H); 1.15 (d, J=2.4 Hz, 3H); 1.43-1.52 (m, 2H); 1.60-1.64 (m, 1H); 1.71-1.78 (m, 3H); 1.80-1.86 (m, 1H); 2.20-2.22 (m, 1H); 2.24-2.40 (m, 3H); 2.44-2.55 (m, 1H); 2.65 (dd, J=2.8 Hz; 10.0 Hz, 1H); 2.88-3.00 (m, 2H); 3.87 (t, J=7.2 Hz, 2H); 4.03 (m, 2H); 6.81 (d, J=8.8 Hz, 2H); 7.0821 (d, J=8.8 Hz, 2H). MS (ESI): m/z=404.3 (M+H$^+$).

EXAMPLE 37

General Procedure for Compounds 16a-b (Scheme 3)

To a suspension of isobutyric acid (5 g, 0.056 mol) and ethylene glycol (15.8 g, 0.283 mol.) was added dropwise Sulfuric acid (cat. 0.4 mL). The resulting mixture was heated at 80° C. for 4 hrs. The progress of the reaction was monitored by thin layer chromatography (TLC). The reaction mixture was then cooled down to rt, diluted with dichloromethane and washed with saturated aqueous sodium bicarbonate solution, dried over magnesium sulfate and evaporated to give 2-hydroxyethyl isobutyrate isolated as a colorless oil.

EXAMPLE 38

2-Hydroxyethyl isobutyrate 16a

Colorless oil (5.88 g, 78%). $^1$HNMR (400 MHz), CDCl$_3$: δ 1.19 (d, J=6.8 Hz, 6H); 2.23 (sbr, 1H); 2.54-2.61 (m, 1H); 3.81 (t, J=4.4 Hz, 2H); 4.18-4.20 (m, 2H).

EXAMPLE 39

2-Hydroxyethyl propionate 16b

Colorless oil (6.2 g, 80%). $^1$HNMR (400 MHz), CDCl$_3$: δ 1.08 (t, J=7.6 Hz, 3H); 2.31 (q, J=7.6 Hz, 2H); 2.46 (sbr, 1H); 3.75 (t, J=4.8 Hz, 2H); 4.12-4.15 (m, 2H).

EXAMPLE 40

General Procedure for Synthesis of Compounds 18a-d (Scheme 3)

An appropriate 2-Hydroxyethyl (0.00075 mol.) was dissolved in DCM (5 mL) at 0° C. 4-nitrobenzene-1-sulfonyl chloride (0.167 g, 1 eq) in 5 mL of DCM was slowly added while the mixture was stirred at ice bath (0-5° C.). Triethylamine (0.158 mL, 1.5 eq) was finally added and the mixture was continuously stirred at ice bath for 1 h. The progress of the reaction was monitored by TLC. After the reaction was complete, the mixture was washed with brine and concentrated using a rotary evaporator. It was further purified using a column chromatography using a gradient of ethyl acetate/Hexane to give corresponding pure nitrosulphonyl ester 12 as colorless white solid 2-(((4-Nitrophenyl)sulfonyl)oxy)ethyl propionate 18a (Scheme 3)

White solid (0.21 g, 83% yield). $^1$HNMR (400 MHz), CDCl$_3$): δ 1.08 (t, J=7.6 Hz, 3H); 2.31 (q, J=7.6 Hz, 2H); 4.30 (t, J=4.4 Hz, 2H); 4.36 (t, J=4.4 Hz, 2H); 8.13 (d, J=9.2 Hz, 2H); 8.42 (d, J=9.2 Hz, 2H).

EXAMPLE 41

2-(((4-Nitrophenyl)sulfonyl)oxy)ethyl isobutyrate 18c (Scheme 3)

Light yellow solid (1.2 g, 80%). $^1$HNMR (400 MHz), CDCl$_3$): δ 1.19 (d, J=6.8 Hz, 6H); 2.54-2.61 (m, 1H); 4.30 (t, J=4.4 Hz, 2H); 4.36 (t, J=4.4 Hz, 2H); 8.13 (d, J=9.2 Hz, 2H); 8.42 (d, J=9.2 Hz, 2H).

General Procedure for Synthesis of Compounds 21a-j

A solution of appropriate phenylcyclobutylmethylamine 6 (0.0009 mol) and carbamate (0.0009 mol) in methanol anhydrous (10 mL) was stirred for 15 hours at room temperature. After the reaction was complete, the reaction mixture was cooled down to 0° C. and NaBH$_4$ (0.36 g, 5.0 eq) was added. The reaction mixture was stirred for 6 hours from 0° C. to rt, And then NaHCO$_3$ solution was added. The product was extracted with ethyl acetate, dried over anhydrous Na$_2$SO$_4$ and evaporated under reduced pressure to give ethyl corresponding phenylcyclobutylmethylamine carbamate 21 which was purified by silica gel column chromatography using gradient of hexane and ethyl acetate, isolated as a colorless thick oil in 46-66% yield.

The optical pur (R)-carbamates 21c-d were prepared by using corresponding starting optically pur (R)-amine 6e-f. under identical reaction conditions.

The selected carbamates 21a-b were also synthesized by alternate route by alkylating corresponding amine 6e-i with carbamate 19 as described in scheme 4

General Procedure for Synthesis of Compounds 19

To a stirred solution of cesium carbonate (3.5 g, 5 eq) in 5 mL of DMF (anhydrous) was added amine 6e-f (0.6 g, 0.0022 mol. 1 eq) and the resulting mixture was stirred at room temperature for 4 hrs. Then 2-((ethoxycarbonyl)amino)ethyl nitrobenzenesulfonate (0.0091 mol. 4 eq) was added. The resulting mixture was stirred at room temperature for two days. The progress of the reaction was monitored by thin layer chromatography (TLC). The reaction mixture was filtered, diluted with 10 mL of ethyl acetate, washed with brine and dried over Na$_2$SO$_4$, evaporated to give the corresponding amine carbamate which was purified by silica gel column chromatography using gradient of DCM/MeOH, isolated as a thick oil with 20-40% yield.

EXAMPLE 42

Ethyl (2-((1-(1-(3,4-dichlorophenyl)cyclobutyl)-3-methylbutyl)amino)ethyl)carbamate 21a (Scheme 4).

Colorless oil (0.180 g, 46%). $^1$HNMR (400 MHz), CDCl$_3$): δ 0.53-0.62 (m, 1H); 0.78 (d, J=6.8 Hz, 3H); 0.82 (d, J=6.8 Hz, 3H); 0.99-1.10 (m, 1H); 1.18 (t, J=7.2 Hz, 3H); 1.52-1.58 (m, 1H); 1.69-1.74 (m, 1H); 1.80-1.86 (m, 1H); 2.04-2.11 (m, 1H); 2.15-2.20 (m, 2H); 2.27-2.34 (m, 1H); 2.67 (dd, J=2.4 Hz; 10.0 Hz, 1H); 2.74-2.78 (m 1H); 2.83-2.87 (m, 1H); 3.10-3.14 (m, 2H) 4.06 (q, J=6.8 Hz, 2H); 4.95 (sbroad, 1H); 6.99 (dd, J=2.0 Hz; 8.4 Hz, 1H); 7.19 (d, J=2 Hz; 1H); 7.28 (d, J=8.4 Hz, 1H). MS (ESI): m/z=402.2 (M+H$^+$).

EXAMPLE 43

Ethyl (2-((1-(1-(4-ethoxyphenyl)cyclobutyl)-3-methylbutyl)amino)ethyl)carbamate 21b (Scheme 4)

Colorless oil (0.2 g, 47%). $^1$HNMR (400 MHz), CDCl$_3$): δ 0.64-0.71 (m, 1H); 0.84 (d, J=6.8 Hz, 3H); 0.88 (d, J=6.8 Hz, 3H); 1.08-1.13 (m, 1H); 1.24 (t, J=7.2 Hz, 3H); 1.42 (t, J=7.2 Hz, 3H); 1.61-1.64 (m, 1H); 1.75-1.88 (m, 2H); 2.09-2.16 (m, 1H); 2.29-2.35 (m, 3H); 2.69 (dd, J=2.4 Hz; 10.0 Hz, 1H); 2.86 (t, J=5.6 Hz, 2H); 3.17 (q, J=5.6 Hz, 2H); 4.03 (q, J=6.8 Hz, 2H); 4.11 (q, J=6.8H, 2H); 5.12 (sbroad, 1H); 6.84 (d, J=8.4 Hz, 2H); 7.14 (d, J=8.4 Hz, 2H). MS (ESI): m/z=377.3 (M+H$^+$).

EXAMPLE 44

(R)-Ethyl (2-((1-(1-(3,4-dichlorophenyl)cyclobutyl)-3-methylbutyl)amino)ethyl)carbamate 21c (Scheme 4)

Colorless oil (0.1 g, 39%). $^1$HNMR (400 MHz), CDCl$_3$): δ 0.53-0.62 (m, 1H); 0.78 (d, J=6.8 Hz, 3H); 0.82 (d, J=6.8 Hz, 3H); 0.99-1.10 (m, 1H); 1.18 (t, J=7.2 Hz, 3H); 1.52-1.58 (m, 1H); 1.69-1.74 (m, 1H); 1.80-1.86 (m, 1H); 2.04-2.11 (m, 1H); 2.15-2.20 (m, 2H); 2.27-2.34 (m, 1H); 2.67 (dd, J=2.4

Hz; 10.0 Hz, 1H); 2.74-2.78 (m 1H); 2.83-2.87 (m, 1H); 3.10-3.14 (m, 2H) 4.06 (q, J=6.8 Hz, 2H); 4.95 (sbroad, 1H); 6.99 (dd, J=2.0 Hz; 8.4 Hz, 1H); 7.19 (d, J=2 Hz; 1H); 7.28 (d, J=8.4 Hz, 1H). MS (ESI): m/z=402.2 (M+H$^+$).

EXAMPLE 45

(R)-Ethyl (2-((1-(1-(4-ethoxyphenyl)cyclobutyl)-3-methylbutyl)amino)ethyl)carbamate 21d (Scheme 4)

Colorless oil (0.2 g, 47%). $^1$HNMR (400 MHz), CDCl$_3$): δ 0.64-0.71 (m, 1H); 0.84 (d, J=6.8 Hz, 3H); 0.88 (d, J=6.8 Hz, 3H); 1.08-1.13 (m, 1H); 1.24 (t, J=7.2 Hz, 3H); 1.42 (t, J=7.2 Hz, 3H); 1.61-1.64 (m, 1H); 1.75-1.88 (m, 2H); 2.09-2.16 (m, 1H); 2.29-2.35 (m, 3H); 2.69 (dd, J=2.4 Hz; 10.0 Hz, 1H); 2.86 (t, J=5.6 Hz, 2H); 3.17 (q, J=5.6 Hz, 2H); 4.03 (q, J=6.8 Hz, 2H); 4.11 (q, J=6.8H, 2H); 5.12 (sbroad, 1H); 6.84 (d, J=8.4 Hz, 2H); 7.14 (d, J=8.4 Hz, 2H). MS (ESI): m/z=377.3 (M+H$^+$).

EXAMPLE 46

Isopropyl (2-((1-(1-(4-ethoxyphenyl)cyclobutyl)-3-methylbutyl)amino)ethyl)carbamate 21e (Scheme 4)

Colorless oil (0.2 g, 46%) $^1$HNMR (400 MHz), CDCl$_3$): δ 0.61-0.68 (m, 1H); 0.82 (d, J=6.8 Hz, 3H); 0.86 (d, J=6.8 Hz, 3H); 1.058-1.12 (m, 1H); 1.21 (d, J=6.4 Hz, 6H); 1.39 (t, J=7.2 Hz, 3H); 1.58-1.65 (m, 1H); 1.70-1.87 (m, 2H); 2.05-2.14 (m, 1H); 2.26-2.34 (m, 3H); 2.67 (dd, J=2.4 Hz; 10.0 Hz, 1H); 2.84 (t, J=5.6 Hz, 2H); 3.14 (q, J=5.6 Hz, 2H); 4.01 (q, J=6.8 Hz, 2H); 4.86-4.92 (m, 1H); 5.05 (sbroad, 1H); 6.84 (d, J=8.4 Hz, 2H); 7.14 (d, J=8.4 Hz, 2H). MS (ESI): m/z=391.3 (M+H$^+$).

EXAMPLE 47

Isopropyl (2-((1-(1-(3,4-dichlorophenyl)cyclobutyl)-3-methylbutyl)amino)ethyl)carbamate 21f (Scheme 4)

Colorless oil (0.3 g, 50%). $^1$HNMR (400 MHz), CDCl$_3$): δ 0.59-0.65 (m, 1H); 0.83 (d, J=6.8 Hz, 3H); 0.87 (d, J=6.8 Hz, 3H); 1.03-1.09 (m, 1H); 1.21 (d, J=6.4 Hz, 6H); 1.58-1.64 (m, 1H); 1.73-1.78 (m, 1H); 1.85-1.91 (m, 1H); 2.12-2.16 (m, 1H); 2.23-2.26 (m, 2H); 2.32-2.37 (m, 1H); 2.72 (dd, J=2.4 Hz; 10.0 Hz, 1H); 2.79-2.83 (m 1H); 2.88-2.93 (m, 1H); 3.16-3.19 (m, 2H) 4.88-4.93 (m, 1H); 4.95 (sbroad, 1H); 6.99 (dd, J=2.0 Hz; 8.4 Hz, 1H); 7.19 (d, J=2 Hz; 1H); 7.28 (d, J=8.4 Hz, 1H). MS (ESI): m/z=416.3 (M+H$^+$).

EXAMPLE 48

Ethyl(1-((1-(1-(3,4-dichlorophenyl)cyclobutyl)-3-methylbutyl)amino-2-methylpropan-2-yl)carbamate 21g (Scheme 4)

Colorless oil (0.728 g, 90%). $^1$HNMR (400 MHz), CDCl$_3$): δ 0.53-0.62 (m, 1H); 0.78 (d, J=6.8 Hz, 3H); 0.82 (d, J=6.8 Hz, 3H); 0.99-1.10 (m, 1H); 1.18 (t, J=7.2 Hz, 3H); 1.26 (s, 3H); 1.38 (s, 3H); 1.52-1.58 (m, 2H); 1.69-1.74 (m, 1H); 1.80-1.86 (m, 1H); 2.04-2.11 (m, 1H); 2.15-2.20 (m, 2H); 2.27-2.34 (m, 1H); 2.64-88 (m, 3H); 4.06 (q, J=7.2 Hz, 2H); 5.20 (sbroad, 1H); 6.99 (dd, J=2.0 Hz; 8.4 Hz, 1H); 7.19 (d, J=2 Hz; 1H); 7.28 (d, J=8.4 Hz, 1H). MS (ESI): m/z=430.3 (M+H$^+$).

EXAMPLE 49

Isopropyl(1-((1-(1-(3,4-dichlorophenyl)cyclobutyl)-3-methylbutyl)amino-2-methylpropan-2-yl)carbamate 21h (Scheme 4)

Colorless oil (0.4 g, 70%). $^1$HNMR (400 MHz), CDCl$_3$): δ 0.53-0.62 (m, 1H); 0.78 (d, J=6.8 Hz, 3H); 0.82 (d, J=6.8 Hz, 3H); 0.99-1.10 (m, 1H); 1.22 (d, J=6.4 Hz, 6H); 1.27 (d, J=6.4 Hz, 6H); 1.34 (sbroad, 1H); 1.52-1.58 (m, 1H); 1.69-1.74 (m, 1H); 1.80-1.86 (m, 1H); 2.04-2.11 (m, 1H); 2.15-2.20 (m, 2H); 2.27-2.34 (m, 1H); 2.64-88 (m, 3H); 4.57-4.60 (m, 1H); 5.09 (sbroad, 1H); 6.99 (dd, J=2.0 Hz; 8.4 Hz, 1H); 7.19 (d, J=2 Hz; 1H); 7.28 (d, J=8.4 Hz, 1H). MS (ESI): m/z=444.3 (M+H$^+$).

EXAMPLE 50

Ethyl(1-((1-(1-(4-ethoxyphenyl)cyclobutyl)-3-methylbutyl)amino-2-methylpropan-2-yl)carbamate 21i (Scheme 4)

Colorless oil (0.27 g, 80%). $^1$HNMR (400 MHz), CDCl$_3$): δ 0.64-0.71 (m, 1H); 0.84 (d, J=6.8 Hz, 3H); 0.88 (d, J=6.8 Hz, 3H); 1.08-1.13 (m, 1H); 1.18 (s, 3H); 1.20 (s, 3H); 1.24 (t, J=7.2 Hz, 3H); 1.42 (t, J=7.2 Hz, 3H); 1.55-1.64 (m, 2H); 1.67-1.71 (m, 1H); 1.75-1.88 (m, 1H); 2.09-2.16 (m, 1H); 2.29-2.35 (m, 3H); 2.63-2.67 (m, 2H); 2.71 (d, J=12.0 Hz, 1H); 3.94-3.99 (m, 4H); 5.40 (s, 1H); 6.84 (d, J=8.4 Hz, 2H); 7.14 (d, J=8.4 Hz, 2H). MS (ESI): m/z=405.3 (M+H$^+$).

EXAMPLE 51

Isopropyl(1-((1-(1-(4-ethoxyphenyl)cyclobutyl)-3-methylbutyl)amino-2-methylpropan-2-yl)carbamate 21j (Scheme 4)

Colorless oil (0.27 g, 62%). $^1$HNMR (400 MHz), CDCl$_3$): δ 0.55-0.62 (m, 1H); 0.78 (d, J=6.8 Hz, 3H); 0.84 (d, J=6.8 Hz, 3H); 1.08-1.13 (m, 1H); 1.22 (d, J=6.4 Hz, 6H); 1.25 (d, J=6.4 Hz, 6H); 1.42 (t, J=7.2 Hz, 3H); 1.54 (sbroad, 1H), 1.55-1.64 (m, 1H); 1.67-1.71 (m, 1H); 1.75-1.88 (m, 1H); 2.09-2.16 (m, 1H); 2.29-2.35 (m, 3H); 2.63-2.67 (m, 2H); 2.71 (d, J=11.6 Hz, 1H); 3.97 (q, J=7.2 Hz, 2H); 4.75-4.80 (m, 1H); 5.40 (s, 1H); 6.84 (d, J=8.4 Hz, 2H); 7.14 (d, J=8.4 Hz, 2H). MS (ESI): m/z=419.3 (M+H$^+$).

EXAMPLE 52

Ethyl (2-hydroxyethyl)carbamate 24a (Scheme 5)

To a stirred solution of ethyl chloroformate (4 g, 0.037 mol.) and N-hydroxysuccinimide (6.3 g, 0.055 mol.) in 10 mL of DCM at 0° C. under nitrogen atmosphere was added N,N-Diisopropylethylamine (9.5 g, 0.055 mol) in 10 mL of DCM. The progress of the reaction was monitored by thin layer chromatography (TLC). After stirring for 3 hrs at room temperature, the reaction mixture was filtered and the precipitate was washed with 2×10 mL of dichloromethane. The combined filtrate was evaporated and dissolved in 20 mL of acetonitrile, cooled in an ice-bath and then added dropwise a solution of Ethanolamine 23 (3.3 mL, 2.5 eq). The resulting mixture was stirred at ice-bath temperature for 1 h and then overnight at room temperature. The progress of the reaction was monitored by thin layer chromatography (TLC). The reaction mixture was filtered, and the precipitate was washed with 2×10 mL DCM and dried over sodium sulfate. After removing the solvent under reduced pressure, the residue was purified by silica gel column chromatography to give ethyl (2-hydroxyethyl)carbamate.

Colorless oil (4.3 g, 88%). $^1$HNMR (400 MHz), CDCl$_3$: δ 1.20 (t, J=7.2 Hz, 3H); 3.2 (sbr, 1H); 3.27 (q, J=5.2 Hz, 2H); 3.65 (t, J=4.8 Hz, 2H); 4.07 (q, J=7.2 Hz, 2H); 5.38 (sbr, 1H).

EXAMPLE 53

Isopropyl (2-hydroxyethyl)carbamate 24b (Scheme 5)

Colorless oil (4.2 g, 87%). $^1$HNMR (400 MHz), CDCl$_3$: δ 1.20 (d, J=6.0 Hz, 6H); 2.85 (sbr, 1H); 3.28 (q, J=5.2 Hz, 2H); 3.66 (t, J=5.2 Hz, 2H); 4.88-4.90 (m, 1H); 5.17 (sbr, 1H).

EXAMPLE 54

General Procedure for Synthesis of Compounds 19

Ethyl (2-hydroxyethyl) carbamate (0.7 g, 0.0052 mol.) was dissolved in DCM (10 mL) at 0° C. 4-nitrobenzene-1-sulfonyl chloride (1.2 g, 1.1 eq) in 10 mL of DCM was slowly added while the mixture was stirred at ice bath (0-5° C.). Pyridine (2.1 mL, 5 eq) was finally added and the mixture was continuously stirred at ice bath for 4 h. The progress of the reaction was monitored by TLC. After the reaction was complete, the mixture was wash with water and concentrated using a rotary evaporator. It was further purified using a column chromatography (silica gel-AcOEt/Hexane) to give 2-((ethoxycarbonyl)amino)ethyl 4-nitrobenzenesulfonate light yellow solid.

2-((Ethoxycarbony)amino)ethyl 4-nitrobenzenesulfonate 19 (Scheme 5)

Light yellow solid (1.2 g, 75%). $^1$HNMR (400 MHz), CDCl$_3$: δ 1.22 (t, J=7.2.8 Hz, 3H); 3.47 (q, J=5.2 Hz, 2H); 4.07 (q, J=7.2 Hz, 2H); 3.20 (t, J=5.2 Hz, 2H); 4.93 (sbr, 1H); 8.10 (d, J=9.2 Hz, 2H); 8.40 (d, J=9.2 Hz, 2H).

EXAMPLE 55

General Procedure for Compounds 29

To a stirred solution of ethyl chloroformate (3 g, 0.027 mol.) and N-hydroxysuccinimide (3.8 g, 0.033 mol.) in 10 mL of DCM at 0° C. under nitrogen atmosphere was added N,N-Diisopropylethylamine (7.0 mL, 0.04 mol). The progress of the reaction was monitored by thin layer chromatography (TLC). After stirring for 3 hrs at room temperature. DCM was evaporated and the residue was dissolved in 10 mL of acetonitrile, cooled in an ice-bath and then added dropwise a solution of aminoacetaldehyde diethyl acetal (4.7 mL, 1.2 eq). The resulting mixture was stirred at ice-bath temperature for 1 h and then overnight at room temperature. The progress of the reaction was monitored by thin layer chromatography (TLC). The reaction mixture was filtered, and the precipitate was washed with 2×10 mL DCM and dried over sodium sulfate. After removing the solvent under reduce pressure, the residue was purified by silica gel column chromatography to give ethyl (2,2-diethoxyethyl)carbamate as a colorless oil Ethyl (2,2-diethoxyethyl)carbamate 29 (Scheme 6)

Colorless oil (5.17 g, 94% yield). $^1$HNMR (400 MHz), CDCl$_3$: δ 1.18 (t, J=7.2 Hz, 6H); 1.20 (t, J=7.2 Hz, 3H); 3.26 (t, J=5.6 Hz, 2H); 3.51 (q, J=7.2 Hz, 2H); 3.64 (q, J=7.2 Hz, 2H); 4.08 (q, J=7.2 Hz, 2H); 4.46 (t, J=5.2 Hz, 1H); 4.87 (sbr, 1H).

EXAMPLE 56

General Procedure for Compounds 27

To a stirred solution of ethyl chloroformate (3 g, 0.027 mol.) and N-hydroxysuccinimide (3.8 g, 0.033 mol.) in 10 mL of DCM at 0° C. under nitrogen atmosphere was added N,N-Diisopropylethylamine (7.0 mL, 0.04 mol). The progress of the reaction was monitored by thin layer chromatography (TLC). After stirring for 3 hrs at room temperature. DCM was evaporated and the residue was dissolved in 10 mL of acetonitrile, cooled in an ice-bath and then added dropwise a solution of 2-amino-2-methyl-1-propanol (3.1 mL, 1.2 eq). The resulting mixture was stirred at ice-bath temperature for 1 h and then overnight at room temperature. The progress of the reaction was monitored by thin layer chromatography (TLC). The reaction mixture was filtered, and the precipitate was washed with 2×10 mL DCM and dried over sodium sulfate. After removing the solvent under reduce pressure, the residue was purified by silica gel column chromatography to give ethyl (1-hydroxy-2-methylpropan-2-yl)carbamate as a colorless oil Ethyl (1-hydroxy-2-methylpropan-2-yl)carbamate 27 (Scheme 6)

Colorless oil (3.63 g, 82%). $^1$HNMR (400 MHz), CDCl$_3$: δ 1.18 (t, J=7.2 Hz, 3H); 1.22 (s, 6H); 3.53 (d, J=6.0 Hz, 2H); 3.9 (sbroad, 1H); 4.00 (q, J=7.2 Hz, 2H); 4.91 (sbroad, 1H).

EXAMPLE 57

Isopropyl (1-hydroxy-2-methylpropan-2-yl)carbamate 27 (Scheme 6)

Colorless oil (2.8 g, 90%). $^1$HNMR (400 MHz), CDCl$_3$: δ 1.20 (d, J=6.4 Hz, 6H); 1.22 (s, 6H); 3.53 (d, J=6.0 Hz, 2H); 3.9 (sbroad, 1H); 4.82-4.88 (m, 1H); 4.91 (sbroad, 1H).

EXAMPLE 58

Ethyl (2-oxoethyl)carbamate 20a (Scheme 6)

Procedure 1: A solution of ethyl (2,2-diethoxyethyl)carbamate (2.0 g, 0.0097 mol.)) in 5 mL of THF at 0° C. was added HCl (10 mL, 2.0 eq) and then H$_2$O (0.17 mL). The solution was then stirred for 4 h at 0° C. the solvent was evaporated at room temperature and solid NaHCO$_3$ was added, filtration and concentration to give after silica gel chromatography ethyl (2-oxoethyl)carbamate as a colorless oil (0.36 g, 28%). $^1$HNMR (400 MHz), CDCl$_3$: δ 1.19 (t, J=7.2 Hz, 3H); 4.05-4.10 (m, 4H); 5.44 (sbr, 1H); 9.60 (s, 1H).

Procedure 2: To an ice-cooled and stirred solution of ethyl (1-hydroxy-2-methylpropan-2-yl)carbamate and triethylamine (1.7 mL, 2 eq) in DMSO (5 mL) was added portionwise a solution of SO$_3$.Py (1.9 g, 0.012 mol.) in DMSO (5 mL), and the whole was stirred at room temperature for 1 h. The progress of the reaction was monitored by thin layer chromatography (TLC). After the reaction was completed, the reaction mixture was poured into ice-water solution and extracted with ethyl acetate. The extracted was washed successively with aqueous HCl (0.5N), NaHCO$_3$ solution and brine, dried over MgSO₄, and concentrated under reduce pressure. The residue was purified by silica gel chromatography using gradient of hexane and ethyl acetate, ethyl (2-oxopropan-2-yl)carbamate as a colorless oil (0.129 g, 28% yield). ¹HNMR (400 MHz), CDCl₃: δ 1.19 (t, J=7.2 Hz, 3H); 4.05-4.10 (m, 4H); 5.44 (sbr, 1H); 9.60 (s, 1H).

EXAMPLE 59

Isopropyl (2-oxoethyl)carbamate 20b (Scheme 6)

Synthesized according to procedure 2 used for 20a. Colorless oil (0.15 g, 13% yield). ¹HNMR (400 MHz), CDCl₃: δ 1.22 (d, J=6.0 Hz, 6H); 4.09 (t, J=4.4 Hz, 2H); 4.86-4.93 (m, 1H); 5.25 (sbr, 1H); 9.63 (s, 1H).

EXAMPLE 60

Ethyl (2-methyl-1-oxopropan-2-yl)carbamate 20c (Scheme 6)

Synthesized according to procedure 2 used for 20a. Colorless oil (0.64 g, 66% yield). ¹HNMR (400 MHz), CDCl₃: δ 1.21 (t, J=7.2 Hz, 3H); 1.35 (s, 6H); 4.08 (q, J=7.2 Hz, 2H); 5.21 (sbroad, 1H); 9.40 (s, 1H).

EXAMPLE 61

Isopropyl (2-methyl-1-oxopropan-2-yl)carbamate 20d (Scheme 6)

Synthesized according to procedure 2 used for 20a. Colorless oil (1.18 g, 60% yield). ¹HNMR (400 MHz), CDCl₃: δ 1.20 (d, J=6.8 Hz, 6H); 1.33 (s, 6H); 4.85-4.88 (m, 1H); 5.10 (sbroad, 1H); 9.40 (s, 1H).

EXAMPLE 62

N-(2-((1-(1-(3,4-Dichlorophenyl)cyclobutyl)-3-methylbutyl)amino)ethyl)butyramide 31a (Scheme 7)

A solution of 1-(1-(3,4-dichlorophenyl))cyclobutyl)-3-methylbutan-1-amine (0.5 g, 0.0017 mol) and N-(2-oxoethyl) butyramide (0.225 g, 0.0017 mol) in Ethanol anhydrous (10 mL) was stirred for 15 hours at 60° C. After the reaction was completed, the reaction mixture was cooled down to 0° C. and NaBH₄ (0.32 g, 5.0 eq) was added. The reaction mixture was stirred for 6 hours from 0° C. to rt, And then NaHCO₃ solution was added. The product was extracted with ethyl acetate, dried over Na₂SO₄ and evaporated under reduced pressure to give N-(2-((1-(1-(3,4-dichlorophenyl)cyclobutyl)-3-methylbutyl)amino)ethyl)butyramide which was purified by silica gel column chromatography using gradient of Dichloromethane and methanol (0% to 1%) and then hexane ethyl acetate (50% to 100%), isolated as a colorless oil (0.180 g, 20%).
¹HNMR (400 MHz, CDCl₃): δ 0.60-0.67 (m, 1H); 0.84 (d, J=6.8 Hz, 3H); 0.88 (d, J=6.8 Hz, 3H); 0.94 (t, J=7.2 Hz, 3H); 1.05-1.12 (m, 1H); 1.61-1.67 (m, 3H); 1.74-1.80 (m, 1H); 1.83-1.92 (m, 1H); 2.16 (t, J=7.2 Hz, 3H); 2.22-2.29 (m, 2H); 2.32-2.37 (m, 1H); 2.73 (dd, J=2.4 Hz; 10.0 Hz, 1H); 2.80-2.86 (m, 1H); 2.88-2.94 (m, 1H); 3.23-3.30 (m, 2H); 5.94 (sbroad, 1H); 7.03 (dd, J=2.0 Hz; 8.4 Hz, 1H); 7.28 (d, J=2 Hz; 1H); 7.34 (d, J=8.4 Hz, 1H). MS (ESI): m/z=400.3 (M+H⁺).

EXAMPLE 63

N-(2-((1-(1-(4-Ethoxyphenyl)cyclobutyl)-3-methylbutyl)amino)ethyl)butyramide 31b (Scheme 7)

Colorless oil (0.07, 27%). ¹HNMR (400 MHz), CDCl₃): δ 0.64-0.71 (m, 1H); 0.83 (d, J=6.8 Hz, 3H); 0.88 (d, J=6.8 Hz, 3H); 0.93 (t, J=7.6 Hz, 3H); 1.08-1.14 (m, 1H); 1.39 (t, J=7.2 Hz, 3H); 1.59-1.68 (m, 3H); 1.74-1.79 (m, 1H); 1.81-1.84 (m, 1H); 2.10-2.15 (m, 3H); 2.28-2.33 (m, 3H); 2.69 (dd, J=2.4 Hz; 10.0 Hz, 1H); 2.83-2.88 (m, 2H); 3.20-3.25 (m, 2H); 4.03 (q, J=6.8 Hz, 2H); 6.50 (sbroad, 1H); 6.83 (d, J=8.8 Hz, 2H); 7.12 (d, J=8.8 Hz, 2H). MS (ESI): m/z=375.3 (M+H⁺).

EXAMPLE 64

N-(2-Oxoethyl)butyramide 30 (Scheme 8)

A solution of N-(2,2-diethoxyethyl)butyramide (2.0 g, 0.0098 mol.)) in 10 mL of THF at 0° C. was added HCl (2N) in ether (4.9 mL, 1.0 eq) and water (0.34 mL, 2 eq). The solution was then stirred for 2 to 3 h at 0° C. the solvent was evaporated at room temperature and solid NaHCO₃ was added, filtration and concentration to give after silica gel chromatography N-(2-oxoethyl)butyramide as a colorless oil (0.55 g g, 55% yield).
¹HNMR (400 MHz, CDCl₃): δ 0.89 (t, J=7.2 Hz, 3H); 1.58-1.63 (m, 2H); 2.12 (t, J=7.2 Hz, 2H); 4.17 (d, J=5.2 Hz, 2H); 6.31 (sbroad, 1H); 9.63 (s, 1H).

EXAMPLE 65

Methyl 4-oxobutanoate 32 (Scheme 9)

To a stirred solution of DMSO (2.9 mL., 4.4 eq) in 10 mL of DCM anhydrous at −75° C. was added drop by drop a solution of oxalyl chloride (1.7 mL, 2.2 eq). After 1 hour of reaction, methyl 4-hydroxybutanoate (1.1 g, 0.0093 mol.) in 10 mL of DCM was added. After the addition was completed, the reaction mixture was stirred for 1 hour, warm-up to −45° C. and then triethylamine (7.7 mL, 6 eq)) was added. The reaction mixture was stirred for 18 hours. The progress of the reaction was monitored by thin layer chromatography (TLC). After the reaction was complete, saturated sodium bicarbonate was added and extracted with DCM. The Organic layer was dried over Na₂SO₄ and concentrated on rotavap to give methyl 4-oxobutanoate which was purified by silica gel chromatography using gradient of hexane and ethyl acetate.
Colorless oil (0.57 g, 53% yield). ¹HNMR (400 MHz, CDCl₃): δ 2.60 (t, J=6.8 Hz, 2H); 2.77 (t, J=6.8 Hz, 2H); 3.66 (s, 3H); 9.78 (s, 1H).

EXAMPLE 66

General Procedure for Compounds 13 (Scheme 9)

Methyl 4-((1-(1-(4-ethoxyphenyl)cyclobutyl)-3-methylbutyl)amino)butanoate 13a (Scheme 9)

A solution of 1-(1-(4-ethoxyphenyl))cyclobutyl)-3-methylbutan-1-anamine (0.619 g, 0.0023 mol) and methyl 4-oxobutanoate (0.25 g, 0.0021 mol) in methanol anhydrous (10 mL) was stirred for 15 hour at reflux. The reaction mixture was cooled down to 0° C., And then NaBH₄ (0.4 g, 5 eq) was added. The reaction mixture was stirred from 0° C. to room temperature for 4 hours. The progress of the reaction was monitored by thin layer chromatography (TLC). After the reaction was completed, the reaction mixture was concentrated under reduce pressure. The residue was taken with Ethyl acetate and then washed with NaHCO$_3$ solution. dried over Na$_2$SO$_4$ and evaporated under reduced pressure to give methyl 4-((1-(1-(4-ethoxyphenyl)cyclobutyl)-3-methylbutyl)amino)butanoate which was purified by silica gel column chromatography using gradient of hexane and ethyl acetate, isolated as a (0.55 g, 73% yield).

$^1$HNMR (400 MHz, CDCl$_3$): δ 0.59-0.66 (m, 1H); 0.80 (d, J=6.8 Hz, 3H); 0.85 (d, J=6.8 Hz, 3H); 1.02-1.08 (m, 1H); 1.39 (t, J=6.8 Hz, 3H); 1.59-1.63 (m, 1H); 1.67-1.76 (m, 3H); 1.79-1.85 (m, 1H); 2.10-2.14 (m, 1H); 2.24-2.34 (m, 3H); 2.36-2.40 (m, 2H); 2.66 (dd, J=2.8 Hz; 10 Hz, 1H); 2.74 (t, J=6.8 Hz, 2H); 3.65 (s, 3H); 4.01 (q, J=7.2 Hz, 2H); 6.82 (d, J=8.8 Hz, 2H); 7.12 (d, J=8.8 Hz, 2H). MS (ESI): m/z=362.3 (M+H$^+$).

EXAMPLE 67

Methyl 4-((1-(1-(3,4-dichlorophenyl)cyclobutyl)-3-methylbutyl)amino)butanoate 13b (Scheme 9)

Colorless oil (0.47 g, 70%). $^1$HNMR (400 MHz, CDCl$_3$): δ 0.59-0.66 (m, 1H); 0.80 (d, J=6.8 Hz, 3H); 0.85 (d, J=6.8 Hz, 3H); 1.02-1.08 (m, 1H); 1.59-1.63 (m, 1H); 1.67-1.76 (m, 3H); 1.79-1.85 (m, 1H); 2.10-2.14 (m, 1H); 2.24-2.34 (m, 3H); 2.36-2.40 (m, 2H); 2.66 (dd, J=2.8 Hz; 10 Hz, 1H); 2.74 (t, J=6.8 Hz, 2H); 3.65 (s, 3H); 6.98 (d, J=8.4 Hz, 1H); 7.22 (s, 1H); 7.36 (d, J=8.4 Hz, 1H). MS (ESI): m/z=387.3 (M+H$^+$).

EXAMPLE 68

General Procedure for Compounds 33a-b 4-((1-(3,4-Dichlorophenyl)cyclobutyl)-3-methylbutyl)amino)butanamide 33a (Scheme 9)

A solution of methyl 4-((1-(1-(3,4-dichlorophenyl)cyclobutyl)-3-methylbutyl)amino)butanoate (0.50 g) and ammonia, 7N in methanol (30 mL) (excess) was taken in a sealed tube. The reaction mixture was reflux (70° C.) for 15 h. After the reaction was completed, the solvent was evaporated. The residue was purified by silica gel chromatography to give 4-((1-(3,4-dichlorophenyl)cyclobutyl)-3-methylbutyl)amino)butanamide as a colorless oil (0.62 g, 67%).

$^1$HNMR (400 MHz, CDCl$_3$): δ 0.57-0.64 (m, 1H); 0.82 (d, J=6.8 Hz, 3H); 0.87 (d, J=6.8 Hz, 3H); 1.04-1.07 (m, 1H); 1.55-1.63 (m, 1H); 1.71-1.79 (m, 3H); 1.82-1.92 (m, 1H); 2.08-2.15 (m, 1H); 2.18-2.40 (m, 5H); 2.70-2.75 (m, 2H); 2.80-2.86 (m, 1H); 5.42 (sbroad, 1H); 5.70 (sbroad, 1H); 7.03 (dd, J=2.0 Hz; 8.4 Hz, 1H); 7.29 (d, J=2.0 Hz, 1H); 7.33 (d, J=8.4 Hz, 1H). MS (ESI): m/z=372.3 (M+H$^+$).

EXAMPLE 69

(R)-4-((1-(1-3,4-Dichlorophenyl)cyclobutyl)-3-methylbutyl)amino)butanamide-(Isomer-1)

Separated by chiral HPLC method. Colorless oil (0.08 g, 45%). $^1$HNMR (400 MHz, DMSO): δ 0.53-0.59 (m, 1H); 0.78 (d, J=6.8 Hz, 3H); 0.83 (d, J=6.8 Hz, 3H); 0.92-0.98 (m, 1H); 1.58-1.69 (m, 4H); 1.84-1.86 (m, 1H); 2.09-2.11 (m, 5H); 2.18-2.20 (m, 2H); 2.33-3.73 (m, 4H); 6.67 (sbroad, 1H); 7.20 (dd, J=2.0 Hz; 8.4 Hz, 1H); 7.41 (d, J=2.0 Hz, 1H). 7.52 (d, J=8.4 Hz, 1H). MS (ESI): m/z=372.3 (M+H$^+$).

EXAMPLE 70

(S)-4-(1-(1-3,4-Dichlorophenyl)cyclobutyl)-3-methylbutyl)amino)butanamide-(Isomer-2)

Separated by chiral HPLC method. Colorless oil (0.07 g, 38%). $^1$HNMR (400 MHz, DMSO): δ 0.54-0.59 (m, 1H); 0.78 (d, J=6.8 Hz, 3H); 0.83 (d, J=6.8 Hz, 3H); 0.93-0.99 (m, 1H); 1.57-1.69 (m, 4H); 1.84-1.87 (m, 1H); 2.07-2.14 (m, 4H); 2.18-2.22 (m, 1H); 2.33-2.40 (m, 1H); 2.58-3.32 (m, 3H); 4.33 (d, J=4 Hz, 1H); 6.67 (sbroad, 1H); 7.19 (dd, J=1.6 Hz; 8.4 Hz, 1H); 7.41 (d, J=1.6 Hz, 1H). 7.52 (d, J=8.4 Hz, 1H). MS (ESI): m/z=372.3 (M+H$^+$).

EXAMPLE 71

4-((1-(4-Ethoxyphenyl)cyclobutyl)-3-methylbutyl)amino)butanamide 33b (Scheme 9)

Colorless oil (0.28 g, 58%). $^1$HNMR (400 MHz, CDCl$_3$): δ 0.63-0.69 (m, 1H); 0.81 (d, J=6.8 Hz, 3H); 0.86 (d, J=6.8 Hz, 3H); 1.05-1.08 (m, 1H); 1.39 (t, J=7.2 Hz, 3H); 1.55-1.64 (m, 1H); 1.68-1.77 (m, 3H); 1.79-1.86 (m, 1H); 2.08-2.15 (m, 1H); 2.43-2.33 (m, 5H); 2.68 (dd, J=2.4 Hz; 10.0 Hz, 1H); 2.74-2.82 (m, 3H); 4.09 (q, J=7.2 Hz, 2H); 5.32 (sbroad, 1H); 6.08 (sbroad, 1H); 6.82 (d, J=8.8 Hz, 2H); 7.12 (d, J=8.8 Hz, 2H). MS (ESI): m/z=347.3 (M+H$^+$).

EXAMPLE 72

General Procedure for 33c-33j

Trimethyl aluminium 2.0 M solution in toluene (3 eq) was added drop wise to a stirred solution of compounds 13 (1 eq) and corresponding amines (6 eq) in 10 mL of toluene under N$_2$ atmosphere at 0° C. in a sealed tube. The reaction mixture was slowly raised to 70° C. for 1 hour. After the reaction was completed, the mixture was distilled under vacuo to get after silica gel chromatography 4-((1-(1-(4-ethoxyphenyl)cyclobutyl)-3-methylbutyl)amino)-N-ethylbutanamide as colorless oil.

4-((1-(3,4-Dichlorophenyl)cyclobutyl)-3-methylbutyl)amino)-N-methylbutanamide 33c (Scheme 9)

Colorless oil (0.32 g, 66%). $^1$HNMR (400 MHz, CDCl$_3$): δ 0.57-0.64 (m, 1H); 0.82 (d, J=6.8 Hz, 3H); 0.87 (d, J=6.8 Hz, 3H); 1.01-1.05 (m, 1H); 1.55-1.61 (m, 1H); 1.70-1.78 (m, 3H); 1.88-1.87 (m, 1H); 2.10-2.13 (m, 1H); 2.18-2.28 (m, 4H); 2.33-2.372 (m, 1H); 2.67-2.73 (m, 2H); 2.77 (d, J=4.8 Hz, 3H); 2.79-2.82 (m, 1H); 5.64 (sbroad, 1H); 7.04 (dd, J=2.4 Hz; 8.4 Hz, 1H); 7.29 (d, J=2.4 Hz, 1H); 7.33 (d, J=8.4 Hz, 1H). MS (ESI): m/z=386.3 (M+H$^+$).

EXAMPLE 73

4-((1-(1-(3,4-Dichlorophenyl)cyclobutyl)-3-methylbutyl)amino)-N-ethylbutanamide 33d (Scheme 9)

Colorless oil (0.64 g, 66%). $^1$HNMR (400 MHz, DMSO): δ 0.54-0.60 (m, 1H); 0.78 (d, J=6.4 Hz, 3H); 0.83 (d, J=6.8 Hz, 3H); 0.87-0.95 (m, 1H); 0.98 (t, J=7.2 Hz, 3H); 1.57-1.69 (m, 4H); 1.84-1.87 (m, 1H); 2.07-2.14 (m, 3H); 2.18-2.22 (m, 1H); 2.33-2.37 (m, 1H); 2.60-2.69 (m, 3H); 3.00-3.07 (m, 2H); 3.17 (d, J=5.2 Hz, 1H); 7.20 (d, J=8.4 Hz, 1H); 7.41 (s, 1H); 7.52 (d, J=8.4 Hz, 1H). 7.71 (sbroad, 1H). MS (ESI): m/z=400.2 (M+H$^+$).

EXAMPLE 74

4-((1-(1-(3,4-Dichlorophenyl)cyclobutyl)-3-methylbutyl)amino)-N-propylbutanamide 33e (Scheme 9)

Colorless oil (0.62 g, 67%). $^1$HNMR (400 MHz, DMSO): δ 0.54-0.60 (m, 1H); 0.77-0.84 (m, 8H); 0.88 (sbroad, 1H); 0.92-0.98 (m, 1H); 1.17 (t, J=7.2 Hz, 1H); 1.33-1.40 (m, 2H); 1.57-1.69 (m, 4H); 1.83-1.85 (m, 1H); 2.08-2.14 (m, 3H); 2.18-2.21 (m, 1H); 2.33-2.37 (m, 1H); 2.61-2.70 (m, 3H); 2.98 (q, J=6.8 Hz, 2H); 7.19 (d, J=8.4 Hz, 1H); 7.40 (s, 1H); 7.51 (d, J=8.4 Hz, 1H). 7.71 (t, J=4.8 Hz, 1H). MS (ESI): m/z=414.2 (M+H$^+$).

EXAMPLE 75

4-((1-(1-(3,4-Dichlorophenyl)cyclobutyl)-3-methylbutyl)amino)-N-isopropylbutanamide 33f (Scheme 9)

Colorless oil (0.72 g, 66%). $^1$HNMR (400 MHz, DMSO): δ 0.57-0.59 (m, 1H); 0.78 (d, J=6.8 Hz, 3H); 0.82 (d, J=6.8 Hz, 3H); 0.92-0.98 (m, 2H); 1.01 (d, J=6.4 Hz, 6H); 1.60 (t, J=6.8 Hz, 3H); 1.66-1.67 (m, 1H); 1.76-1.80 (m, 1H); 2.06 (t, J=7.6 Hz, 2H); 2.12-2.39 (m, 6H); 3.78-3.83 (m, 1H); 7.19 (dd, J=1.6 Hz; 8.4 Hz, 1H); 7.40 (d, J=1.6 Hz, 1H). 7.52 (d, J=8.4 Hz, 1H); 7.58 (d, J=7.2 Hz, 1H). MS (ESI): m/z=414.2 (M+H$^+$).

EXAMPLE 76

4-((1-(1-(4-Ethoxyphenyl)cyclobutyl)-3-methylbutyl)amino)-N-methylbutanamide 33g (Scheme 9)

Colorless oil (0.56 g, 65%). $^1$HNMR (400 MHz, CDCl$_3$): δ 0.63-0.700 (m, 1H); 0.81 (d, J=6.8 Hz, 3H); 0.85 (d, J=6.8 Hz, 3H); 1.05-1.11 (m, 1H); 1.36 (t, J=7.2 Hz, 3H); 1.58-1.62 (m, 1H); 1.66-1.78 (m, 3H); 1.88-1.87 (m, 1H); 2.11-2.13 (m, 1H); 2.22-2.33 (m, 5H); 2.65-2.75 (m, 6H); 4.01 (q, J=7.2 Hz, 2H); 6.08 (sbroad, 1H); 6.82 (d, J=8.4 Hz, 2H); 7.11 (d, J=8.4 Hz, 2H). MS (ESI): m/z=361.3 (M+H$^+$).

EXAMPLE 77

4-((1-(1-(4-Ethoxyphenyl)cyclobutyl)-3-methylbutyl)amino)-N-ethylbutanamide 33h (Scheme 9)

Colorless oil (0.67 g, 66%). $^1$HNMR (400 MHz, DMSO): δ 0.57-0.60 (m, 1H); 0.64 (sbroad, 1H); 0.77 (d, J=6.8 Hz, 3H); 0.80 (d, J=6.8 Hz, 3H); 0.92-1.00 (m, 4H); 1.31 (t, J=6.8 Hz, 3H); 1.57-1.66 (m, 4H); 1.76-1.80 (m, 1H); 2.06-2.17 (m, 5H); 2.28-2.32 (m, 1H); 2.64-2.65 (m, 2H); 3.00-3.07 (m, 2H); 3.98 (q, J=6.8 Hz, 2H); 6.83 (d, J=8.8 Hz, 2H); 7.13 (d, J=8.8 Hz, 2H). 7.71 (sbroad, 1H). MS (ESI): m/z=375.2 (M+H$^+$).

EXAMPLE 78

4-((1-(1-(4-Ethoxyphenyl)cyclobutyl)-3-methylbutyl)amino)-N-propylbutanamide 33i (Scheme 9)

Colorless oil (0.74 g, 66%). $^1$HNMR (400 MHz, DMSO): δ 0.54-0.60 (m, 1H); 0.67 (sbroad, 1H); 0.76-0.84 (m, 8H); 0.92-0.98 (m, 1H); 1.29-1.40 (m, 5H); 1.56-1.66 (m, 4H); 1.78-1.82 (m, 1H); 2.06-2.17 (m, 5H); 2.28-2.33 (m, 1H); 2.58 (d, J=8.8 Hz, 1H); 2.66 (t, J=6.4 Hz, 2H); 2.97 (q, J=6.8 Hz, 2H); 3.98 (q, J=6.8 Hz, 2H); 6.83 (d, J=8.4 Hz, 2H); 7.12 (d, J=8.4 Hz, 2H). 7.71 (sbroad, 1H). MS (ESI): m/z=389.2 (M+H$^+$).

EXAMPLE 79

4-((1-(1-(4-Ethoxyphenyl)cyclobutyl)-3-methylbutyl)amino)-N-isopropylbutanamide 33j (Scheme 9)

Colorless oil (0.64 g, 66%). $^1$HNMR (400 MHz, DMSO): δ 0.57-0.60 (m, 1H); 0.64 (sbroad, 1H); 0.77 (d, J=6.8 Hz, 3H); 0.80 (d, J=6.8 Hz, 3H); 0.92-0.98 (m, 1H); 1.01 (d, J=6.4 Hz, 6H); 1.31 (t, J=6.8 Hz, 3H); 1.56-1.64 (m, 4H); 1.76-1.80 (m, 1H); 2.05 (t, J=7.6 Hz, 2H); 2.14 (q, J=8.4 Hz, 3H); 2.30-2.32 (m, 1H); 2.64-2.66 (m, 2H); 3.78-3.81 (m, 1H); 3.98 (q, J=7.2 Hz, 2H); 6.83 (d, J=8.4 Hz, 2H); 7.12 (d, J=8.4 Hz, 2H). 7.58 (d, J=7.2 Hz, 1H). MS (ESI): m/z=389.2 (M+H$^+$).

EXAMPLE 80

General Procedure for Compounds 35

A solution of 1-(1-(3,4-dichlorophenyl))cyclobutyl)-3-methylbutan-1-amine (0.32 g, 0.0011 mol) and isopropyl (2-oxoethyl)carbonate (0.15 g, 0.0010 mol) in Ethanol anhydrous (10 mL) was stirred for 15 hours at 50° C. After the reaction was complete, the reaction mixture was cooled down to 0° C. and NaBH$_4$ (0.3 g, 5.0 eq) was added. The reaction mixture was stirred for 6 hours from 0° C. to rt, And then NaHCO$_3$ solution was added. The product was extracted with ethyl acetate, dried over Na$_2$SO$_4$ and evaporated under reduced pressure to give (1-((1-(3,4-dichlorophenyl)cyclobutyl)-3-methylbutyl)amino)ethyl isopropyl carbonate which was purified by silica gel column chromatography using gradient of hexane and ethyl acetate, isolated as a colorless oil.

2-((1-(1-(3,4-dichlorophenyl)cyclobutyl)-3-methylbutyl)amino)ethyl isopropyl carbonate 35a (Scheme 10)

Colorless oil (0.23 g, 57%). $^1$HNMR (400 MHz, CDCl$_3$): δ 0.60-0.67 (m, 1H); 0.82 (d, J=6.8 Hz, 3H); 0.86 (d, J=6.8 Hz, 3H); 1.01-1.08 (m, 1H); 1.28 (d, J=6.4 Hz, 6H); 1.56-1.63 (m, 2H); 1.73-1.78 (m, 1H); 1.84-1.90 (m, 1H); 2.10-2.13 (m, 1H); 2.19-2.26 (m, 2H); 2.34-2.37 (m, 1H); 2.74 (dd, J=2.4 Hz; 10 Hz, 1H); 2.91-2.97 (m, 1H); 3.03-3.09 (m, 1H); 4.09-4.17 (m, 2H); 4.83-4.89 (m, 2H); 7.03 (dd, J=2 Hz; 8.4 Hz, 1H); 7.28 (d, J=2 Hz, 1H); 7.32 (d, J=8.4 Hz, 1H). MS (ESI): m/z=417.3 (M+H$^+$).

EXAMPLE 81

2-((1-(1-(4-ethoxyphenyl)cyclobutyl)-3-methylbutyl) amino)ethyl isopropyl carbonate 35b (Scheme 10)

Colorless oil (0.2 g, 56%). $^1$HNMR (400 MHz, CDCl$_3$): δ 0.64-0.70 (m, 1H); 0.81 (d, J=6.8 Hz, 3H); 0.85 (d, J=6.8 Hz, 3H); 1.03-1.14 (m, 1H); 1.28 (d, J=6.4 Hz, 6H); 1.39 (t, J=6.8 Hz, 3H); 1.53-1.65 (m, 2H); 1.70-1.79 (m, 1H); 1.80-1.89 (m, 1H); 2.08-2.15 (m, 1H); 2.23-2.37 (m, 3H); 2.69 (dd, J=2.4 Hz; 10 Hz, 1H); 2.98 (t, J=5.6 Hz, 2H); 4.01 (q, J=6.8 Hz, 2H);

4.12 (td, J=1.2 Hz; 6 Hz, 2H); 4.83-4.87 (m, 1H); 6.81 (d, J=8.8 Hz, 2H); 7.12 (d, J=8.8 Hz, 2H). MS (ESI): m/z=392.3 (M+H$^+$).

EXAMPLE 82

2-((1-(1-(4-buthoxyphenyl)cyclobutyl)-3-methylbutyl)amino)ethyl ethyl carbonate 35c (Scheme 10)

Colorless oil (0.26 g, 55%). $^1$HNMR (400 MHz, CDCl$_3$): δ 0.63-0.70 (m, 1H); 0.81 (d, J=6.8 Hz, 3H); 0.85 (d, J=6.8 Hz, 3H); 0.97 (t, J=7.2 Hz, 3H); 1.04-1.10 (m, 1H); 1.29 (t, J=7.2 Hz, 3H); 1.43-1.50 (m, 2H); 1.60-1.62 (m, 1H); 1.71-1.78 (m, 3H); 1.82-1.85 (m, 1H); 2.10-2.13 (m, 1H); 2.25-2.34 (m, 3H); 2.69 (dd, J=2.8 Hz; 10 Hz, 1H); 2.98 (t, J=5.6 Hz, 2H); 3.93 (t, J=6.4 Hz, 2H); 4.11-4.20 (m, 4H); 6.81 (d, J=8.8 Hz, 2H); 7.12 (d, J=8.8 Hz, 2H). MS (ESI): m/z=406.3 (M+H$^+$).

EXAMPLE 83

Ethyl(2-hydroxyethyl)carbonate 38a (Scheme 11)

To a stirred solution of isopropyl chloroformate (2 g, 0.016 mol.) in 10 mL of DCM at 0° C. under nitrogen atmosphere was added pyridine (3.8 mL, 0.048 mol) and then ethylene glycol (2.7 mL, 3 eq). The progress of the reaction was monitored by thin layer chromatography (TLC). After stirring for 15 hrs at room temperature. After removing the solvent under reduce pressure, the residue was purified by silica gel column chromatography to give 2-hydroxyethyl isopropyl carbonate as a colorless oil (0.5 g, 42% yield). $^1$HNMR (400 MHz, CDCl$_3$): δ 1.22 (t, J=7.2 Hz, 3H); 2.94 (sbroad, 1H); 3.78 (t, J=4.4 Hz, 2H); 4.18 (t, J=4.4 Hz, 2H); 4.07 (q, J=7.2H, 2H).

EXAMPLE 84

2-Hydroxyethyl isopropyl carbonate 38b (Scheme 11)

Colorless oil (0.50 g, 42%). $^1$HNMR (400 MHz, CDCl$_3$): δ 1.24 (d, J=6.4 Hz, 6H); 2.94 (sbroad, 1H); 3.78 (t, J=4.4 Hz, 2H); 4.18 (t, J=4.4 Hz, 2H); 4.78-4.85 (m, 1H).

EXAMPLE 85

General Procedure for Compounds 34

To an ice-cooled and stirred solution of 2-hydroxy isopropyl carbonate (1.06 g, 0.0071 mol) and triethylamine (2.0 mL, 2 eq) in DMSO (5 mL) was added portionwise a solution of SO$_3$.Py (2.3 g, 0.014 mol.) in DMSO (5 mL), and the whole was stirred at room temperature for 1 h. The progress of the reaction was monitored by thin layer chromatography (TLC). After the reaction was complete, the reaction mixture was poured into ice-water solution and extracted with ethyl acetate. The extracted was washed successively with aqueous HCl (0.5N), NaHCO$_3$ solution and brine, dried over MgSO$_4$, and concentrated under reduce pressure. The residue was purified by silica gel chromatography using gradient of hexane and ethyl acetate, isopropyl (2-oxoethyl) carbonate isolated as a colorless oil Ethyl (2-oxoethyl)carbonate 34a (Scheme 11)

Colorless oil (0.54 g, 50%). $^1$HNMR (400 MHz, CDCl$_3$): δ 1.22 (t, J=7.2 Hz, 3H); 4.63 (d, J=0.8 Hz, 2H); 4.07 (q, J=7.2 Hz, 2H); 9.62 (s, 1H).

EXAMPLE 86

Isopropyl (2-oxoethyl) carbonate 34b (Scheme 11)

Colorless oil (0.40 g, 38%). $^1$HNMR (400 MHz, CDCl$_3$): δ 1.31 (d, J=6.4 Hz, 6H); 4.63 (d, J=0.8 Hz, 2H); 4.86-4.91 (m, 1H); 9.62 (s, 1H).

EXAMPLE 87

In Vitro Pharmacology Results

The monoamine transporters inhibitory activities of selected compounds cycloalkylmethylamine derivatives comprising Formula (I) are reported herein. The compounds were evaluated using well established radioligand binding assays protocols (Galli, A. et al., J. Exp. Biol. 1995, 198, 2197-2212; Giros, B. et al., Trends Pharmcol. Sci. 1993, 14, 43-49; Gu, H. et al., J. Biol. Chem. 1994, 269(10), 7124-7130; Shearman, L. P. et al, Am. J. Physiol., 1998, 275(6 Pt 1), C1621-1629; Wolf, W. A. et al., J. Biol. Chem. 1992, 267(29), 20820-20825). The human recombinant transporter proteins dopamine (DAT), norepinephrine (NET) and serotonin (SERT) were selected for the in vitro assays. The radioligand binding assays were carried out at 11 different test concentrations 0.1 nm to 1 μM.

The assays were carried out in duplicates and the quantitative data are reported as Ki in the TABLE 1.

TABLE 1

| Compound | DAT Ki (nM) | NET Ki (nM) | SERT Ki (nM) |
|---|---|---|---|
| 12q | 7.2 | 38.2 | 10.6 |
| 12u | 80.4 | 2340 | 5.7 |
| 21a | 38.4 | 13.4 | 1 |
| 21b | 158.5 | 1924 | 2.0 |
| 31a | 52.7 | 77.7 | 27.8 |
| 31b | 251.4 | 4728 | 25 |
| 33a -Racemic | 1.5 | 50.1 | 8.1 |
| 33a -(R)-Isomer | 0.91 | 30.3 | 2.3 |
| 33a -(S)-Isomer | 126.1 | 3415 | 299.7 |
| 33b -Racemic | 471.6 | >10,000 | 5.49 |
| 33b -(R)-Isomer | 130.3 | 6515 | 2.79 |
| 33b -(S)-Isomer | 4026 | 1086 | 328.9 |

What is claimed is:

1. A method for treating obesity or depression, comprising:
identifying a patient suffering from obesity or depression, and
administering to the patient an effective amount of a compound of Formula (I):

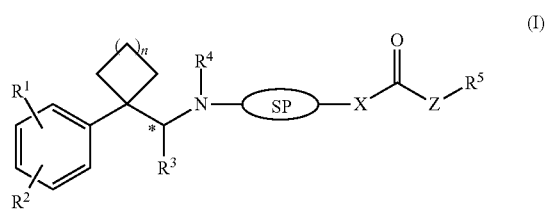

or a pharmaceutically acceptable salt thereof, wherein:
n is 1;
SP is a spacer of C$_{1-6}$ alkylene;
X is O, S, or NH;
Z is O, S, NH, or a direct bond;

$R^1$ and $R^2$ are halogen;

$R^3$ is hydrogen, alkyl, aryl, arylalkyl, cycloalkyl, cycloheteroalkyl, heteroaryl, or heteroarylalkyl;

$R^4$ is hydrogen or alkyl;

$R^5$ is hydrogen, $C_{1-6}$ alkyl, aryl, arylalkyl, cycloalkyl, cycloheteroalkyl, heteroaryl;

optionally one or more hydrogen of $R^1$, $R^2$, $R^3$, $R^4$, or $R^5$ is substituted with $^2H$ (deuterium), and "*" denotes a carbon capable of being optically active.

2. The method of claim 1, wherein X is O.

3. The method of claim 1, wherein X is NH.

4. The method of claim 1, wherein Z is O.

5. The method of claim 1, wherein Z is NH.

6. The method of claim 1, wherein Z is a direct bond.

7. The method of claim 1, wherein $R^3$ is hydrogen, methyl, ethyl, propyl, isopropyl, butyl, or isobutyl.

8. The method of claim 1, wherein $R^5$ is hydrogen, $C_{1-6}$ alkyl, or $C_{1-6}$ alkoxy.

9. The method of claim 1, wherein $R^5$ is $C_{1-6}$ alkyl.

10. The method of claim 1, wherein the compound has the structural Formula (III):

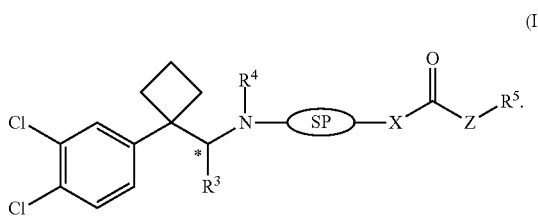

11. The method of claim 1, wherein the compound has the structural Formula (IV):

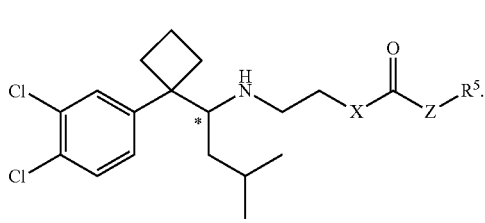

12. The method of claim 1, wherein the compound has the structural Formula (VI):

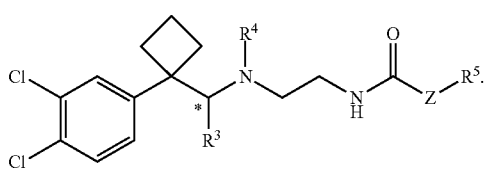

13. The method of claim 12, wherein Z is O, $R^3$ is i-butyl, $R^4$ is H, and $R^5$ is $C_{1-6}$ alkyl.

14. The method of claim 1, wherein the compound has the structural Formula (VII):

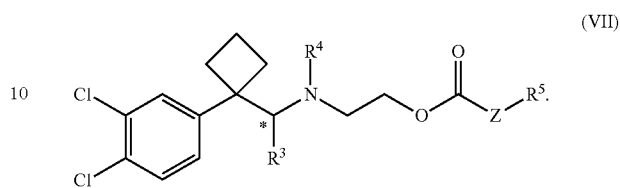

15. The method of claim 1, wherein the compound has the structural Formula (VIII):

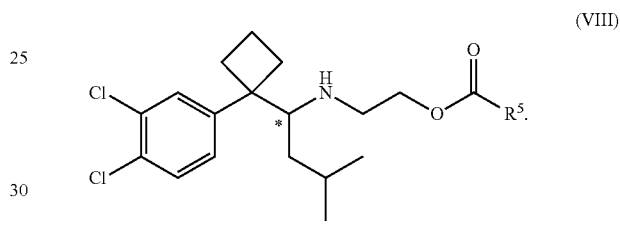

16. The method of claim 15, wherein $R^5$ is ethyl.

17. The method of claim 1, wherein the compound has the structural Formula (IX):

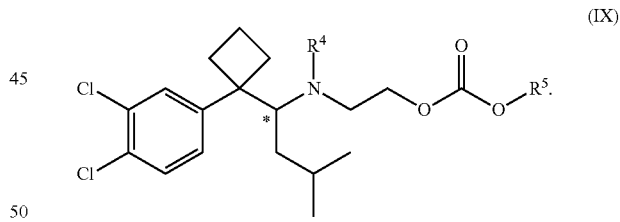

18. The method of claim 1, wherein the carbon denoted with the * is in the R configuration.

19. The method of claim 1, which treats obesity.

20. The method of claim 12, wherein Z is a direct bond, $R^3$ is i-butyl, $R^4$ is H, and $R^5$ is $C_{1-6}$ alkyl.

* * * * *